(12) United States Patent
Knight et al.

(10) Patent No.: US 11,357,431 B2
(45) Date of Patent: *Jun. 14, 2022

(54) METHODS AND APPARATUS TO IDENTIFY A MOOD OF MEDIA

(71) Applicant: The Nielsen Company (US), LLC, New York, NY (US)

(72) Inventors: Robert T. Knight, Berkeley, CA (US); Ramachandran Gurumoorthy, Berkeley, CA (US); Alexander Topchy, New Port Richey, FL (US); Ratnakar Dev, Berkeley, CA (US); Padmanabhan Soundararajan, Tampa, FL (US); Anantha Pradeep, Piedmont, CA (US)

(73) Assignee: The Nielsen Company (US), LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/073,117

(22) Filed: Oct. 16, 2020

(65) Prior Publication Data

US 2021/0128040 A1    May 6, 2021

Related U.S. Application Data

(63) Continuation of application No. 15/785,050, filed on Oct. 16, 2017, now Pat. No. 10,806,388, which is a (Continued)

(51) Int. Cl.
*G06Q 30/00* (2012.01)
*A61B 5/16* (2006.01)
(Continued)

(52) U.S. Cl.
CPC ......... *A61B 5/165* (2013.01); *G06Q 30/0269* (2013.01); *G10L 25/63* (2013.01); (Continued)

(58) Field of Classification Search
None
See application file for complete search history.

(56) References Cited

U.S. PATENT DOCUMENTS 5,243,517 A    9/1993    Schmidt et al.
5,676,138 A    10/1997   Zawilinski
(Continued)

FOREIGN PATENT DOCUMENTS

EP    2579169       4/2013
WO    2008004181    1/2008
WO    2016109553    7/2016

OTHER PUBLICATIONS

IP.com Search Strategy dated Jul. 15, 2021 (Year: 2021).*

(Continued)

*Primary Examiner* — Matthew T Sittner
(74) *Attorney, Agent, or Firm* — Hanley, Flight & Zimmerman, LLC

(57) ABSTRACT

Methods and apparatus to identify an emotion evoked by media are disclosed. An example apparatus includes a synthesizer to generate a first synthesized sample based on a pre-verbal utterance associated with a first emotion. A feature extractor is to identify a first value of a first feature of the first synthesized sample. The feature extractor to identify a second value of the first feature of first media evoking an unknown emotion. A classification engine is to create a model based on the first feature. The model is to establish a relationship between the first value of the first feature and the first emotion. The classification engine is to identify the first media as evoking the first emotion when the model indicates that the second value corresponds to the first value.

18 Claims, 54 Drawing Sheets

Related U.S. Application Data continuation of application No. 14/457,846, filed on Aug. 12, 2014, now Pat. No. 9,788,777.

(60) Provisional application No. 61/978,704, filed on Apr. 11, 2014, provisional application No. 61/948,225, filed on Mar. 5, 2014, provisional application No. 61/948,221, filed on Mar. 5, 2014, provisional application No. 61/934,862, filed on Feb. 3, 2014, provisional application No. 61/934,662, filed on Jan. 31, 2014, provisional application No. 61/882,672, filed on Sep. 26, 2013, provisional application No. 61/882,676, filed on Sep. 26, 2013, provisional application No. 61/865,052, filed on Aug. 12, 2013, provisional application No. 61/882,668, filed on Sep. 26, 2013.

(51) Int. Cl.
    *G06Q 30/02*    (2012.01)
    *G10L 25/63*    (2013.01)
    *A61B 5/11*     (2006.01)
    *A61B 5/00*     (2006.01)

(52) U.S. Cl.
    CPC ............ *A61B 5/1112* (2013.01); *A61B 5/1123* (2013.01); *A61B 5/4803* (2013.01)

(56) References Cited

U.S. PATENT DOCUMENTS

| | | | |
|---|---|---|---|
| 6,212,502 | B1 | 4/2001 | Ball et al. |
| 6,520,905 | B1 | 2/2003 | Surve et al. |
| 7,698,238 | B2 | 4/2010 | Barletta et al. |
| 7,921,067 | B2 | 4/2011 | Kemp et al. |
| 8,373,768 | B2 | 2/2013 | Bill |
| 8,671,068 | B2 | 3/2014 | Harber et al. |
| 9,788,777 | B1 | 10/2017 | Knight et al. |
| 10,806,388 | B2 | 10/2020 | Knight et al. |
| 2001/0021907 | A1 | 9/2001 | Shimakawa et al. |
| 2003/0028383 | A1 | 2/2003 | Guerin et al. |
| 2004/0019484 | A1 | 1/2004 | Kobayashi et al. |
| 2004/0128286 | A1 | 7/2004 | Yasushi et al. |
| 2005/0261032 | A1 | 11/2005 | Seo et al. |
| 2006/0212478 | A1 | 9/2006 | Plastina et al. |
| 2006/0224385 | A1 | 10/2006 | Seppala |
| 2007/0033050 | A1 | 2/2007 | Asano et al. |
| 2007/0074619 | A1 | 4/2007 | Vergo |
| 2007/0221044 | A1 | 9/2007 | Orr |
| 2008/0077277 | A1 | 3/2008 | Park et al. |
| 2008/0091512 | A1 | 4/2008 | Marci et al. |
| 2008/0201144 | A1* | 8/2008 | Song ............... G06V 40/171 704/236 |
| 2008/0201370 | A1* | 8/2008 | Kemp ............... G06F 16/68 |
| 2009/0024666 | A1 | 1/2009 | Wang et al. |
| 2009/0234888 | A1 | 9/2009 | Holmes et al. |
| 2009/0265170 | A1 | 10/2009 | Irie et al. |
| 2010/0011388 | A1 | 1/2010 | Bull et al. |
| 2010/0024630 | A1 | 2/2010 | Teie |
| 2010/0191037 | A1 | 7/2010 | Cohen et al. |
| 2010/0217595 | A1 | 8/2010 | Kim et al. |
| 2010/0251147 | A1 | 9/2010 | Donovan et al. |
| 2010/0325135 | A1 | 12/2010 | Chen et al. |
| 2011/0004577 | A1 | 1/2011 | Jung et al. |
| 2011/0020778 | A1 | 1/2011 | Forbes |
| 2011/0125763 | A1 | 5/2011 | Takanen et al. |
| 2011/0214141 | A1 | 9/2011 | Oyaizu |
| 2011/0289075 | A1 | 11/2011 | Nelson |
| 2012/0016208 | A1 | 1/2012 | Janssen et al. |
| 2012/0016822 | A1 | 1/2012 | Kobayashi |
| 2012/0041917 | A1 | 2/2012 | Newton et al. |
| 2012/0102066 | A1 | 4/2012 | Eronen et al. |
| 2012/0143693 | A1 | 6/2012 | Chung et al. |
| 2012/0226706 | A1 | 9/2012 | Choi et al. |
| 2013/0117020 | A1 | 5/2013 | Chung et al. |
| 2013/0345840 | A1 | 12/2013 | Lempel et al. |
| 2014/0025620 | A1 | 1/2014 | Greenzeiger et al. |
| 2014/0330848 | A1 | 11/2014 | Chen et al. |
| 2016/0196105 | A1 | 7/2016 | Vartakavi et al. |
| 2018/0049688 | A1 | 2/2018 | Knight et al. |

OTHER PUBLICATIONS

STIC EIC 3600 Search Report for parent U.S. Appl. No. 15/785,050 (Similar claims) dated Mar. 6, 2020. (Year: 2020).*

United States Patent and Trademark Office, "Notice of Allowance and Fee(s) Due" issued in connection with U.S. Appl. No. 15/785,050 dated Jun. 16, 2020, 9 pages.

United States Patent and Trademark Office, "Non-Final Office Action" issued in connection with U.S. Appl. No. 15/785,050 dated Feb. 10, 2020, 13 pages.

United States Patent and Trademark Office, "Restriction and/or Election Requirement" issued in connection with U.S. Appl. No. 15/785,050 dated Oct. 25, 2019, 5 pages.

STIC EIC 3600 Search Report for U.S. Appl. No. 15/785,050, dated Mar. 6, 2020.

United States Patent and Trademark Office, "Restriction and/or Election Requirement" issued in connection with U.S. Appl. No. 14/457,846 dated Oct. 26, 2016, 8 pages.

United States Patent and Trademark Office, "Non-Final Office Action" issued in connection with U.S. Appl. No. 14/457,846 dated Feb. 1, 2017, 20 pages.

United States Patent and Trademark Office, "Notice of Allowance and Fee(s) Due" issued in connection with U.S. Appl. No. 14/457,846 dated Jun. 9, 2017, 11 pages.

International Searching Authority, "Written Opinion", issued in connection with International Application Serial No. PCT/US2015/067889, dated Mar. 25, 2016, 8 pages.

International Searching Authority, "International Search Report", issued in connection with International Application Serial No. PCT/US2015/067889, dated Mar. 25, 2016, 2 pages.

Wikipedia, "PAD Emotional state model", Retrieved from the Internet: URL: https://en.wikipedia.org/wiki/PAD_emotional_state_model, Accessed on Nov. 11, 2015, 3 pages.

Borghini et al., "Measuring neurophysiological signals in aircraft pilots and car drivers for the assessment of mental workload, fatigue and drowsiness", Neuroscience and Biobehavioral Reviews 44, 2014, 18 pages.

Fairclough et al., "A metabolic measure of mental effort", Retrieved from the Internet: URL: http://physiologicalcomputing.org/wp-content/uploads/2015/03/faircloughho-uston041.pdf, Oct. 9, 2003, 14 pages.

Hu et al., "Improving Mood Classification in Music Digital Libraries by Combining Lyrics and Audio", Association of Computing Machinery, JCDL '10 proceedings of the 10th annual joint conference on Digital libraries, Retrieved from the Internet: URL: http://www.music-ir.org/archive/papers/jcdl2011_Improving-mood-classification.pdf>, Jun. 2010, 10 pages.

Liu et al. "Listen to your Heart: Stress Prediction Using Consumer Heart Rate Sensors", Retrieved from the Internet: URL: http://cs229.standord.edu/proj2013/LiuUlrich-ListenToYoutHeart-StressPredictionUsingConsumerHeartRateSensors.pdf, Autumn 2013-2014, 5 pages.

Renneker, Will, "The Effects of Calming and Exciting Music on Galvanic Skin Response and Cognition", Retrieved from the Internet: URL: http://webs.wofford.edu/pittmandw/psy330/exps/2010/WR2.htm, Accessed on Oct. 28, 2015, 6 pages.

Rowe et al., "Heart Rate Variability: Indicator of User State as an Aid to Human-Computer Interaction" Retrieved from the Internet: http://www.labs.iro.umontreal.ca/.about.blanhae/papers/physiologie/Heart%-20Rate%variability%20%20indicator%20of%20user%20state%20as%20an%aid%to%HCI-.pdf, Apr. 1998, 8 pages.

Sullivan et al., "A Low-Noise, Non-Contact EEG/ECG Sensor", IEEE, Retrieved from the Internet: URL: http://isn.ucsd.edu/pubs/biocas07_eeg.pdf, 2007, 4 pages.

The Local, "New mobile tech makes music to suit moods", Retrieved from the Internet: URL: http://www.thelocal.no/20141114/new-

(56) References Cited

OTHER PUBLICATIONS mobile-tech-makes-music-to-suit-moods-, Nov. 17, 2014, 2 pages.

Cox, Trevor, "Roughness", University of Salform Manchester, Retrieved from the Internet: URL: http://www.acoustics.salform.ac.uk/coustics_info/sound_quality/?content, Mar. 21, 2014, 3 pages.

Gerhard, David, "Automatic Interval Naming Using Relative Pitch", School of Computing Science, Simon Fraser University, May 16, 2014, 11 pages.

Lu, et al., "A Technique towards Automatic Audio Classification and Retrieval", Gippsland School of Computing and Information Technology, Monash University, 1998, 4 pages.

Owen Craigie Meyers, "A Mood-Based Music Classification and Exploration System", School of Architecture and Planning, Massachusetts Institute of Technology, Jun. 2007, 93 pages.

Peeters, Geoffroy, "A Large Set of Audio Features for Sound Description", Apr. 23, 2004, 25 pages.

Peeters, Geoffroy, "Chroma-based estimation of musical key from audio-signal analysis", Ircam-Sound Analysis/Synthesis Team, 2006, 6 pages.

West, Kris, "Mirex Audio Genre Classification", School of Computing Sciences, University of East Anglia, 2005, 3 pages.

Wikipedia, "Brightness", Retrieved from the Internet: URL: http://en.wikipedia.org/w/index.php?title=Brightness&oldid=543629699, Mar. 12, 2013, 2 pages.

Wikipedia, "Spectral Flatness", Retrieved from the Internet: URL: http://en.wikipedia.org/w/index.php?title=Spectral_flatness&oldid=5866574- 51, Dec. 18, 2013, 2 pages.

\* cited by examiner

FIG. 15B

| EMOTION | ZERO CROSSINGS | ZERO CROSSING WEIGHT | ROLLOFF POWER | ROLLOFF POWER WEIGHT | BRIGHTNESS | BRIGHTNESS WEIGHT | FLATNESS | FLATNESS WEIGHT | MINOR THIRD INTERVALS | MINOR THIRD INTERVALS WEIGHT |
|---|---|---|---|---|---|---|---|---|---|---|
| JOY | 800 Hz | 15 | 85% | .04 | 53% | .08 | .6 | .05 | .2 | .1 |
| ANGER | 1400 Hz | 10 | 90% | .8 | 82% | .9 | .1 | .8 | .3 | 0 |
| SADNESS | 950 Hz | 20 | 61% | .5 | 32% | .4 | .3 | .9 | .8 | .6 |
| ⋮ | ⋮ | ⋮ | ⋮ | ⋮ | ⋮ | ⋮ | ⋮ | ⋮ | ⋮ | ⋮ |

| MAJOR THIRD INTERVALS | MAJOR THIRD INTERVAL WEIGHT | IRREGULARITY | IRREGULARITY WEIGHT | CHROMA | CHROMA WEIGHT | MAIN PITCH | MAIN PITCH WEIGHT | KEY | KEY WEIGHT |
|---|---|---|---|---|---|---|---|---|---|
| .8 | .05 | .3 | .03 | X | .1 | E | .3 | C MAJOR | .2 |
| .3 | .6 | .9 | .7 | Y | .4 | G | .6 | G MAJOR | .1 |
| .2 | .2 | .5 | .9 | Z | .2 | F# | .7 | F# MINOR | .6 |
| ⋮ | ⋮ | ⋮ | ⋮ | ⋮ | ⋮ | ⋮ | ⋮ | ⋮ | ⋮ |

| 1810 | 1812 ↓ HAPPY | 1814 ↓ SAD | 1816 ↓ JOYFUL |
|---|---|---|---|
| DESIRED EMOTION | 8 | 2 | 5 |

| 1820 | 1822 ↓ HAPPY | 1824 ↓ SAD | 1826 ↓ JOYFUL | 1828 ↓ EMOTION DISTANCE |
|---|---|---|---|---|
| MEDIA | | | | |
| 1830 → MEDIA A | 7.2 | 2.8 | 6.2 | 2.8 |
| 1832 → MEDIA B | 6.2 | 3.8 | 2.1 | 6.5 |
| 1834 → MEDIA C | 3.6 | 6.4 | 1.0 | 12.8 |

FIG. 18

| | FEATURE | REFERENCE VALUE (JOY) | VALUE OF INSTANT MEDIA | DIFFERENCE | WEIGHT | FEATURE SCORE |
|---|---|---|---|---|---|---|
| 2585 | ZERO CROSSINGS | 800 | 810 | 10 | 15 | 1.50 |
| 2586 | ROLLOFF POWER | .85 | .82 | .03 | .04 | 1.33 |
| 2587 | BRIGHTNESS | .53 | .6 | .07 | .08 | 1.14 |
| 2588 | FLATNESS | .6 | .5 | .1 | .05 | 0.50 |
| 2589 | MINOR THIRD INTERVALS | .2 | .3 | .1 | .1 | 1.00 |
| 2590 | MAJOR THIRD INTERVALS | .8 | .75 | .05 | .03 | 0.60 |
| 2591 | IRREGULARITY | .3 | .25 | .05 | .03 | 0.60 |
| 2592 | CHROMA | X | X' | .1 | .1 | 1.00 |
| 2593 | MAIN PITCH | E | C | 4 SEMITONES | .3 | 0.08 |
| 2594 | KEY | C MAJOR | C MINOR | .2 | .2 | 1 |

FIG. 25A

EMOTION SCORE
SUM = 8.75

| 3950 | HAPPY (3952) | SAD (3954) | JOYFUL (3956) | CONTEXT (INDOORS) (3958) | ACTIVITY (WORKOUT) (3960) |
|---|---|---|---|---|---|
| DESIRED EMOTION | 8 | 2 | 5 | 9.2 | 8.9 |

| 3970 / MEDIA | HAPPY (3982) | SAD (3984) | JOYFUL (3986) | CONTEXT (INDOORS) (3988) | ACTIVITY (WORKOUT) (3990) | EMOTION DISTANCE (3992) |
|---|---|---|---|---|---|---|
| MEDIA A (3972) | 7.2 | 2.8 | 6.2 | 2.4 | 3.8 | 14.7 |
| MEDIA B (3974) | 6.2 | 3.8 | 2.1 | 8.9 | 7.8 | 7.9 |
| MEDIA C (3976) | 3.6 | 6.4 | 1.0 | 2.4 | 3.8 | 24.7 |

FIG. 39A

METHODS AND APPARATUS TO IDENTIFY A MOOD OF MEDIA

RELATED APPLICATIONS

This patent arises from a continuation of Ser. No. 15/785,050, which was filed on Oct. 16, 2017, and was entitled "METHODS AND APPARATUS TO IDENTIFY A MOOD OF MEDIA", which is a continuation of Ser. No. 14/457,846, which was filed on Aug. 12, 2014, and was entitled "METHODS AND APPARATUS TO IDENTIFY A MOOD OF MEDIA", which claims priority to U.S. Provisional Patent Application Ser. No. 61/865,052, which was filed on Aug. 12, 2013, U.S. Provisional Patent Application Ser. No. 61/882,668, which was filed on Sep. 26, 2013, U.S. Provisional Patent Application Ser. No. 61/882,672, which was filed on Sep. 26, 2013, U.S. Provisional Patent Application Ser. No. 61/882,676, which was filed on Sep. 26, 2013, U.S. Provisional Patent Application Ser. No. 61/934,662, which was filed on Jan. 31, 2014, U.S. Provisional Patent Application Ser. No. 61/934,862, which was filed on Feb. 3, 2014, U.S. Provisional Patent Application Ser. No. 61/948,221, which was filed on Mar. 5, 2014, U.S. Provisional Patent Application Ser. No. 61/948,225, which was filed on Mar. 5, 2014, and U.S. Provisional Patent Application Ser. No. 61/978,704, which was filed on Apr. 11, 2014. U.S. patent application Ser. Nos. 14/457,846 and 15/785,050, and U.S. Provisional Patent Application Ser. Nos. 61/865,052, 61/882,668, 61/882,672, 61/882,676, 61/934,662, 61/934,862, 61/948,221, 61/948,225, and 61/978,704 are hereby incorporated by reference in their entireties.

FIELD OF THE DISCLOSURE

This disclosure relates generally to media classification, and, more particularly, to methods and apparatus to identify a mood of media.

BACKGROUND

Understanding characteristics of media such as music, movies, television programming, advertisements, etc. is presently largely driven by subjective measures. Subjective measures include, for example, how the audio of a particular piece of media sounds to a particular listener. Metadata may include, for example, a description of a genre, an artist, a performer, an actor, a musician, a band, an instrument, etc. Such metadata may itself involve subjective measures which were used to generate the metadata (e.g., comedy, action, drama, etc.) Current mechanisms for identifying subjective media characteristics are limited.

BRIEF DESCRIPTION OF THE DRAWINGS

FIGS. 15A, 15B, and 15C illustrate example data tables representing an association of identified audio features with a particular emotion.

FIG. 18 illustrates example data tables that may be considered by the example media selector of the example recommendation engine of FIGS. 1 and/or 16 when selecting media for recommendation.

FIG. 25A illustrates an example data table that may be used to calculate an emotional intensity score.

FIG. 39A illustrates an example data table that may be considered by the example media selector of the example recommendation engine of FIGS. 1 and/or 16 when selecting media for recommendation based at least in part on a context and/or an activity of a user.

The figures are not to scale. Wherever possible, the same reference numbers will be used throughout the drawing(s) and accompanying written description to refer to the same or like parts.

DETAILED DESCRIPTION

Figure 1:
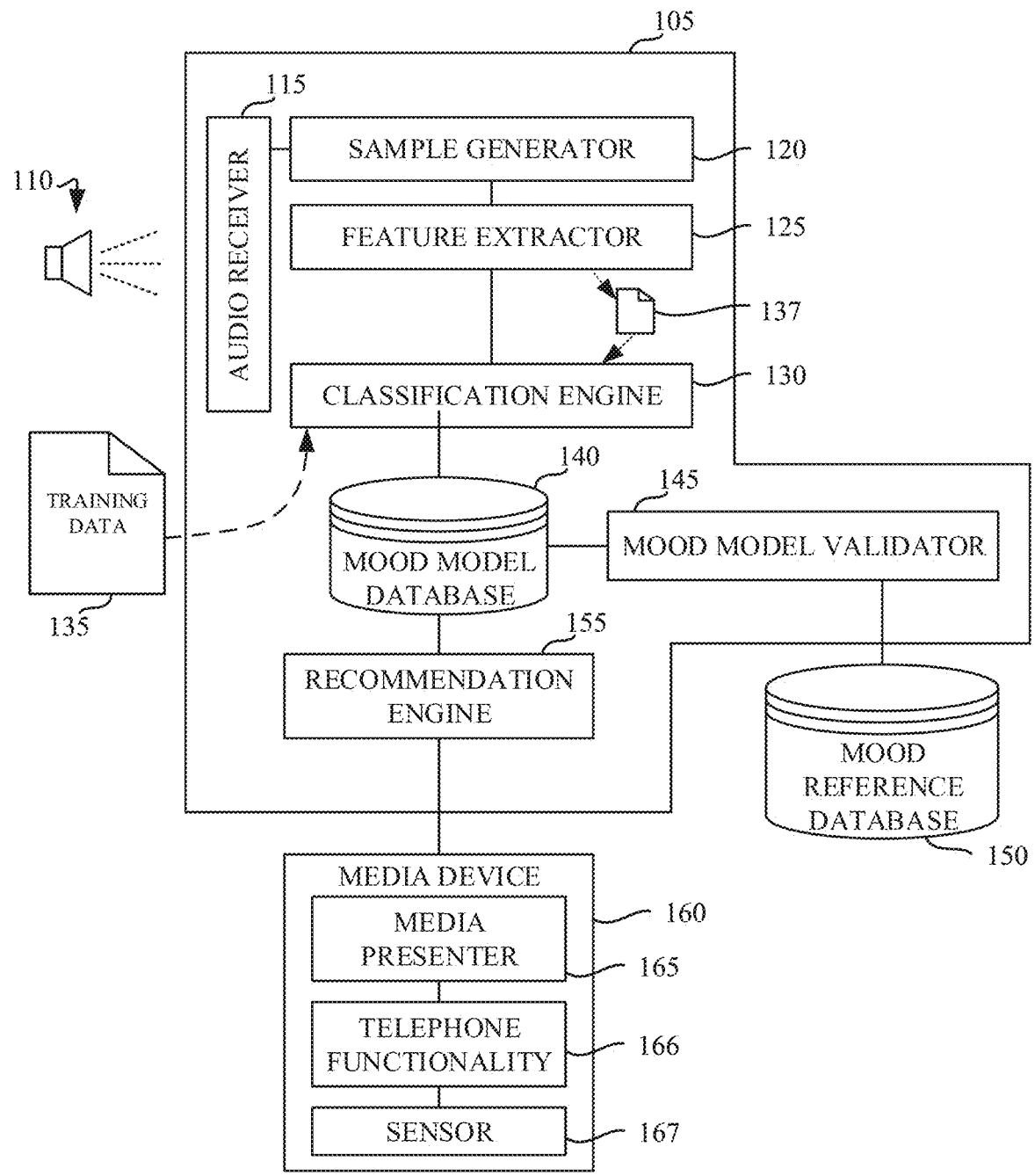
FIG. 1 is an example mood-based media identification and/or recommendation system constructed in accordance with the teachings of this disclosure to identify a mood of media.

Disclosed herein are methods, apparatus, and systems that understand and/or identify emotions that are conveyed by media. In disclosed examples, the emotion classification or identifications predict emotions evoked in human subjects based on media (e.g., music, advertisements, entertainment and/or other stimuli to which the subject was exposed). In some examples, the emotion predictions are based on the media without consideration of other metadata or proxies such as, for example, activity, artist, performer, genre, and/or demographic. Example classification and prediction systems and methods disclosed herein are based on several principles of behavior and/or neuroscience including (a) music is universal across cultures, (b) emotions are universal across cultures (c) emotions may be analyzed as a core set of emotions and secondary emotions, and (d) human voice conveys the core emotional spectro-temporal features present in music. Many different emotions exist. As used herein, an emotion is an instinctive or intuitive feeling as distinguished from reasoning or knowledge. Example emotions include, for example, joy, sadness, peace, anger, courage, fear, desire, disgust, etc. As used herein, a mood represents one or more emotions experienced for an extended time period (e.g., minutes, hours, days, etc.).

Known systems attempt to identify emotions in media by using a pre-classified set of media (e.g., sad music, happy music, romantic music, etc.) as a training set. Typically, such systems focus on audio. Such known systems place a large emphasis of the classification on commercial pre-recorded music and its subjective pre-categorization. Based on the pre-classified music, known systems attempt to apply machine learning and pattern recognition algorithms to an unknown piece of music to identify an emotion. However, this approach is error prone and often results in identification of an incorrect emotion. For example, while an entire piece of music may generally be sad (e.g., Miles Davis' "Kind of Blue" album), there may be parts of the music that are happy. Such misclassification may result in an exuberant section of music being classified as sad. Such misclassification can result in erroneous selection of media when trying to match media to a desired mood.

In some examples disclosed herein, pre-verbal expressions of human emotion are used as a training set to increase the accuracy of an emotion identification system. In some such examples, pre-verbal utterances are used as the training set for a model that may subsequently be used to autonomously classify media. In some such examples, pre-verbal utterances are classified as having a particular emotion. A pre-verbal utterance is defined to be a short duration, language independent, utterance (e.g., a half second, two seconds, five seconds, etc.) that conveys emotion, not words. Such a pre-verbal utterance acts as a basic building block or phoneme of emotion. For example, when a scream is heard (e.g., in the middle of the night), the scream is unambiguously registered by the human brain as an expression of fear. When sobbing is heard, it is unmistakably associated with sorrow. When raucous laughter is heard, it is easily associated by the human brain with humor. These associations are recognized across cultures. Pre-verbal utterances provide a more accurate and reliable tool for classifying media than purely training on subjective classifications, composed music, and/or metadata tags of music. Further, using such pre-verbal utterances to build a classification model results in a model with greater scalability, applicability, and/or extendibility than traditional models.

While pre-verbal utterances are generally cross-cultural, in some examples, the association of an emotion with a particular pre-verbal utterance may be modified or altered to suit a particular cultural region, a particular geographic region, etc.

In some examples, using samples of pre-verbal expressions and/or other samples identified as evoking a particular emotion, a feature extractor extracts features of the samples. In some examples, the extracted features are used by a classification engine to create a model that maps emotion(s) to corresponding features of pre-verbal expression(s). Once the model (e.g., a classification engine) is created, it may be used to automatically classify the emotion(s) present in a sampled media (e.g., unknown media) and/or to classify the mood of the media. In some examples, a recommendation engine 155 utilizes the classification engine to provide media recommendations to a user.

As used herein, the term "media" includes any type of content and/or advertisement delivered via any type of distribution medium. Thus, media includes television programming or advertisements, radio programming or advertisements, movies, web sites, streaming media, call hold music, ringtones, etc.

Example methods, apparatus, and articles of manufacture disclosed herein monitor media presentations and provide recommendations for media presentations at media devices. Such media devices may include, for example, Internet-enabled televisions (e.g., smart TVs), personal computers, Internet-enabled mobile handsets (e.g., a smartphone), video game consoles (e.g., Xbox®, PlayStation®), tablet computers (e.g., an iPad®), digital media players (e.g., a Roku® media player, a Slingbox®, etc.), etc. In some examples, media monitoring information is aggregated across multiple persons, devices, and/or media to determine emotion and/or mood-based information associated with users, media, and/or media devices. In examples disclosed herein, monitoring information includes, but is not limited to, media identifying information (e.g., media-identifying metadata, codes, signatures, watermarks, closed captioning information, subtitle track information, and/or other information that may be used to identify presented media), application usage information (e.g., an identifier of an application, a time and/or duration of use of the application, a rating of the application, etc.), user mood and/or emotion data, device type identifier, and/or user-identifying information (e.g., demographic information, a user identifier, a panelist identifier, a username, etc.).

In some examples disclosed herein, media is identified using metadata associated with the media (e.g., an ID3 tag comprising media-identifying information, etc. as disclosed in U.S. patent application Ser. No. 13/443,596, which is hereby incorporated herein by reference). However, in some examples, other media identification techniques may be used to identify the media. For example codes and/or signatures may be used to identify the media. Once media has been identified, recommendations concerning other media to be presented to a user may be generated based on a mood and/or emotion of the identified media (which emotion and/or mood may be known and/or identified using techniques described herein).

Audio watermarking is a technique used to identify media such as television broadcasts, radio broadcasts, advertisements (e.g., television, Internet, and/or radio advertisements), downloaded media, streaming media, prepackaged media, etc. Existing audio watermarking techniques identify media by embedding one or more audio codes (e.g., one or more watermarks), such as media identifying information and/or an identifier that may be mapped to media identifying information, into an audio and/or video component of the carrier media. In some examples, the audio or video component is selected to have a signal characteristic sufficient to hide the watermark (e.g., psychoacoustic encoding). As used herein, the terms "code" or "watermark" are used interchangeably and are defined to mean any identification information (e.g., an identifier) that may be transmitted with, inserted in, and/or embedded in the audio or video of media (e.g., a program or advertisement) for the purpose of identifying the media or for another purpose such as tuning (e.g., a packet identifying header). As used herein "media" refers to audio and/or visual (still or moving) content and/or advertisements. To identify watermarked media, the watermark(s) are extracted and used to access a table of reference watermarks that are mapped to media identifying information.

Unlike media monitoring techniques based on codes and/or watermarks included with and/or embedded in the monitored media, fingerprint or signature-based media monitoring techniques generally use one or more inherent characteristics of the monitored media during a monitoring time interval to generate a substantially unique proxy for the media. Such a proxy is referred to as a signature or fingerprint, and can take any form (e.g., a series of digital values, a waveform, etc.) representative of any aspect(s) of the media signal(s)(e.g., the audio and/or video signals forming the media presentation being monitored). A good signature is one that is repeatable when processing the same media presentation, but that is unique relative to other (e.g., different) presentations of other (e.g., different) media. Accordingly, the term "fingerprint" and "signature" are used interchangeably herein and are defined herein to mean a proxy for identifying media that is generated from one or more inherent characteristics of the media.

Signature-based media monitoring generally involves determining (e.g., generating and/or collecting) signature(s) representative of a media signal (e.g., an audio signal and/or a video signal) output by a monitored media device and comparing the monitored signature(s) to one or more references signatures corresponding to known (e.g., reference) media sources. Various comparison criteria, such as a cross-correlation value, a Hamming distance, etc., can be evaluated to determine whether a monitored signature matches a particular reference signature. When a match between the monitored signature and one of the reference signatures is found, the monitored media can be identified as corresponding to the particular reference media represented by the reference signature that matched the monitored signature. Because attributes, such as an identifier of the media, a presentation time, a broadcast channel, etc., are collected for the reference signature, these attributes may then be associated with the monitored media whose monitored signature matched the reference signature. Example systems for identifying media based on codes and/or signatures are long known and were first disclosed in Thomas, U.S. Pat. No. 5,481,294, which is hereby incorporated by reference in its entirety.

The monitored users (i.e., panelists) are users registered on panels maintained by a ratings entity (e.g., an audience measurement company) that owns and/or operates the ratings entity subsystem. Traditionally, audience measurement entities (also referred to herein as "ratings entities") determine demographic reach for advertising and media programming based on registered panel members. That is, an audience measurement entity enrolls people that consent to being monitored into a panel. During enrollment, the audience measurement entity receives demographic information from the enrolling people so that subsequent correlations may be made between advertisement/media exposure to those panelists and different demographic markets.

People become panelists via, for example, a user interface presented on the media device 102 (e.g., via a website). People become panelists in additional or alternative manners such as, for example, via a telephone interview, by completing an online survey, etc. Additionally or alternatively, people may be contacted and/or enlisted using any desired methodology (e.g., random selection, statistical selection, phone solicitations, Internet advertisements, surveys, advertisements in shopping malls, product packaging, etc.).

FIG. 1 illustrates an example mood-based media identification and/or recommendation system 105 constructed in accordance with the teachings of this disclosure to identify emotions of segments of media and/or an overall mood of the media. The example mood identification system of FIG. 1 includes an audio receiver 115, a sample generator 120, a feature extractor 125, a classification engine 130, a mood model database 140, a mood model validator 145, and a recommendation engine 155. The example audio receiver 115 of the illustrated example receives audio from an audio source 110. In the example of FIG. 1, the audio is sampled by a sample generator 120. The samples output by the sample generator 120 are processed by the feature extractor 125 to identify features. In the example of FIG. 1, the features are communicated to the classification engine 130. The example classification engine 130 of FIG. 1 applies a mood classification model employing mood classification rules to classify the mood of the received audio.

The example classification engine 130 of FIG. 1 receives mood training data 135 and creates the mood classification rules underlying the model stored in the example mood model database 140. To validate the mood classification rules, the example mood model validator 145 of the illustrated example interfaces with a mood reference database 150. The example recommendation engine 155 of FIG. 1 interfaces with a media presenter 165 of a media device 160 to offer suggestions of other emotion and/or mood appropriate media to the user.

The example audio source 110 of the illustrated example of FIG. 1 is implemented by a media playback device having a speaker playing media. However, the example audio source 110 may be implemented in any other fashion. For example, the audio source may be implemented by a musician singing and/or playing a musical instrument, or a subject making a pre-verbal utterance(s).

In some examples, the media played by the audio source 110 is implemented as a pre-recorded audio file such as, for example, a Waveform Audio File (WAV) file, a Free Lossless Audio Codes (FLAC) file, an MPEG-2 audio layer 3 (MP3) file, etc. In some examples, in order to build the mood model, the audio source 110 presents pre-verbal utterances to the audio receiver 115 (e.g., recorded media or live sounds (in which case the audio source may be implemented by a human, a nature sound, and/or an animal)). However, any type of media and/or audio may additionally or alternatively be presented for building the model such as, for example, live music, recorded music, a subject making a pre-verbal utterance(s), etc.

The example audio receiver 115 of the illustrated example of FIG. 1 is implemented by a microphone. However, the audio receiver 115 may be implemented in any other fashion. In the illustrated example, the audio receiver 115 receives and forwards audio from the audio source 110 to the example sample generator 120. In some examples, the audio receiver 115 reads pre-recorded audio from a memory such as, for example, a hard disk drive, a solid state memory device, etc.

The example sample generator 120 of the illustrated example of FIG. 1 is implemented by a logic circuit such as a silicon-based processor executing instructions, but it could additionally or alternatively be implemented by an application specific integrated circuit(s) (ASIC(s)), programmable logic device(s) (PLD(s)) and/or field programmable logic device(s) (FPLD(s) (e.g., a field programmable gate array (FPGA))), an analog circuit, and/or other circuitry. As used herein, a sample refers to a sequence of discrete values representing an audio signal taken at different points in time. As used herein, a sample may represent any duration of audio (e.g., ten seconds, one second, a fraction of a second, thirty seconds, etc.). In the illustrated example, the sample generator 120 receives first audio from the audio receiver (e.g., a pre-verbal utterance, a music recording, etc.) and creates one or more digital audio samples based on the first audio. Although the following speaks in terms of digital sampling, analog techniques could additionally or alternatively be employed.

The example feature extractor 125 of the illustrated example of FIG. 1 is implemented by a logic circuit such as a silicon-based processor executing instructions, but it could additionally or alternatively be implemented by an ASIC(s), a PLD(s), a FPLD(s), an analog circuit, and/or other circuitry. The example feature extractor 125 accesses the audio samples of the sample generator 120. The example feature extractor 125 of FIG. 1 processes the received samples to identify one or more features of the samples such as, for example, zero crossings, rolloff power, brightness, flatness, roughness, minor third interval power, major third interval power, irregularity, chroma, main pitch, a key, etc. In examples disclosed herein, the example feature extractor 125 computes new values for each feature at discrete time intervals (e.g., every ten milliseconds, every two hundred milliseconds, every second, etc.). In some examples, two or more of the features are used. In other examples, three or more of such features are employed. In some examples, temporal features are extracted using specialized wavelets. Wavelet based sets can capture core structures in rhythms. Example wavelets include Daubechies wavelets, Marr wavelets, etc. In some examples, new wavelets may be used to accurately capture and/or otherwise extract rhythmic structures of music. The output of the feature extractor 125 is transmitted to the classification engine 130.

The example classification engine 130 of the illustrated example of FIG. 1 is implemented by a logic circuit such as a silicon-based processor executing instructions, but it could additionally or alternatively be implemented by an ASIC(s), a PLD(s), a FPLD(s), an analog circuit, and/or other circuitry. The example classification engine 130 of this example utilizes the training data 135 and/or features extracted from samples associated with the training data 135 and/or other training data input via the audio receiver 115 to generate a mood model. In the illustrated example, the mood model is stored in the mood model database 140. In examples disclosed herein, one or more mood models are used to classify media such as audio (e.g., music) as associated with one or more different emotions and/or moods based on attributes extracted by the feature extractor 125. In the illustrated example, the mood model(s) are implemented by an artificial neural network (ANN). However, in some examples, the mood model(s) are algorithm(s) such as, for example, a naïve-Bayesian algorithm, hierarchical Bayesian clustering algorithm, linear regression algorithms, non-linear regression algorithms, Support Vector Machines, etc. In some examples, additional constraints are added to the classification model. For example, some emotions are opposite of each other and do not appear at the same time (e.g., anger is the opposite of peace). Thus, in some examples, the classification engine 130 will not build a model that simultaneously classifies media as exhibiting two opposing emotional states (e.g., at substantially the same time). Other examples release this constraint. In the illustrated example, interactions of the classified emotions are used to guide the classification model. For example, fear and courage are a couplet defining a negative emotional value through a positive emotional value. Other example emotional couplets include, for example, joy and sadness, peace and anger, desire and disgust, etc.

In some examples, fuzzy logic models that can identify co-existence of different emotions are used. Some such fuzzy logic models may ignore that some emotions are completely independent or mutually exclusive. For example, the fuzzy logic model may indicate that there can be sadness and courage evoked at the same time.

In the example illustrated, the example classification engine 130 processes unknown audio (e.g., previously unclassified audio) to identify emotion(s) and/or mood(s) associated therewith based on the model. The example classification engine 130 of FIG. 1 creates a second by second classification of the emotion(s) of the audio. In some examples, different window sizes are used (e.g., a five second window, a ten second window, etc.). In some examples, a moving window is used. In some examples, the windows overlap. In others, the windows do not overlap. In some examples, a fuzzy weighted composition of multiple data points to a single identification per window (for example, every ten seconds) is used.

The example training data 135 of the illustrated example of FIG. 1 provides initial metrics (e.g., classification data with known emotion(s) and/or mood(s) labeled therein) to be used by the classification engine 130 when creating the mood model. In the illustrated example, the example training data 135 identifies a particular sample or group of samples (e.g., media such as pre-recorded music, pre-verbal utterances, etc.) as evoking one or more known emotion(s) such as, for example, joy, sadness, peace, anger, courage, fear, desire, disgust, etc. In some examples, the training set includes samples evoking multiple emotions at the same time. In other examples, the sample(s) are aligned with only one emotion. In some examples, the training set is tagged as indicative of different emotions based on a survey based assessment from one or more individuals. In some examples, the training data indicates an intensity of a given emotion and/or mood. In examples disclosed herein, an emotional intensity and/or emotion score is representative of an intensity of a given emotion. In examples disclosed herein, emotional intensity is rated on a scale of zero to ten (0-10). However, any other scale may additionally or alternatively be used. In some examples, first media is classified as being highly correlated with happiness (e.g., a happiness score of 9.9), whereas second media is classified as being correlated with happiness, but to a lesser extent than the first media (e.g., receiving a happiness score of 5.7). In some examples, neurophysiological testing is used to assess whether an emotion is evoked by a sample. In the illustrated example, the example training data 135 is implemented using a tabular format. However, any other format of training data may additionally or alternatively be used. For example, the training data may be represented using an extensible markup language (XML) file.

In some examples, the example feature extractor 125 extracts features from a pre-verbal utterance training set 137. In the illustrated example of FIG. 1, the pre-verbal utterance training set 137 provides initial metrics (e.g., classification data with known emotional classification(s)) to be used by the classification engine 130 when creating the mood model (e.g., based on the pre-verbal utterances). In the illustrated example, the pre-verbal utterance training set 137 identifies various pre-verbal utterances and/or samples based on those pre-verbal utterances as evoking emotions such as, for example, joy, sadness, peace, anger, courage, fear, desire, disgust, etc. In the illustrated example, the example pre-verbal utterance training set 137 is implemented using a tabular format. However, any other format of training data may additionally or alternatively be used. For example, the pre-verbal utterance training set 137 may be represented using an extensible markup language (XML) file.

The example mood model database 140 of the illustrated example of FIG. 1 is implemented by a database for storing the mood model and/or other mood classification information. The example mood model database 140 of FIG. 1 and/or any other database described in this disclosure may be implemented by any memory, storage device and/or storage disc for storing data such as, for example, flash memory, magnetic media, optical media, etc. Furthermore, the data stored in the mood model database 140 may be in any data format such as, for example, binary data, comma delimited data, tab delimited data, structured query language (SQL) structures, etc. While in the illustrated example the mood model database 140 is illustrated as a single database, the mood model database 140 and/or any other database described herein may be implemented by any number and/or type(s) of databases.

The example mood model validator 145 of the illustrated example of FIG. 1 is implemented by a logic circuit such as a silicon-based processor executing instructions, but it could additionally or alternatively be implemented by an ASIC(s), a PLD(s), a FPLD(s), an analog circuit, and/or other circuitry. In examples disclosed herein, the example mood model validator 145 validates the mood model based on descriptors for known emotion(s) and/or mood(s) evoked in known music. For example, the known music may be classified by the model to determine if the mood or emotion classification made by the model matches the known mood or emotion classification. In examples disclosed herein, the example mood model validator 145 interfaces with the mood reference database 150 to identify emotion(s) and/or mood(s) associated with known audio. The example mood reference database 150 provides emotion(s) and/or mood(s) information that is tagged on a sample-by-sample (e.g., song-by-song) basis. However, in some examples, those emotion(s) and/or mood(s) may not line up with each of the emotion(s) and/or mood(s) used as part of the training set. To accommodate the pre-tagged emotion(s) and/or mood(s), in the illustrated example a semantic emotion/mood map is created mapping descriptors used in the mood reference database 150, to the emotion(s) and/or mood(s) used in the mood model database 140. In some examples, the emotion/mood map is created using semantic distance or closeness mapping, frequency of co-occurrence in regular internet space (e.g., Google word distances), frequency of co-occurrence in specific body of information (e.g., word distances based on occurrence in Wikipedia), and/or a manually curated maps. Using the emotion/mood maps, the mood model validator 145 of the illustrated example instructs the classification engine 130 to identify an emotion and/or a mood of the known audio using the mood model to be tested (e.g., the mood model stored in the mood model database 140). The identified emotion(s) and/or mood(s) is validated against the semantic emotion/mood map and/or the emotion/mood classification stored in the mood reference database 150 to determine if the mood model is functioning accurately.

In some examples, if the model classification is unsatisfactory, the model is modified and/or other training materials (e.g., additional recordings, additional emotions, additional pre-verbal utterances, etc.) are added to the training set. However, in some examples, it may be determined that the emotion(s) and/or mood(s) of the known audio is incomplete and/or incorrect. For example, a song that includes both sad and exuberant sections may only have been classified as sad, such that an identification of both sad and exuberant by the model would appear incorrect based on the limited match data, but would, in fact, be accurate.

The example mood reference database of the illustrated example of FIG. 1 is implemented by a database for storing the media and emotional classification metadata corresponding to the media. The mood reference database 150 of FIG. 1 may be implemented by any memory, storage device and/or storage disc for storing data such as, for example, flash memory, magnetic media, optical media, etc. Furthermore, the data stored in the mood reference database 150 may be in any data format such as, for example, binary data, comma delimited data, tab delimited data, structured query language (SQL) structures, etc. While in the illustrated example the mood reference database 150 is illustrated as a single database, the mood reference database 150 may be implemented by any number and/or type(s) of databases. In the illustrated example, the mood reference database 150 is hosted by a third party such as, for example, Gracenote, Inc. The Gracenote™ database provides emotion information that is tagged on a song-by-song basis. However, in some examples, the mood reference database 150 is implemented local to the mood model validator 145.

The example recommendation engine 155 of the illustrated example of FIG. 1 is implemented by a logic circuit such as a silicon-based processor executing instructions, but it could additionally or alternatively be implemented by an ASIC(s), a PLD(s), a FPLD(s), an analog circuit, and/or other circuitry. The example recommendation engine 155 of the illustrated example interfaces with the mood model database 140, the feature extractor 125, and/or the classification engine 130 to identify an emotion evoked by unknown media and/or to provide a recommendation of media based on an emotion to be evoked.

Within the consumer music streaming context, the recommendation engine 155 may be used to generate mood (and/or emotion) based radio channels, radio stations, personalized playlists, etc. Mood (and/or emotion) based clustering and/or recommendation of music enables discovery of music that is not based on the usual demography, genre, artist, etc. Mood (and/or emotion) based music may be used in the context of social media integration. For example, the example recommendation engine 155 may recommend media based on extracted textual-semantic or image based emotions from, for example, recent postings of a user's Facebook page. In some examples, the example recommendation engine 155 recommends media based on a user's current mood and/or the user's desired mood. In some examples, the user's current mood is measured with physiological and/or neurological sensors. In examples in which creation of a desired mood is intended, recommendations may provide a smooth transition path with multiple pieces of mood matched music progressing along the path from a current emotion/mood to a new emotion/mood. The path may be developed by considering the map of emotion(s) discussed above.

Within the marketing context, the example recommendation engine 155 may recommend an advertisement and/or program. Such recommendation may be based on a second-by-second and/or a segment-by-segment emotion profile of a storyline such that the selected music matches the intended emotion profile at the appropriate times. In some examples, emotion classification is used to tag emotions evolving in an audio track of an advertisement and/or program as a complement, covariate, or correlate to neuro-measures of the advertisement/program. In some examples, music is recommended by the example recommendation engine 155 based on a core brand emotion association or brand-equity-emotion association. For example, a political party seeking to produce an advertisement may request music associated with excitement for presenting a desired candidate, and/or may select depressing music when presenting an opposing candidate. In some examples, mood and/or emotion-based media recommendation is used in a retail environment to match music based on time-of-day, geography, demography of shoppers, location in the store, etc. In some examples, mood and/or emotion-based recommendation is used during a telephone call (e.g., as on-hold music). The music may be recommended by the example recommendation engine 155 based on a mood of a caller (as measured by the tone of voice and/or sensors), a type of caller (e.g., work colleague, family member, friend, etc.), the type of call (e.g., irate customer support, status inquiry, etc.), an environmental context, etc.

The example recommendation engine 155 may recommend and/or otherwise predict appropriateness of a selection of a musical instrument. For example, a trumpet sound may be more likely to be associated with a particular emotion. In some examples, musical databases may be tagged with emotion and/or mood identifiers. In such examples, the tagging may be performed as the song evolves, as compared to a classification associated with the entire piece of music. In some examples, smart maps (similar to the semantic maps described above) may be used to associate mood covariates to other traditional catalogue meta tags. In some examples, second-by-second emotion tagging may be used to select appropriate (e.g., optimal) samples of music for different situations and/or moods.

In the illustrated example of FIG. 1, the recommendation engine 155 is shown as part of the example mood identification system 105. However, in some examples, the example recommendation engine 155 is eliminated and/or is implemented as part of a remote computing device (e.g., a server) which may be operated by a third party, and/or by a media device 160 local to the subject user such as, for example, a tablet, a desktop computer, a laptop computer, a mobile computing device, a television, a smart phone, a mobile phone, an Apple® iPad®, an Apple® iPhone®, an Apple® iPod®, an Android™ powered computing device, a Palm® webOS® computing device, etc.

The example media device 160 of the illustrated example of FIG. 1 includes an example media presenter 165, example telephone functionality 166, and an example sensor 167. The example media presenter 165 of the illustrated example of FIG. 1 is implemented by speakers and/or a display of a media device 160. In the illustrated example, the example media presenter 165 presents media based on a selection made by the recommendation engine 155. For example, during a media presentation by the example media presenter 165, the recommendation engine 155 may recommend particular media to play next. Based on the recommendation, the example media presenter 165 presents the selected media. In some examples, the media presenter 165 retrieves the selected media from a remote media source such as, for example, a streaming server, a web server, etc. In other examples, local media is accessed and played (e.g., from an iTunes™ library).

The example telephone functionality 166 is implemented by a cellular radio capable of communicating with a cellular telephone network. However, the example telephone functionality may be implemented in any other fashion. In the illustrated example, the cellular telephone network is a Global System for Mobile Communications (GSM) network. However, any other past, present, and/or future type of telephonic network may additionally or alternatively be used such as, for example, a Code Division Multiple Access (CDMA) network, a Long Term Evolution (LTE) network, etc. Moreover, networks other than a cellular network may additionally or alternatively be used. For example, a plain old telephone system (POTS) network, a voice over Internet protocol (VOIP) system, etc. may be used.

The example sensor 167 of the example mobile device 160 of the illustrated example of FIG. 1 includes one or more of an accelerometer, a temperature sensor, a global positioning system (GPS) sensor, a microphone, an altimeter, a gyroscope, an orientation sensor, a magnetic sensor, a physiological sensor, a neurological sensor, etc. The example sensor 167 enables identification of context data by the recommendation engine 155 to, for example, facilitate recommendation of media for presentation.

Figure 2:
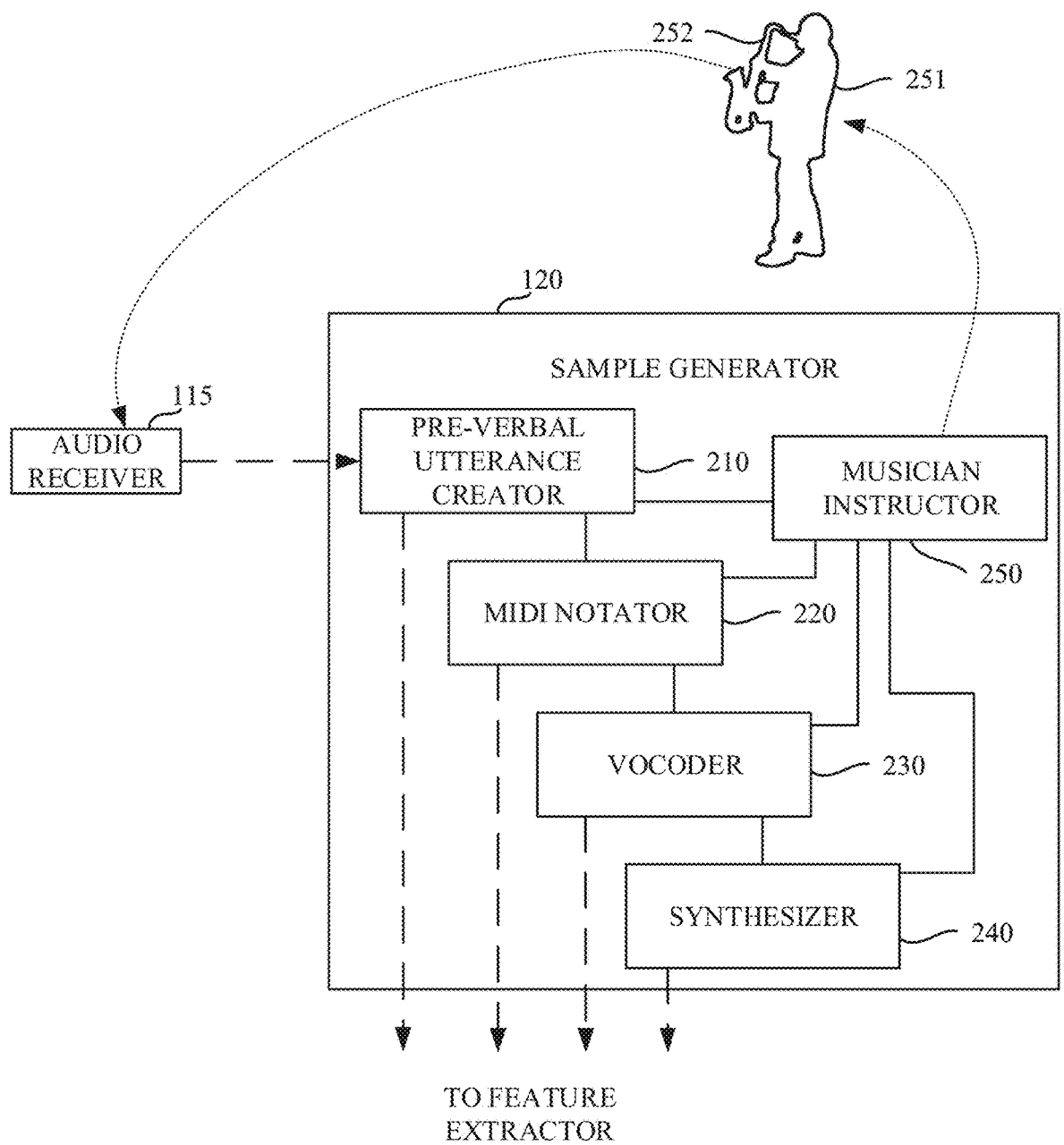
FIG. 2 is a block diagram of an example implementation of the sample generator illustrated in FIG. 1.

FIG. 2 is a block diagram of an example implementation of the sample generator 120 of FIG. 1. The example sample generator 120 of FIG. 2 includes a pre-verbal utterance creator 210, a Musical Instrument Digital Interface (MIDI) notator 220, a vocoder 230, a synthesizer 240, and a musician instructor 250. In examples disclosed herein, having a robust training set results in a robust mood model. As such, it is advantageous to create many varied samples that correspond to a particular emotion. Moreover, using pre-verbal utterances results in identification of core, building block, sounds that evoke a particular human emotion which, again, results in a more robust mood model.

The example pre-verbal utterance creator 210 of the illustrated example of FIG. 2 is implemented by a logic circuit such as a silicon-based processor executing instructions, but it could additionally or alternatively be implemented by an ASIC(s), a PLD(s), a FPLD(s), an analog circuit, and/or other circuitry. In some examples disclosed herein, pre-verbal utterances are used as the core input to create a training set for the model. In the illustrated example, the pre-verbal utterances are created by recording a human voice while uttering a sound corresponding to a particular emotion. For example, when a sample corresponding to sorrow is desired, the pre-verbal utterance creator 210 records a person while sobbing to create a sample corresponding to sorrow. As different people may make different sobbing sounds, it is advantageous to create many samples of different people sobbing to create a range of pre-verbal utterances corresponding to sorrow. Many samples are advantageously used for many corresponding emotions (e.g., fear (screaming), joy (laughter), etc.). In some examples, sounds from nature may be used in addition to or as an alternative to pre-verbal utterances. For example, a sound of lightning may be associated with an emotion of fear, whereas a sound of a bubbling stream may be associated with an emotion of calm. Moreover animal sounds (e.g., a dog barking, a cat meowing, a lion roaring, etc.) may be used. As disclosed herein, any sound that can be identified as associated with an emotion may additionally or alternatively be used.

The example MIDI notator 220 of the illustrated example of FIG. 2 is implemented by a logic circuit such as a silicon-based processor executing instructions, but it could additionally or alternatively be implemented by an ASIC(s), a PLD(s), a FPLD(s), an analog circuit, and/or other circuitry. In the illustrated example, a pre-verbal utterance and/or other sample is input to the example MIDI notator 220. The example MIDI notator converts the sample into a digital MIDI-based representation. Once in a digital format, the MIDI-based representation can be altered by being played back at a different tempo, being played back using a different pitch, etc. As such, samples representing the pre-verbal utterance may be created by the example MIDI notator 220 that have different audio qualities but remain correlated to the underlying emotion of the pre-verbal utterance. As a result, a large range of samples for each emotion of interest can be quickly catalogued and subsequently used for classifying media.

The example vocoder 230 of the illustrated example of FIG. 2 is implemented by a logic circuit such as a silicon-based processor executing instructions, but it could additionally or alternatively be implemented by an ASIC(s), a PLD(s), a FPLD(s), an analog circuit, and/or other circuitry. In some examples, the samples created by the MIDI notator 220 are passed through the example vocoder 230. The example vocoder 230 filters extraneous sounds and extracts core acoustic content of the samples to create vocoder-processed samples. Moreover, these vocoder processed samples remain correlated to the underlying emotion of the pre-verbal utterance and, therefore, create a more robust set of samples to be used as the training set.

The example synthesizer 240 of the illustrated example of FIG. 2 is implemented by a logic circuit such as a silicon-based processor executing instructions, but it could additionally or alternatively be implemented by an ASIC(s), a PLD(s), a FPLD(s), an analog circuit, and/or other circuitry. In some examples, the vocoder-processed representation is synthesized using one or more different synthesized instruments. For example, the vocoder-based representation of human laughter (representing humor) may be reproduced using a synthesized instrument (e.g., a trumpet). The example synthesized instrument audio is then mapped to the emotion of humor. The same emotion may be synthesized using many different instruments and/or instrument combinations. Thus, in some examples, a pre-verbal utterance made by a human voice and representing a particular emotion is processed into a synthesized instrument sample or range of synthesized instrument samples. This approach may make matching instrument sounds in music to be classified to an emotion more accurate. In some examples, many different instruments (e.g., a saxophone, a guitar, a piano, etc.) are used to create many different synthesized samples for the same emotion/pre-verbal utterance. This approach creates a robust model that can map many different instrument sounds to the same emotion (e.g., a piano and a trumpet played in an appropriate manner may both map to sadness or joy or another emotion.

In examples disclosed herein, the musician instructor 250 instructs a musician to replicate the synthesized audio on an actual (e.g., non-synthesized) instrument. In some examples, the musicians are instructed to recreate the pre-verbal utterance, the MIDI-based sample, the vocoder-based sample, and/or the synthesized sample using a musical instrument. For example, a saxophonist 251 may play a saxophone 252 to mimic and/or otherwise re-create the synthesized audio. Replicating the synthesized audio introduces an organic musical lexicography back into the pre-verbal utterances training materials. The re-produced audio from the musician is received via the audio source 110 and/or the audio receiver 115. The example re-produced audio may then be used in association with the training data in connection with the emotion on which it was based. The re-production may be done by many different musicians to create many different reproduced audio for the same or different emotion(s) to thereby increase the robustness of the training set.

In some examples, the example musician instructor 250 instructs a musician to interpretively re-compose the sample using their own creativity. In some examples, the example musician instructor 250 constrains the musician in a manner to not stray too far from the original sample to be re-composed. For example, temporal and phrasing latitude of the musician may be constrained. Allowing the musicians to re-compose the synthesized sample into another form re-enforces the connection between composed music and the emotion on which the pre-verbal utterance used to create the composed music is based. In some examples, the re-composed sample is processed by the example pre-verbal utterance creator 210, the example MIDI notator 220, the example vocoder 230, and/or the example synthesizer 240 to create additional samples. The re-composed audio may then be used in association with the training data as conveying the emotion on which it was based.

While the example pre-verbal utterance creator 210, the example MIDI notator 220, the example vocoder 230, and the example synthesizer 240 create samples that are correlated to the underlying emotion of the pre-verbal utterance and/or the audio sample on which they are based, in some examples, a user and/or panel of users may verify that the generated samples still convey the intended emotion. For example, a user or group of users may be asked to confirm that the synthesized trumpet audio still conveys humor. If, for example, the sample does not convey the intended emotion, it is omitted from the training set. In some examples, user(s) may be asked to confirm a degree of the emotion conveyed. For example, users may be asked to rate a happiness of a sample on a scale of zero to ten (0 to 10). In some examples, user-identified composed music samples identified as evoking a particular emotion are added to the training set.

Figure 3:
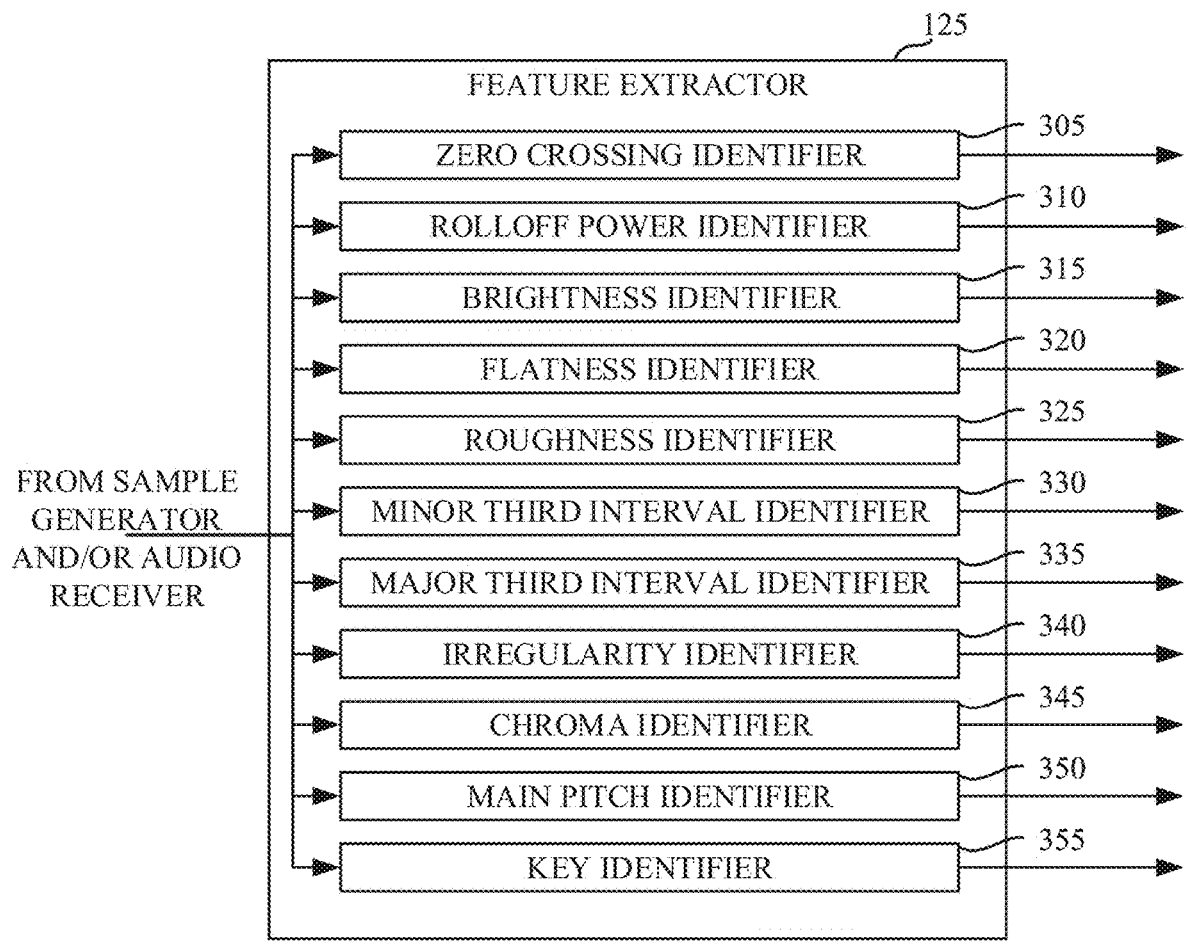
FIG. 3 is a block diagram of an example implementation of the feature extractor illustrated in FIG. 1.

FIG. 3 is a block diagram of an example implementation of the feature extractor 125 of FIG. 1. The example feature extractor 125 includes an example zero crossing identifier 305, an example rolloff power identifier 310, an example brightness identifier 315, an example flatness identifier 230, an example roughness identifier 325, an example minor third interval identifier 330, an example major third interval identifier 335, an example irregularity identifier 340, an example chroma identifier 345, an example main pitch identifier 350, and an example key identifier 355. The example feature extractor 125 analyzes received samples to create metrics for one or more features of the received samples. While in the illustrated example, features such as, for example, zero crossings, rolloff power, brightness, flatness, roughness, minor third interval power, major third interval power, irregularity, chroma, main pitch, a key, etc., the example feature extractor 125 may additionally or alternatively identify any other feature(s) of the received samples such as, for example, a mode of the sample, the presence of particular chords in the sample, etc. Moreover, while various features are identified by the example feature extractor 125, any number of features may be used when characterizing an emotion of a sample. For example, at least one of the features may be used, at least two of the features may be used, at least three of the features may be used, all of the features may be used, etc.

Figure 4:
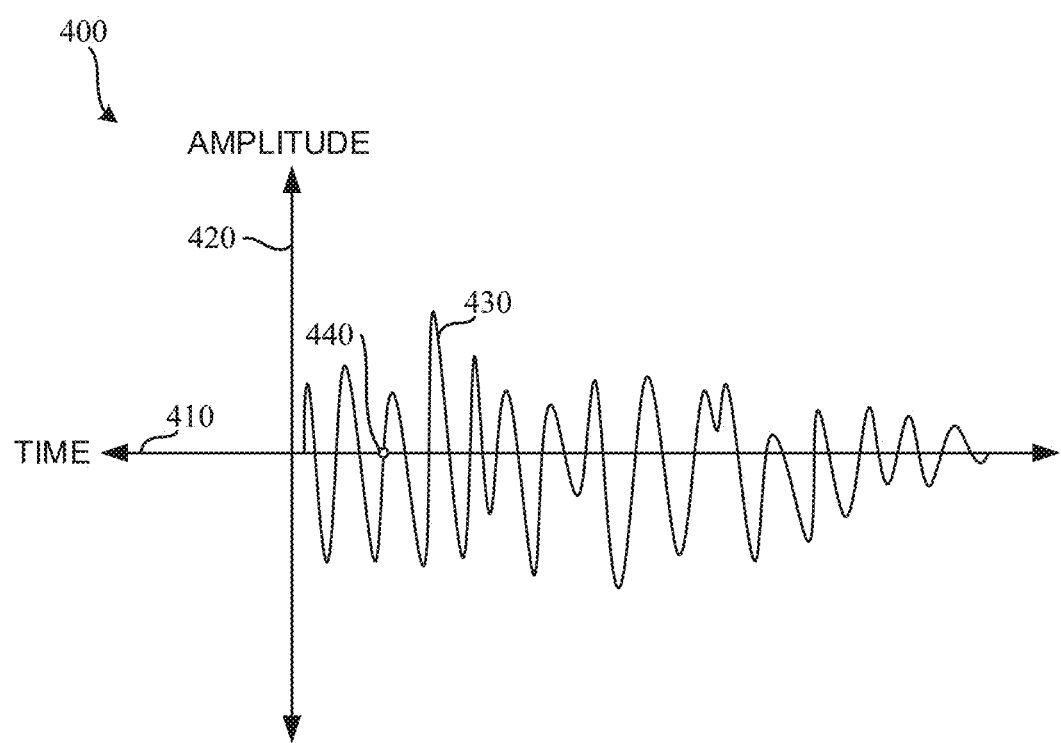
FIG. 4 is a diagram illustrating example audio to be analyzed by the zero crossing identifier of FIG. 3.

The example zero crossing identifier 305 of the illustrated example of FIG. 3 is implemented by a logic circuit such as a silicon-based processor executing instructions, but it could additionally or alternatively be implemented by an ASIC(s), a PLD(s), a FPLD(s), an analog circuit, and/or other circuitry. The example zero crossing identifier 305 identifies zero crossings in the audio sample. A zero crossing is an instance in which the amplitude of a time band audio waveform is equal to and/or crosses zero. An example of identification of zero crossings of a sample is shown in FIG. 4. FIG. 4 illustrates a waveform 430 of an example audio sample. FIG. 4 includes a time axis 410 and an amplitude axis 420. The zero crossing identifier 305 identifies occurrences where the amplitude of the waveform 430 has zero amplitude. An example occurrence of the waveform 430 having an amplitude of zero is shown at the circle 440. The example zero crossing identifier 305 counts a total number of occurrences of zero crossings over a time period such as, for example, ten seconds. In some examples, the zero crossing identifier reflects the count in a rate metric representing the number of zero crossings per unit of time (e.g., ten zero crossings per second).

Figure 5:
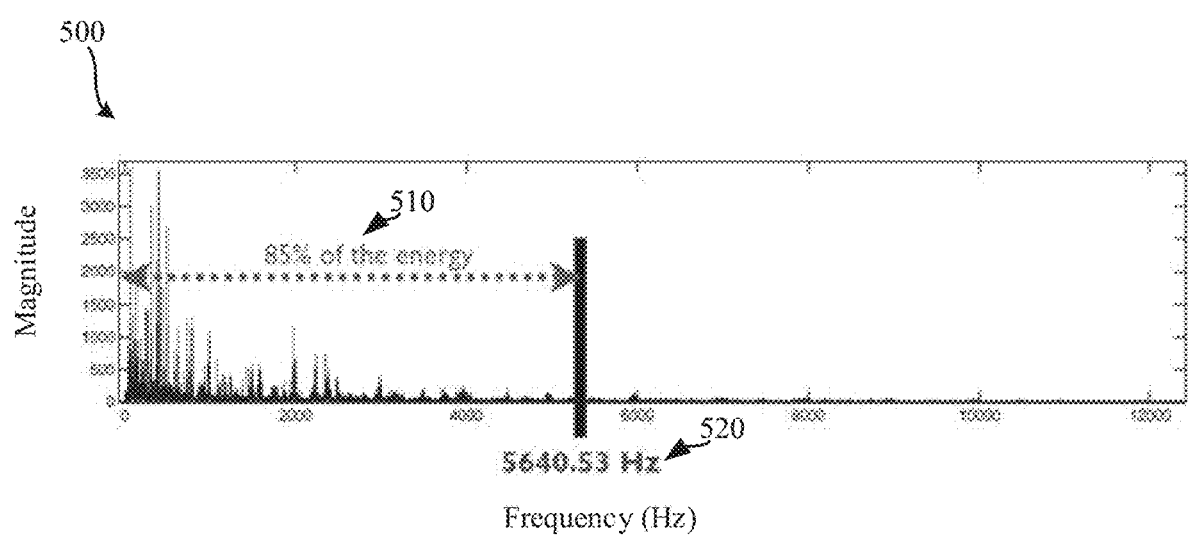
FIG. 5 is a diagram illustrating identification of a rolloff power by the rolloff power identifier of FIG. 3.

The example rolloff power identifier 310 of the illustrated example of FIG. 3 is implemented by a logic circuit such as a silicon-based processor executing instructions, but it could additionally or alternatively be implemented by an ASIC(s), a PLD(s), a FPLD(s), an analog circuit, and/or other circuitry. The example rolloff power identifier 310 creates a metric representative of the rolloff power of a frequency spectrum of the received sample. As used herein, rolloff power is defined to be a quantization of power of an audio signal that is below a frequency threshold (e.g., a rolloff frequency) in the frequency domain representation of the audio signal. Rolloff power reflects the presence of low frequency signals (e.g., lower pitched tones) within an audio sample. FIG. 5 illustrates an example determination of rolloff power. In the illustrated example of FIG. 5, the example rolloff power identifier 310 determines a frequency domain representation 500 of the audio sample. The frequency domain representation 500 may be obtained, for example, by performing a Fourier transform on the sample.

The example rolloff power identifier 310 identifies a rolloff frequency 520, and identifies a percentage of power within the frequency domain representation 500 that is below the rolloff frequency 520. In the illustrated example, the example rolloff frequency 520 is five thousand six hundred forty and fifty three hundredths (5640.53) hertz. However, any other frequency may additionally or alternatively be used. In the illustrated example, the example rolloff power identifier 310 identifies that eighty five (85) percent 510 of the energy of the frequency domain representation 500 is below the rolloff threshold 520. In the illustrated example, the rolloff power is represented as a percentage of the total power of the frequency domain representation 500 of the audio sample. However, the rolloff power may be represented in any other fashion such as, for example, in watts, etc.

Moreover, while in the illustrated example, the example rolloff power is determined by identifying power below a frequency threshold, the example rolloff power may be identified in any other fashion. For example, the rolloff power may be represented as an upper frequency boundary to a threshold amount of energy within the frequency domain representation 500. For example, the example rolloff power identifier 310 may identify that five thousand six hundred forty and fifty three hundredths (5640.53) hertz forms an upper boundary to eighty five (85) percent of the total power of the frequency domain representation 500.

The example brightness identifier 315 of the illustrated example of FIG. 3 is implemented by a logic circuit such as a silicon-based processor executing instructions, but it could additionally or alternatively be implemented by an ASIC(s), a PLD(s), a FPLD(s), an analog circuit, and/or other circuitry. The example brightness identifier 315 of the illustrated example of FIG. 3 generates a metric representing a brightness of the received audio. As used herein, brightness refers to a characteristic of a timbre of a sound. To measure brightness, the brightness identifier 315 determines a percentage of power of a frequency domain representation 600 of the received sample that is above a threshold frequency. Samples that have a higher percentage of power above a threshold frequency tend to exhibit higher pitched tones within an audio sample.

Figure 6:
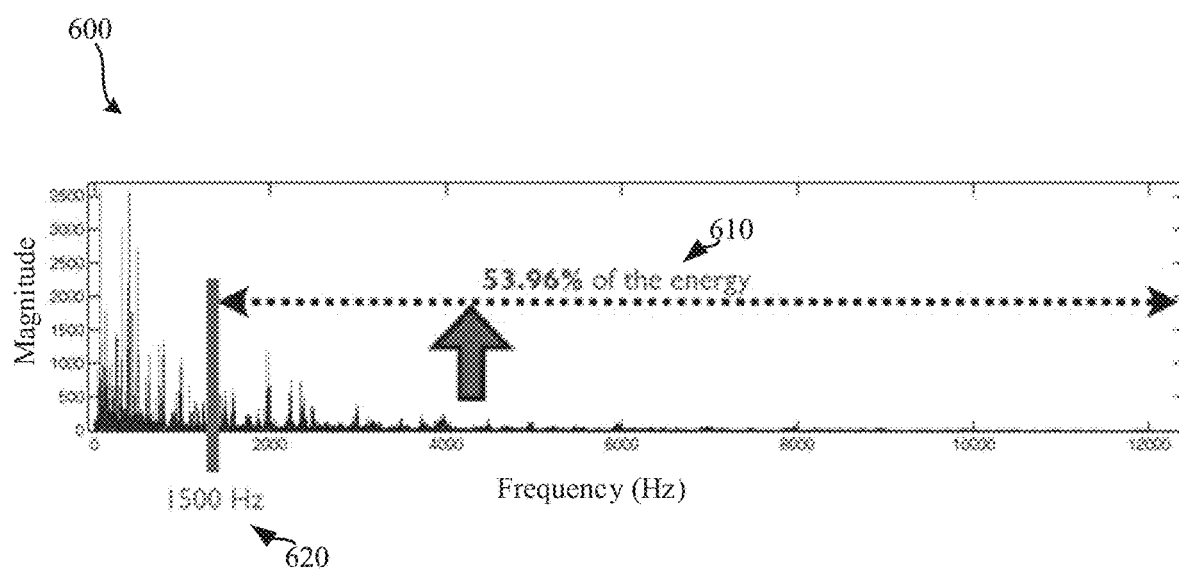
FIG. 6 is a diagram illustrating identification of a brightness by the brightness identifier of FIG. 3.

FIG. 6 illustrates an example brightness determination. In the illustrated example of FIG. 6, the brightness identifier 315 uses a threshold frequency 620 of fifteen hundred (1500) hertz. In the illustrated example, the example threshold frequency 620 of fifteen hundred hertz is used because it represents a frequency in the upper range of fundamental frequencies that many musical instruments are able to produce. Tones produced by musical instruments are typically referred to as having fundamental frequencies and harmonic frequencies. Fundamental frequencies represent the lowest frequency produced by a particular musical instrument. In some examples, the fundamental frequency is referred to as a first harmonic. Harmonic frequencies represent an integer multiple of the fundamental frequency. When many harmonic frequencies are audible, audio is referred to as being bright. Many musical instruments have an upper range of fundamental frequencies in a range of seven hundred (700) hertz to three thousand (3000) hertz. For example, a trumpet has an upper range of fundamental frequency of approximately one thousand (1000) hertz. As such, using an example threshold frequency of fifteen hundred (1500) hertz results in detection of harmonic frequencies of most musical instruments. However, any other threshold frequency may additionally or alternatively be used.

In the illustrated example of FIG. 6, the example brightness identifier 315 determines a frequency domain representation 600 of the audio sample. The frequency domain representation 600 may be obtained, for example, by performing a Fourier transform on the sample. Based on the threshold frequency, the brightness identifier 315 identifies a power of the frequency domain representation 600 that is above the threshold frequency 620. In the illustrated example, the power above the threshold frequency 620 is represented as a percentage of the total power of the frequency domain representation 600. In the illustrated example, the power of the frequency domain representation 600 above the threshold frequency 620 is identified by applying a high pass filter to create a filtered sample and detecting a power of the filtered sample. The power of the filtered sample is compared against a power of the sample itself. In the illustrated example of FIG. 6, the brightness identifier 315 determines that fifty three and ninety six hundredths (53.96) percent of the power is above the threshold frequency 620. Thus, the brightness in this example is determined to be fifty three and ninety six hundredths (53.96) percent. However, any other brightness determination may be made in any other fashion. For example, the brightness identifier 315 may identify a fundamental frequency of the frequency domain representation of the received sample and apply a high pass filter at or slightly above the identified fundamental frequency to better identify harmonic frequencies.

The example flatness identifier 320 of the illustrated example of FIG. 3 is implemented by a logic circuit such as a silicon-based processor executing instructions, but it could additionally or alternatively be implemented by an ASIC(s), a PLD(s), a FPLD(s), an analog circuit, and/or other circuitry. As used herein, flatness represents a quantification of noise present in a signal versus distinct tones. The example flatness identifier 320 identifies flatness by determining a frequency spectrum of an audio sample by, for example, performing a Fourier transform on the sample. The example flatness identifier 320 of the illustrated example of FIG. 3 identifies the flatness by dividing a geometric mean of the frequency spectrum by an arithmetic mean of the frequency spectrum. In some examples, the following equation is used to quantify flatness:

$$\frac{\sqrt[N]{\prod_{n=0}^{N-1} x(n)}}{\frac{\sum_{n=0}^{N-1} x(n)}{N}} \quad \text{(Equation 1)}$$

In example equation 1, the function $x(n)$ represents an amplitude of the frequency spectrum at an input frequency $n$. N represents the maximum frequency used for measuring spectral flatness. In some examples, a value of twenty kilohertz (20,000 Hz) is used because, for example, frequencies ranging from zero hertz to twenty kilohertz represent an approximation of a range of frequencies discernable by the human ear. However, any other frequency range may additionally or alternatively be used. While in the illustrated example, equation 1 is used to identify flatness, any other way of identifying flatness may additionally or alternatively be used.

Figure 7:
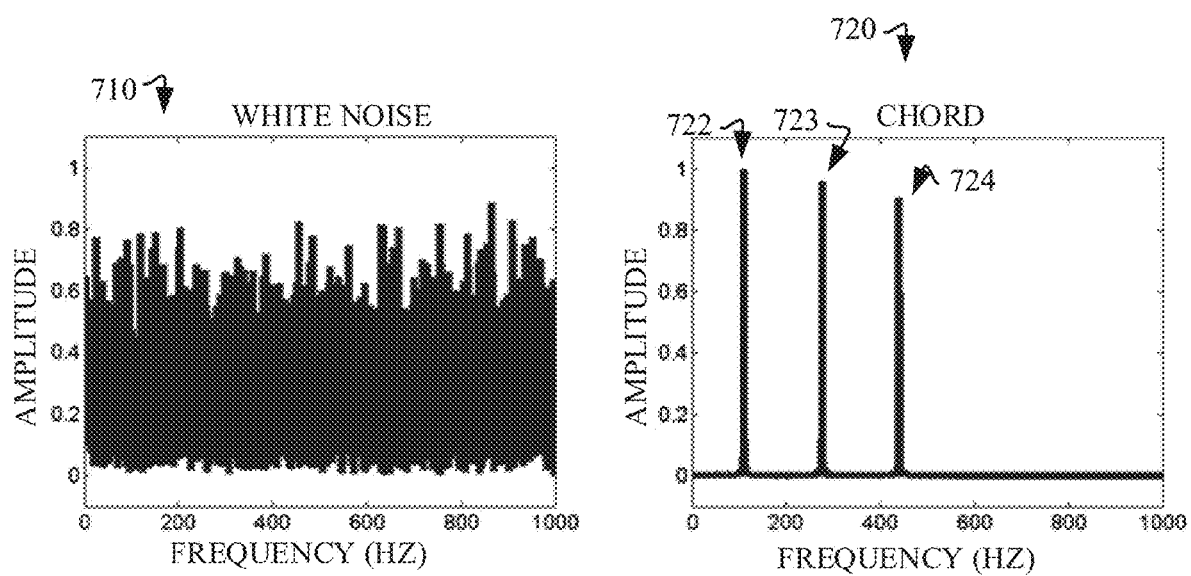
FIG. 7 is a diagram illustrating identification of a flatness by the flatness identifier of FIG. 3.

FIG. 7 represents an example distinction between frequency domain representations of two different audio samples. A first example frequency domain representation 710 represents a white noise signal. In this example, the flatness identifier 320 identifies the received sample as being flat because the amplitude of the frequency domain representation is relatively steady throughout a frequency spectrum. In some examples, a flat sample results in a high ratio of the geometric mean divided by the arithmetic mean (e.g., a ratio approaching one (1)).

FIG. 7 further illustrates a second example frequency domain representation 720 representing a musical chord. As shown in FIG. 7, the peaks in the second example frequency domain representation 720 represent the tones A2 (tone 722), C#4 (tone 723), and A4 (tone 724). In such an example, the flatness identifier 320 identifies the received sample as being not flat because the ratio of the geometric mean divided by the arithmetic mean is low (e.g., a ratio approaching zero (0)).

The example roughness identifier 325 of the illustrated example of FIG. 3 is implemented by a logic circuit such as a silicon-based processor executing instructions, but it could additionally or alternatively be implemented by an ASIC(s), a PLD(s), a FPLD(s), an analog circuit, and/or other circuitry. The example roughness identifier 325 of the illustrated example of FIG. 3 identifies a roughness of the received audio sample. As used herein, roughness (which is also sometimes referred to as sensory dissonance) is a measure of occurrence of dissonant tones in an audio sample and/or the power of such dissonant tones. Dissonance occurs when, for example, a combination of notes sounds harsh or unpleasant to a human listener. Dissonant sounds can be measured by identifying particular intervals that are known as dissonant. As used herein, an interval is a difference between two musical notes on a musical scale. In examples disclosed herein, the musical notes are notes on a diatonic scale (i.e., a twelve tone scale). Two adjacent notes (e.g., C and $C^{\#}$, E and $E^b$, etc.) are referred to as being a semitone (also referred to as a half-step) apart from each other. In some examples, dissonant intervals are measured by identifying particular intervals that are known as dissonant. For example, intervals such as a minor second (e.g., two tones being one semitone apart from each other), a major seventh (e.g., two tones being one semitone apart from each other), an augmented fourth (e.g., two tones being six semitones apart from each other), a diminished fifth (e.g., two tones being six semitones apart from each other), etc. may be identified to determine a level of dissonance in a received sample. While in the illustrated example, a diatonic scale (e.g., a twelve tone scale) is used, any other musical scale system may additionally or alternatively be used.

Figure 8:
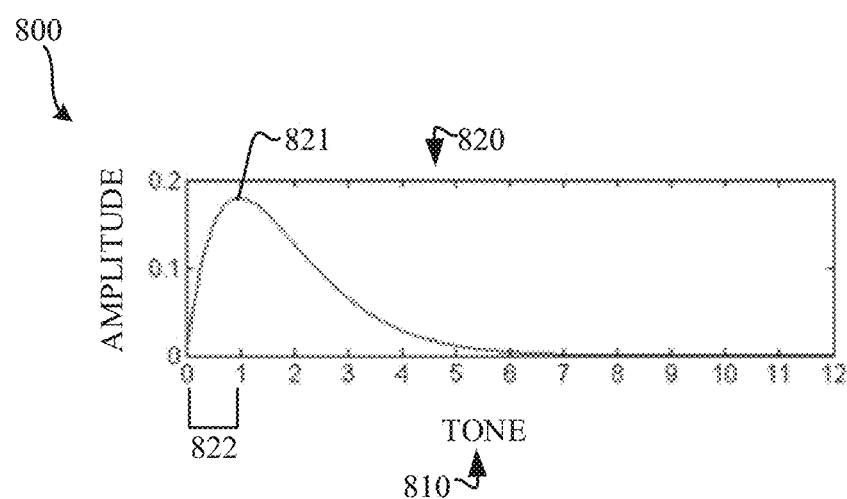
FIG. 8 is a diagram illustrating identification of a roughness by the roughness identifier of FIG. 3.

FIG. 8 represents an example roughness identification. In the illustrated example, a twelve tone scale 810 is used. However, any other tone system and/or scale may additionally or alternatively be used. In the illustrated example of FIG. 8, a power of relationships between various tones 810 in an audio sample is shown. In the illustrated example, a peak 821 is identified having an interval of a minor second 822 (e.g., two adjacent tones). The amplitude of the dissonance is identified by the roughness identifier 325 by identifying an amplitude of frequency differences having a ratio of sixteen to fifteen (16:15). While, in the illustrated example, an interval of a minor second is identified, any other interval may additionally or alternatively be identified.

The example minor third interval identifier 330 of the illustrated example of FIG. 3 is implemented by a logic circuit such as a silicon-based processor executing instructions, but it could additionally or alternatively be implemented by an ASIC(s), a PLD(s), a FPLD(s), an analog circuit, and/or other circuitry. The example minor third interval identifier 330 of the illustrated example of FIG. 3 identifies the presence and/or amplitude of minor third intervals in the received sample. As used herein, a minor third interval is identified an interval that has peaks in a frequency spectrum at a frequency ratio of six to five (6:5).

Figure 9:
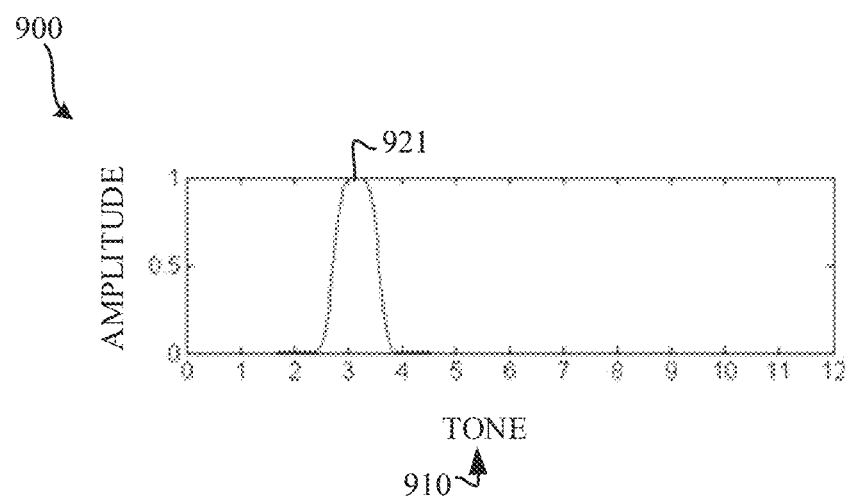
FIG. 9 is a diagram illustrating identification of a minor third interval by the minor third identifier of FIG. 3.

FIG. 9 represents an example identification of a minor third interval. In the illustrated example, a twelve tone scale 910 is used. However, any other tone system may additionally or alternatively be used. In the illustrated example of FIG. 9, an amplitude of relationships between various ones of the twelve tones 910 in an audio sample is shown. In the illustrated example, a peak 921 is identified as having an interval of a minor third (e.g., an interval of three half-steps). The example minor third interval identifier 330 detects an amplitude of the frequency ratio by creating a frequency domain representation of the audio sample and scanning the frequency domain for an amplitude of intervals having a ratio of six to five (e.g., a minor third interval). The amplitude is reported to the classification engine 130.

The example major third interval identifier 335 of the illustrated example of FIG. 3 is implemented by a logic circuit such as a silicon-based processor executing instructions, but it could additionally or alternatively be implemented by an ASIC(s), a PLD(s), a FPLD(s), an analog circuit, and/or other circuitry. The example major third interval identifier 335 of the illustrated example of FIG. 3 identifies the presence and/or amplitude of major third intervals in the received sample. As used herein, a major third interval is defined to be an interval that has peaks in a frequency spectrum at a frequency ratio of five to four (5:4).

Figure 10:
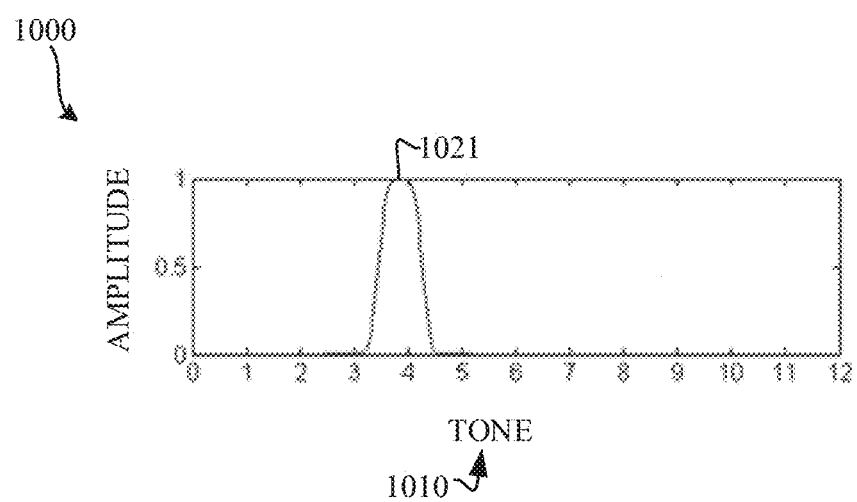
FIG. 10 is a diagram illustrating identification of a major third interval by the major third identifier of FIG. 4.

FIG. 10 represents an example identification of a major third interval. In the illustrated example, a twelve tone scale 1010 is used. However, any other tone system may additionally or alternatively be used. In the illustrated example of FIG. 10, an amplitude of relationships between various ones of the twelve tones 1010 in an audio sample is shown. In the illustrated example, a peak 1021 is identified having an interval of a major third (e.g., an interval of four half-steps). The example major third interval identifier 335 detects an amplitude of the frequency ratio by creating a frequency domain representation of the audio sample and scanning the frequency domain for an amplitude of intervals having a ratio of five to four (e.g., a major third interval) of a major third and reports the amplitude to the classification engine 130.

The example irregularity identifier 340 of the illustrated example of FIG. 3 is implemented by a logic circuit such as a silicon-based processor executing instructions, but it could additionally or alternatively be implemented by an ASIC(s), a PLD(s), a FPLD(s), an analog circuit, and/or other circuitry. The example irregularity identifier 340 of the illustrated example of FIG. 3 analyzes a received sample to identify irregularity within the received sample. As used herein, irregularity of a sample is a metric corresponding to a measure of harmonicity, and/or the presence of harmonic frequencies having a similar amplitude to their associated fundamental frequency (e.g., within 10 percent of the amplitude of the fundamental frequency). As used herein, a fundamental frequency is the lowest frequency of a periodic waveform. As used herein, a harmonic frequency is an integer multiple of the fundamental frequency. Harmonicity is defined herein to be the presence of one or more harmonic frequencies in relation to the fundamental frequency.

Figure 11:
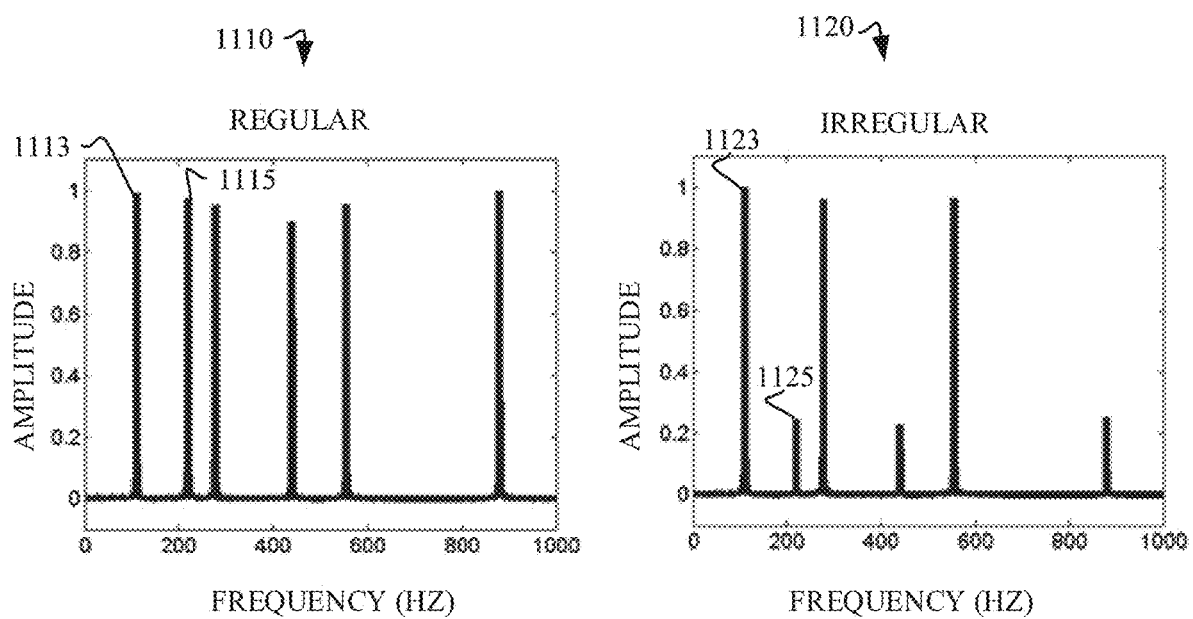
FIG. 11 is a diagram illustrating identification of an irregularity by the irregularity identifier of FIG. 3.

FIG. 11 illustrates frequency domain representations of two audio samples; one regular (e.g., having low or zero irregularity) and one exhibiting high irregularity). The first example frequency domain representation 1110 includes a harmonic frequency 1115 having a similar amplitude to a fundamental frequency 1113. The example irregularity identifier 340 identifies that the amplitudes are similar by calculating a ratio between the amplitude of the harmonic tone 1115 and the fundamental frequency 1113. As such, the first example 1110 of the illustrated example of FIG. 11 is identified as exhibiting regularity by the irregularity identifier 340. A second example frequency domain representation 1120 includes a harmonic tone 1125 that does not have a similar amplitude to a fundamental tone 1123. The example irregularity identifier 340 identifies that the amplitudes are dissimilar by calculating a ratio between the amplitude of the harmonic tone 1125 and the fundamental frequency 1123. As such, the second example 1120 of the illustrated example of FIG. 11 is identified as being irregular by the irregularity identifier 340.

Figure 12:
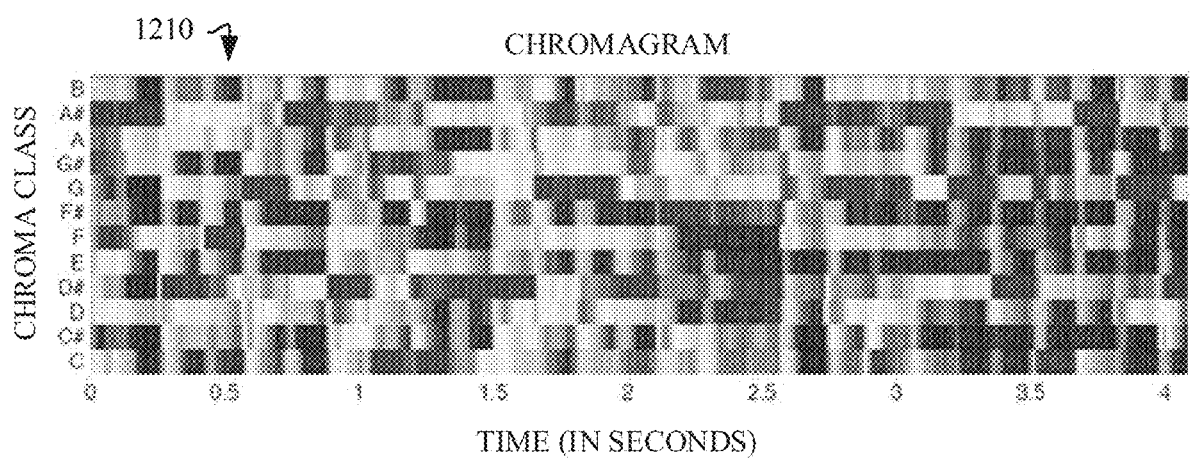
FIG. 12 is a diagram illustrating identification of a chromagram for identification of a chroma by the chroma identifier of FIG. 3, a main pitch by the main pitch identifier of FIG. 3, and a key by the key identifier of FIG. 3.

The example chroma identifier 345 of the illustrated example of FIG. 3 is implemented by a logic circuit such as a silicon-based processor executing instructions, but it could additionally or alternatively be implemented by an ASIC(s), a PLD(s), a FPLD(s), an analog circuit, and/or other circuitry. The example chroma identifier 345 of the illustrated example of FIG. 3 generates a chroma representing received audio. As used herein, a chroma is a representation of audio in which an entire spectrum of the audio is projected onto the twelve semitones of a musical octave. Notes that are one octave apart (e.g., C3 and C4, $E^b5$ and $E^b6$, etc.) are represented as the same tone. In the illustrated example, the chroma is digitally represented as an array of intensities of different tones at different times. A chroma may be visually illustrated by a chromagram. FIG. 12 illustrates an example chromagram 1210. The example chromagram of FIG. 12 is used as an input to the classification engine 130 to identify an emotion associated with the received sample as explained further below. The chroma is generated by the chroma identifier 345 by reducing all tones within a sample to a single octave, and representing the intensity of the various tones along a time axis. As shown in the illustrated example of FIG. 12, darker shaded sections represent tones (e.g., notes) that have a higher intensity than those sections represented using lighter shading.

The example main pitch identifier 350 of the illustrated example of FIG. 3 is implemented by a logic circuit such as a silicon-based processor executing instructions, but it could additionally or alternatively be implemented by an ASIC(s), a PLD(s), a FPLD(s), an analog circuit, and/or other circuitry. The example main pitch identifier 350 of the illustrated example of FIG. 3 identifies a main pitch of a received audio sample. In the illustrated example, the main pitch is defined to be a tone in a sample which occurs with the greatest amplitude. In some examples, the main pitch identifier 350 inspects a chromagram generated by the chroma identifier 345 to determine the main pitch of an audio sample. The example main pitch identifier 350 can identify the main pitch from the chromagram by, for example, identifying a tone that is the most intense throughout the sample. However, any other technique for identifying the main tone may additionally or alternatively be used.

The example key identifier 355 of the illustrated example of FIG. 3 is implemented by a logic circuit such as a silicon-based processor executing instructions, but it could additionally or alternatively be implemented by an ASIC(s), a PLD(s), a FPLD(s), an analog circuit, and/or other circuitry. The example key identifier 355 of the illustrated example of FIG. 3 identifies a musical key of a received audio sample. As used herein, the musical key is defined to be a tonic note and/or chord. A tonic note is defined as the first scale degree of a diatonic scale, a tonal center, and/or a final resolution tone. A chord is defined as a sequence of notes separated by intervals. In the illustrated example, the musical key is identified by the example key identifier 355 by inspecting a chromagram generated by the chroma identifier to determine a tonic note and/or chord of the received audio sample. The example key identifier 355 can identify the key by detecting tones present in the chromagram and analyzing those tones to identify a pattern representing a chord. In the illustrated example, the tonic note is selected from those tones identified within the chord. However, in some examples, the tonic note is not present within the chord. In some examples, the tonic note matches the main pitch identified by the main pitch identifier 350. However, any other technique for identifying the musical key of the received sample may additionally or alternatively be used.

Figure 13:
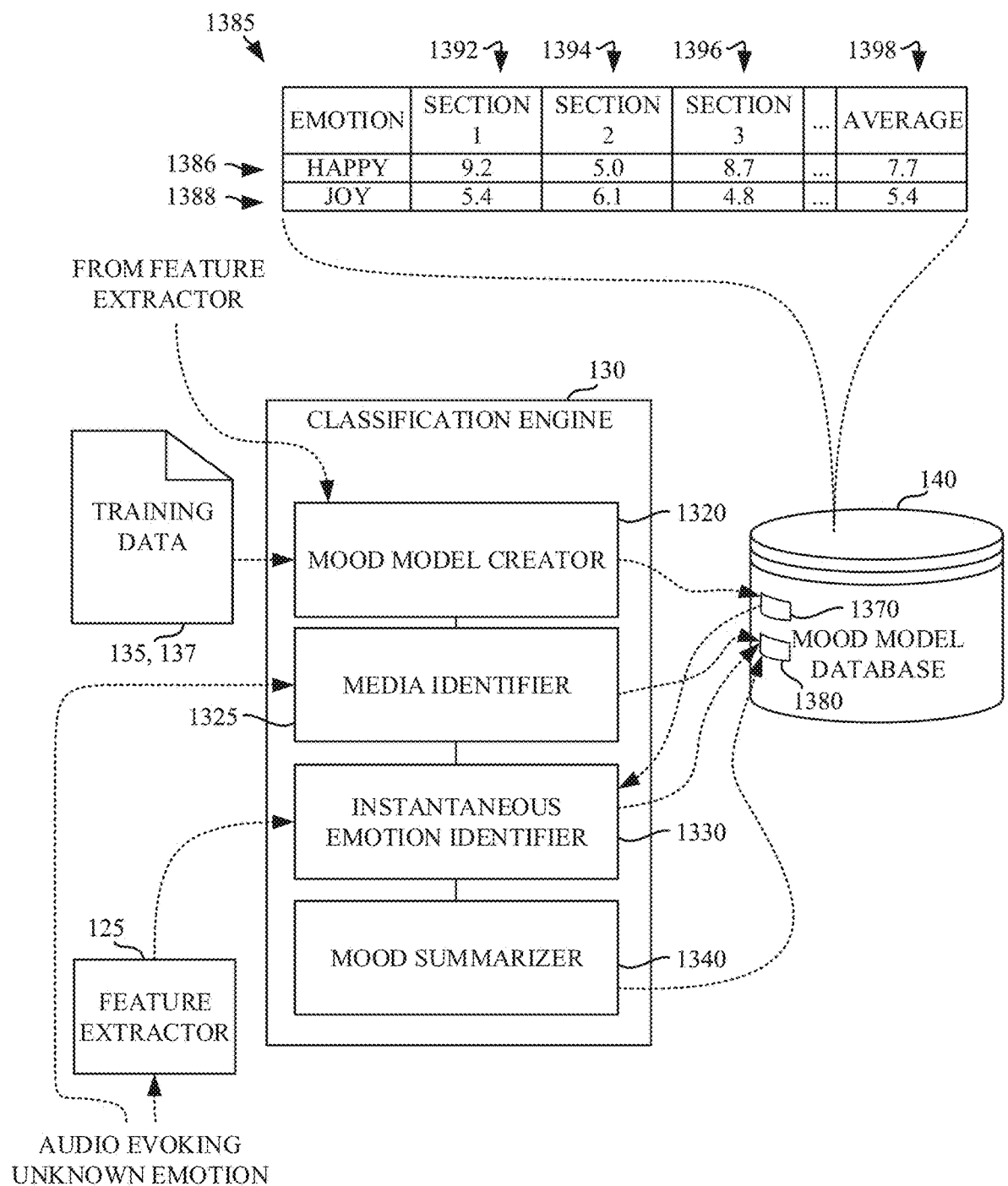
FIG. 13 is a block diagram of an example implementation of the classification engine of FIG. 1.

FIG. 13 is a block diagram of an example implementation of the classification engine 130 of FIG. 1. The example classification engine of the illustrated example of FIG. 13 includes a mood model creator 1320, a media identifier 1325, an instantaneous emotion identifier 1330, and a mood summarizer 1340.

The example mood model creator 1320 of the illustrated example of FIG. 13 is implemented by a logic circuit such as a silicon-based processor executing instructions, but it could additionally or alternatively be implemented by an ASIC(s), a PLD(s), a FPLD(s), an analog circuit, and/or other circuitry. The example mood creator 1320 is used to create a mood model based on training data associating an audio sample with emotion(s) and/or mood(s). As defined herein, training data includes an audio sample and metadata identifying the emotion(s) and/or moods of the corresponding audio. In some examples, additional audio samples are created which correspond to the audio sample of the training data. In such examples, the additional audio samples correspond to the same emotion(s) and/or mood(s) of the audio samples of the training data to which they correspond. The example mood model creator 1320 receives identified features corresponding to an audio sample (e.g., the audio sample of the training data 135, a sample based on the audio sample of the training data 135, etc.) from the feature receiver 125. The example mood model creator 1320 also receives the metadata identifying the emotion(s) and/or mood(s) of the audio sample. The example training data 135 identifies emotions associated with the sample(s) on which the received features are based. In some examples, the example pre-verbal utterance training data 137 is used. In some examples, the example training data 135 is associated with known audio such as musical compositions with one or more pre-classified fields and/or segments. As explained above, some examples disclosed herein use a range of inputs (e.g., pre-verbal utterances and/or known audio) to train the model on sounds mapping to specific emotion(s) and/or mood(s).

Using the features of the audio sample and the known emotional/mood characteristics associated with the audio sample on which the extracted features are based, the mood model creator 1320 of the illustrated example creates a mood model implemented as an artificial neural network. In the illustrated example, the artificial neural network is saved in a mood model location 1370 of the mood model database 140. While in the illustrated example the mood model is implemented using an artificial neural network, any other way of implementing the mood model may additionally or alternatively be used.

The example media identifier 1325 of the illustrated example of FIG. 13 is implemented by a logic circuit such as a silicon-based processor executing instructions, but it could additionally or alternatively be implemented by an ASIC(s), a PLD(s), a FPLD(s), an analog circuit, and/or other circuitry. The example media identifier 1325 receives audio and identifies the media. In the illustrated example, the media identifier 1325 identifies the media using codes and/or signatures as explained above. However, the media may be identified in any other fashion such as, for example, by inspecting metadata associated with the media. The example media identifier 1325 stores an identification of the media in the mood model database 140. The identification of the media enables the example instantaneous emotion identifier 1330 and the example mood summarizer 1340 to store mood and/or emotion data in association with the identified media in a media and emotion data table 1380 within the mood model database 140.

The example instantaneous emotion identifier 1330 of the illustrated example of FIG. 13 is implemented by a logic circuit such as a silicon-based processor executing instructions, but it could additionally or alternatively be implemented by an ASIC(s), a PLD(s), a FPLD(s), an analog circuit, and/or other circuitry. The example instantaneous emotion identifier 1330 of the illustrated example receives identified features of an audio sample. The instantaneous emotion identifier 1330 uses the mood model stored in the mood model database 140 to identify emotion(s) of the audio sample. In the illustrated example, the instantaneous emotion identifier 1330 identifies the emotion(s) conveyed by the audio every ten seconds. That is, the features of the audio sample are stored (e.g., in a circular buffer) in blocks corresponding to ten second intervals of the audio. The instantaneous emotion identifier 1330 of the illustrated example operates on these blocks to classify the emotion(s) of every ten seconds of audio. However, any other audio block size/duration of emotion identification may additionally or alternatively be used. The instantaneous emotion(s) identified by the instantaneous emotion identifier 1330 is stored in the media and emotion data table 1380 in the mood model database 140.

The example mood summarizer 1340 of the illustrated example of FIG. 13 is implemented by a logic circuit such as a silicon-based processor executing instructions, but it could additionally or alternatively be implemented by an ASIC(s), a PLD(s), a FPLD(s), an analog circuit, and/or other circuitry. The example mood summarizer 1340 summarizes the emotion data created by the instantaneous emotion identifier 1330. For example, while a particular piece of media may have many segments that are happy, with a few segments identified as sad, the mood summarizer 1340 may determine that the mood of the media is happy overall. In some examples, the example mood summarizer 1340 identifies one or more emotions that are most present in the audio sample. For example, if an audio sample has a duration of thirty seconds divided into three sections, each of the three sections receives an emotional score for different emotions from the instantaneous emotion identifier 1330. The emotional scores represent an intensity of a particular emotion. For example, a higher emotional score represents a higher intensity and/or presence of the emotion. For example, a happy score of 9.9 indicates that the emotion of happy is more intense than a happy score of 2.3.

An example data table 1385 shown in FIG. 13 illustrates example identifications of scores for media for different emotions at various times during the media. In the illustrated example, three columns 1392, 1394, 1396 representing three sections of the media, and two emotion rows 1386, 1388 representing two emotions being identified are shown. In the illustrated example, the first section 1392 receives a happy score 1386 of 9.2 and a joy score 1388 of 5.4, the second section 1394 receives a happy score 1386 of 5.0 and a joy score 1388 of 6.1, and the third section 1396 receives a happy score 1386 of 8.7 and a joy score 1388 of 4.8. The example mood summarizer 1340 computes an average 1398 for each of the emotions and, in the illustrated example, identifies that the average happy score 1386 is 7.7, while the average joy score 1388 is 5.4. Accordingly, because over time, happy has the highest average, the example mood summarizer 1340 identifies the audio sample as having a mood of happy. However, any other way of identifying a mood of a piece of media may additionally or alternatively be used. For example, the mood summarizer 1340 may identify that the media is ninety percent happy and ten percent sad and, thus, identify the mood of the media as happy. In some other examples, the example mood summarizer 1340 may sort and/or order emotions detected in an audio sample. For example, an audio sample may be identified primarily as happy and secondarily as joyous. Once the mood summarizer 1340 identifies a mood of the piece of media, the mood summarizer of the illustrated example stores the mood in the media and emotion data table 1380 in association with the identified media.

Figure 14:
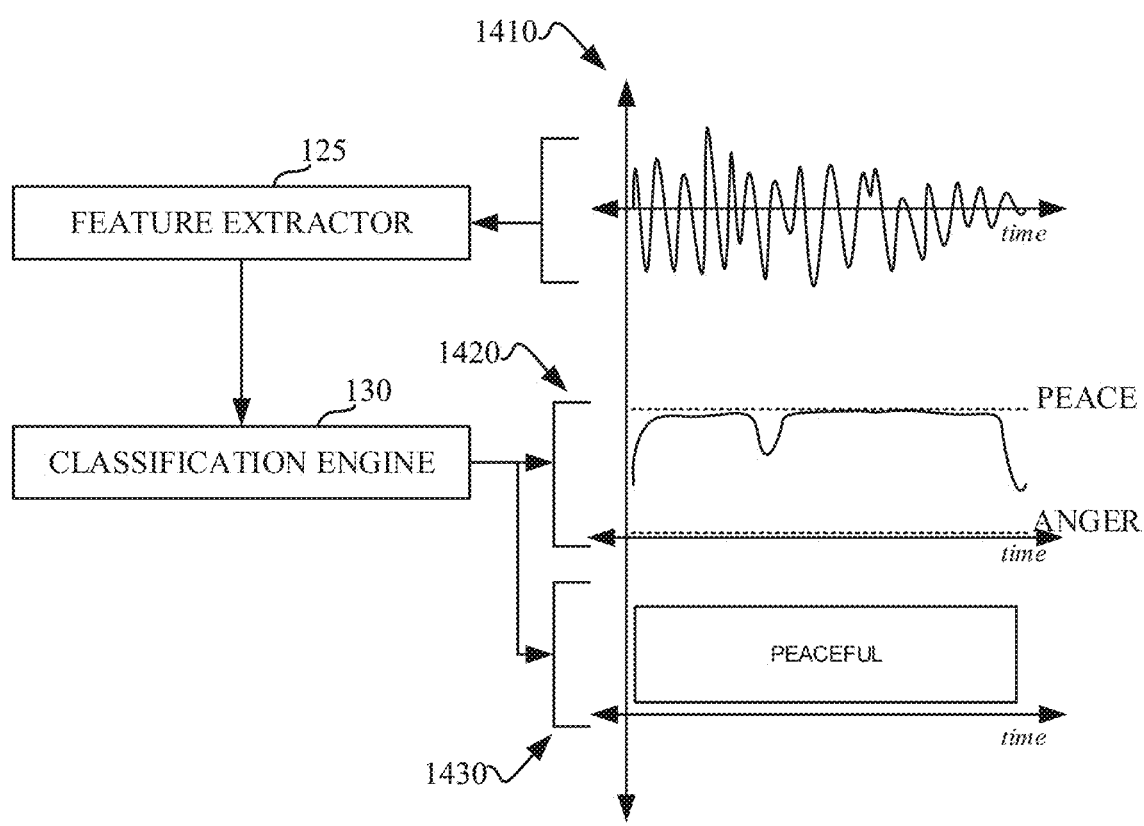
FIG. 14 is an example diagram illustrating an example input to the example feature extractor of FIGS. 1 and/or 3, and an example corresponding output by the example classification engine of FIGS. 1 and/or 13.

FIG. 14 is an example diagram illustrating an example input to the example feature extractor 125 of FIGS. 1 and/or 3, and an example corresponding output by the example classification engine 130 of FIGS. 1 and/or 13. FIG. 14 includes an audio waveform 1410 corresponding to media that evokes an unknown emotion. The audio waveform 1410 is processed by the feature extractor 125 to identify features of the audio waveform 1410. The instantaneous emotion identifier 1330 of the classification engine 130 outputs an instantaneous emotion classification (e.g., happy, sad, etc.) corresponding to the audio waveform 1410. In the illustrated example, the emotional couplet of peace and anger are shown. However, any other emotion(s) may be identified and/or output in any other manner. For example, while in the illustrated example, peace and anger are shown using a single waveform 1420, the emotions of peace and anger may be shown using separate waveforms. Additionally or alternatively, peace and/or anger may not be presented and/or additional or different emotion(s) and/or emotional couplet(s) may be present. The example mood summarizer 1340 of this example summarizes the mood identified by the instantaneous emotion identifier 1330 of the classification engine 130. In the illustrated example, the mood summarizer identifies that the general emotion of the audio waveform 1410 is peaceful 1430.

Figure 15A:
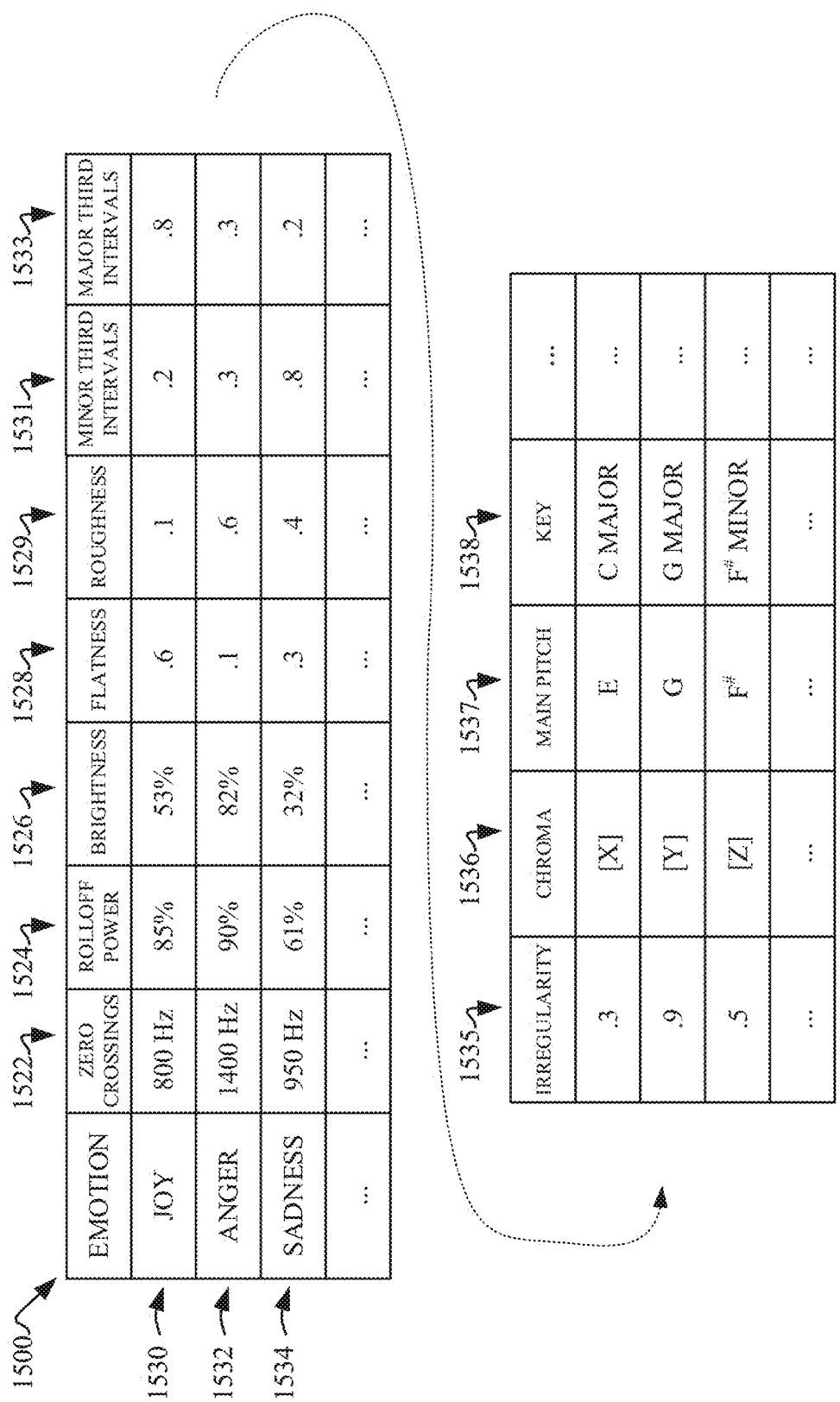

FIG. 15A illustrates an example data table 1500 representing an association of identified audio features with a particular emotion. In some examples, the example data table 1500 represents the example mood model stored in the mood model database 140. For example, the example data table 1500 identifies different emotions (e.g., joy is identified in example row 1530, anger is identified in example row 1532, sadness is identified in example row 1534). In association with each of the emotions, audio features are identified and cataloged. For example, the example zero crossing column 1522 represents zero crossing values identified by the example zero crossing identifier 305 in association with different emotions, the example rolloff power column 1524 represents rolloff power values identified by the example rolloff power identifier 310, the example brightness column 1526 represents brightness values identified by the example brightness identifier 315, the example flatness column 1528 represents flatness values identified by the example flatness identifier 320, the example roughness column 1529 represents roughness values identified by the example roughness identifier 325, the example minor third interval column 1531 represents minor third interval values identified by the minor third interval identifier 330, the example major third interval column 1533 represents major third interval values identified by the major third interval identifier 335, the example irregularity column 1535 represents irregularity values identified by the example irregularity identifier 340, the example chroma column 1536 represents chroma data identified by the example chroma identifier 345, the example main pitch column 1537 represents main pitch values identified by the main pitch identifier 350, the example key column 1538 represents example keys identified by the key identifier 355.

When, for example, the example mood model creator 1310 associates a particular emotion with a set of identified features received from the example feature extractor 125, the example mood model creator 1310 stores the association of the emotion with the set of identified features. For example, if a sample is classified as angry, has a zero crossing value of fourteen hundred (1400) hertz, a rolloff power value of ninety (90) percent, a brightness of eighty two (82) percent, a flatness of one tenth (0.1), a roughness of six tenths (0.6), a presence of minor third intervals of three tenths (0.3), a presence of major third intervals of three tenths (0.3), an irregularity of nine tenths (0.9), a chroma having data Y, a main pitch of G, and a key of G major, the identified emotion of angry and the various values of the identified features are stored (see example row 1532). Later, when attempting to identify an emotion evoked by media, values of features extracted from the media can be compared against values stored in the example data table 1500 to identify an emotion that is most closely correlated to the sample to be identified. A given emotion may have more than one row in the example table of FIG. 15A. For example, if different musicians create different musical interpretations of a pre-verbal utterance, each interpretation will have its own row. Similarly, different pre-verbal utterances (e.g., from different humans) for those emotions may have different row entries in the table. Additionally or alternatively, different pre-recorded samples for different media may correspond to the same emotion and yet have different entries in the table.

When creating the mood model, the example mood model creator 1310 determines a weighting value associated with each feature. Weighting values enable the instantaneous emotion identifier 1330 to identify an intensity of an emotion, thereby enabling differentiation between, for example, media that is very happy versus media that is slightly happy. The example data table 1550 of the illustrated example of FIG. 15B includes a zero crossing column 1560, a zero crossing weight column 1562, a rolloff power column 1564, a rolloff power weight column 1566, a brightness column 1568, a brightness weight column 1570, a flatness column 1572, a flatness weight column 1574, a minor third interval column 1575, a minor third interval weight column 1576, a major third interval column 1577, a major third interval weight column 1578, an irregularity column 1579, an irregularity weight column 1583, a chroma column 1584, a chroma weight column 1585, a main pitch column 1586, a main pitch weight column 1587, a key column 1588, and a key weight column 1589. Later, when attempting to identify an intensity of an emotion evoked by media, values of features extracted from the media can be compared against values and/or weights stored in the example data table 1550 to identify an intensity of an emotion that is most closely correlated to the sample to be identified. For example, to identify the intensity of the emotion, a difference between a calculated feature and a feature for a row of the example table 1550 is computed. In some examples, weighting values are applied to the calculated difference to adjust the impact that the particular feature will have on the resultant score for a particular emotion. In some examples, weighting values are used to effectively zero out a particular feature that is non-determinative because, for example, it appears in multiple emotions, is not a strong indicator of a particular emotion, etc. In some examples, the weighting values for the feature/emotion pair are not fixed and, instead, are implemented as overlapping ranges using fuzzy logic.

The calculated differences (and/or weighted differences) are summarized to form an emotional intensity score. However, any other way of combining the calculated differences (and/or weighted differences) may additionally or alternatively be used to calculate the emotional intensity score such as, for example, averaging the calculated differences and/or weighted differences, etc.

Figure 15C:
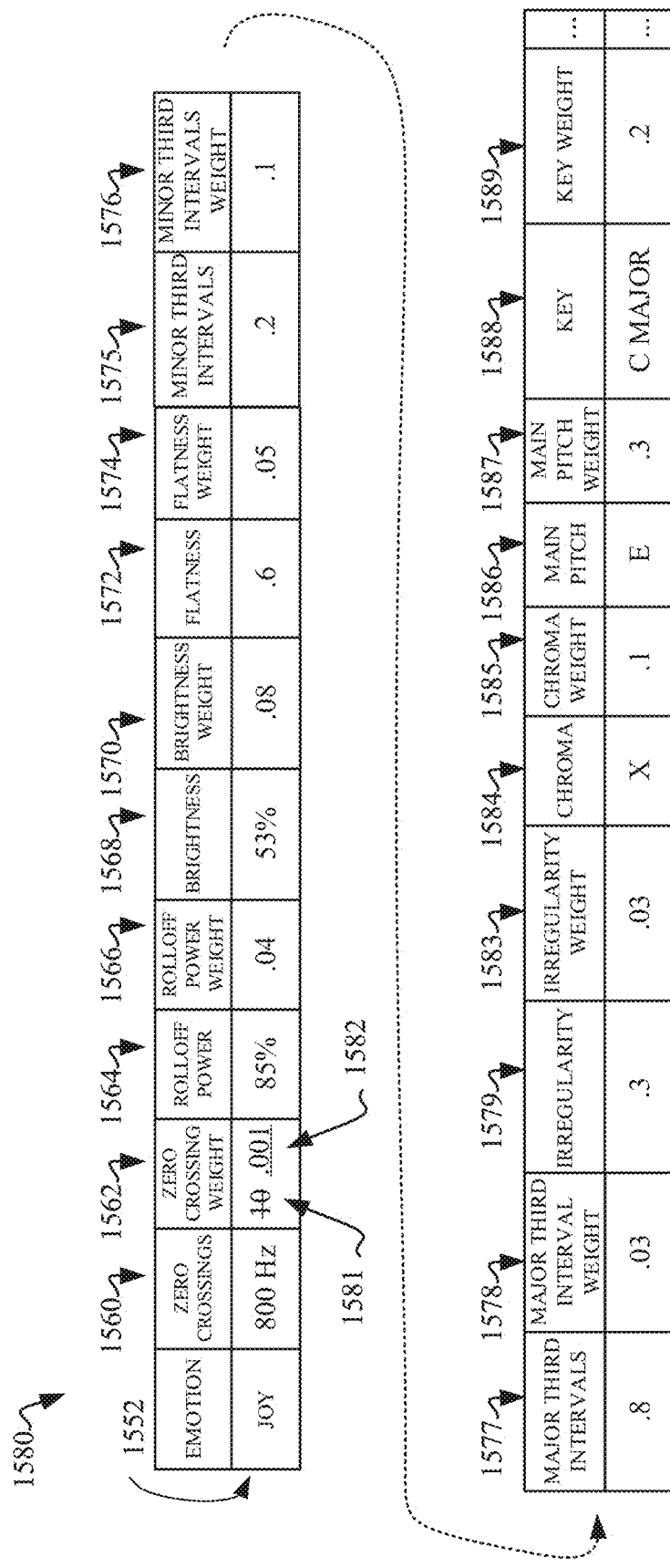

Advantageously, weighting values can be modified by the example mood model creator 1320 during and/or after the mood model creation process. If, for example, the mood model is to be updated, weighting values may be modified in association with the feature and/or emotion to be modified. The example data table 1580 of FIG. 15C shows an example modification of the zero crossing weight value 1562 for the emotion of joy 1552. In the illustrated example, the weighting value is modified from ten (10) 1581 to one thousandth (0.001) 1582, indicating that a zero crossing value is not a strong indicator of the emotion of joy. This effectively zeroes out the effect that zero crossings can have on identifying an emotion. In some examples, the example mood model may be updated by the insertion of additional rows to the example data tables 1500, 1550 to reflect additional associations of emotions and audio features.

In practice, the example data tables 1500, 1550 will include many additional rows and/or columns to, for example, account for other audio features identified by the example feature extractor 125, to account for other emotions to be identified, account for other non-emotion based recommendation parameters (e.g., an applicability of media to a particular environmental context, an applicability of media to a particular activity, a language of the media, etc.) and/or to account for variations in features for a same emotion (intra-emotion variation).

To this later end, multiple rows may be present for a single emotion. For example, multiple different combinations of audio features may be associated with a same emotion. In some examples, an intensity of an emotion is also used. For example, different media identified as happy may exhibit different levels of happiness. As such, different emotions may be rated on a scale of zero to ten (0-10). However, any other rating scale or way of identifying an intensity of an emotion may additionally or alternatively be used. When, for example, multiple rows are present for a single emotion, emotion intensity scores for the various rows may be combined (e.g., by summation, by average, etc.) to identify an emotion intensity for the identified emotion.

Figure 16:
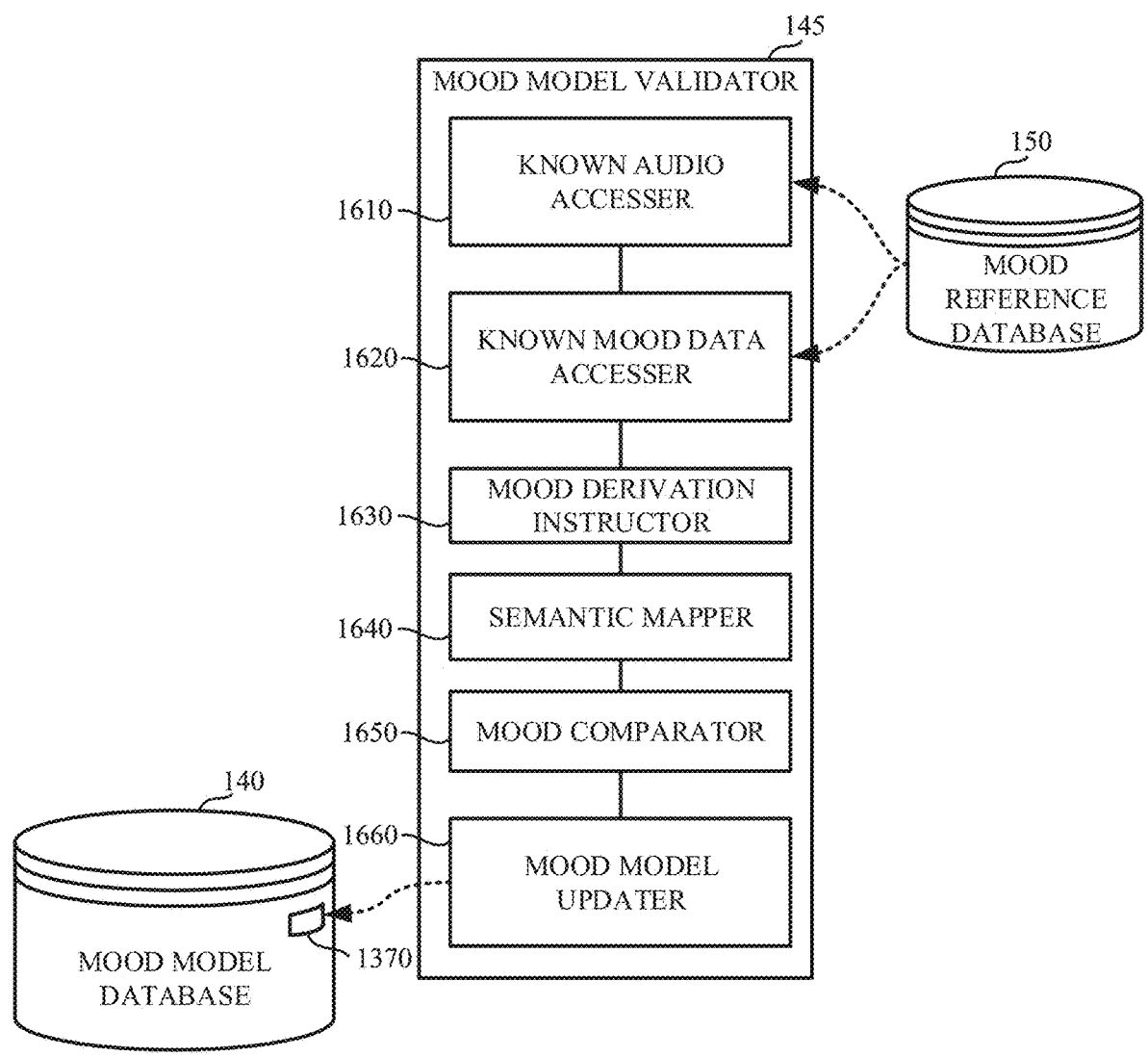
FIG. 16 is a block diagram of an example implementation of the mood model validator of FIG. 1.

FIG. 16 is a block diagram of an implementation of the example mood model validator 145 of FIG. 1. The example mood model validator 145 of FIG. 16 includes an example known audio accesser 1610, an example known mood data accesser 1620, an example mood derivation instructor 1630, an example semantic mapper 1640, an example mood comparator 1650, and an example mood model updater 1660.

The example known audio accesser 1610 of the illustrated example of FIG. 16 is implemented by a logic circuit such as a silicon-based processor executing instructions, but it could additionally or alternatively be implemented by an ASIC(s), a PLD(s), a FPLD(s), an analog circuit, and/or other circuitry. The example known audio accesser 1610 of the illustrated example of FIG. 16 accesses audio from the mood reference database 150 that has known mood and/or emotion data. In examples disclosed herein, the known audio is a recording of known media having a known emotional and/or mood classification. In the illustrated example, the known media is retrieved from a Gracenote™ database. However, any other media type and/or mood reference database may additionally or alternatively be used. In some examples, the example mood reference database 150 is local to the known audio accesser 1610. In some examples, the mood reference database is created based on assessments of emotion(s) and/or mood(s) of the sample audio by a user and/or panel of users.

The example known mood data accesser 1620 of the illustrated example of FIG. 16 is implemented by a logic circuit such as a silicon-based processor executing instructions, but it could additionally or alternatively be implemented by an ASIC(s), a PLD(s), a FPLD(s), an analog circuit, and/or other circuitry. The example known mood data accesser 1620 accesses mood and/or emotion data associated with the media accessed by the known audio accesser 1610 from the mood reference database 150. In the illustrated example, the accessed mood data associates the media with one or more evoked emotion(s) and/or mood(s). In the illustrated example, the accessed mood and/or emotion data uses terms for emotion(s) and/or mood(s) as used by the mood reference database 150.

The example mood derivation instructor 1630 of the illustrated example of FIG. 16 is implemented by a logic circuit such as a silicon-based processor executing instructions, but it could additionally or alternatively be implemented by an ASIC(s), a PLD(s), a FPLD(s), an analog circuit, and/or other circuitry. The example mood derivation instructor 1630 instructs the feature extractor 125 and/or the classification engine 130 to identify an emotion(s) and/or mood(s) associated with the audio having a known emotion(s) and/or mood(s)n using the mood model stored in the mood model database 140. The mood derivation instructor 1630 receives an identification of the identified emotion(s) and/or mood(s) from the classification engine 130.

The example semantic mapper 1640 of the illustrated example of FIG. 16 is implemented by a logic circuit such as a silicon-based processor executing instructions, but it could additionally or alternatively be implemented by an ASIC(s), a PLD(s), a FPLD(s), an analog circuit, and/or other circuitry. Not all mood reference databases 150 use the same emotional and/or mood classification terms. To account for the use of non-matching terms, the semantic mapper 1640 maps terms used by the mood reference database 150 to terms used by the mood model stored in the mood model database 140. For example, when the mood reference database 150 uses the term "easygoing", the semantic mapper 1640 of the illustrated example identifies the known emotion as "peace". In the illustrated example, the semantic map uses a Normalized Google Distance (NGD) between the term used in the mood reference database 150 and the terms used by the mood model to identify when terms should be semantically mapped. However, any other method of semantic mapping may additionally or alternatively be used such as, for example, Explicit Semantic Analysis (ESA), cross-language explicit semantic analysis (CL-ESA), word clouds, etc.

The example mood comparator 1650 of the illustrated example of FIG. 16 is implemented by a logic circuit such as a silicon-based processor executing instructions, but it could additionally or alternatively be implemented by an ASIC(s), a PLD(s), a FPLD(s), an analog circuit, and/or other circuitry. The example mood comparator 1650 compares the emotion(s) and/or mood(s) derived by the classification engine 130 to the emotion(s) and/or mood(s) from the mood reference database 150; as modified by the semantic mapper 1640, if needed. Multiple known media are analyzed to ensure that the mood model accurately identifies emotion(s) and/or mood(s) of media according to known mood reference sources (e.g., the mood reference database 150).

The example mood model updater 1660 of the illustrated example of FIG. 16 is implemented by a logic circuit such as a silicon-based processor executing instructions, but it could additionally or alternatively be implemented by an ASIC(s), a PLD(s), a FPLD(s), an analog circuit, and/or other circuitry. If, for example, the mood comparator 1650 determines that the emotion(s) and/or mood(s) identified by the classification engine 130 does not match the emotion(s) and/or mood(s) suggested by the mood reference database 150 for the corresponding media, the example mood model updater 1660 updates the mood model stored at the mood model location 1370 in the mood model database 140 to account for the mismatch of the derived emotion(s) and/or mood(s). In some examples, the example mood model updater 1660 updates the mood model by adding a row to the example data table 1500 of FIG. 15A including the identified emotion(s) and/or mood(s) of the sample and the identified features associated therewith. In some other examples, the example mood model updater 1660 modifies existing entries in the example data table 1500 of FIG. 15A. While in the illustrated example, the mood model updater 1660 updates the mood model database 140, in some examples, the mood model 1660 updates the training data 135 so that a new mood model may be generated by the mood model creator 1320 of the example classification engine 130 of FIGS. 1 and/or 13.

If, for example, the example mood model comparator 1650 identifies that an emotion and/or mood identified by the classification engine 130 matches and emotion and/or mood suggested by the mood reference database 150 for the corresponding media, the example comparator 1650 stores a record of the alignment of the emotions. In some examples, multiple samples are analyzed and the records of alignment are summarized to represent a correspondence of the mood model to the mood reference database 150. The example mood model may be scrapped and a new mood model created using additional training data (e.g., additional samples, additional emotional identifications of samples in the existing training data, etc.) if, for example, the correspondence of the mood model to the mood reference database is less than a threshold percentage (e.g., 90%, 70%, etc.).

Figure 17:
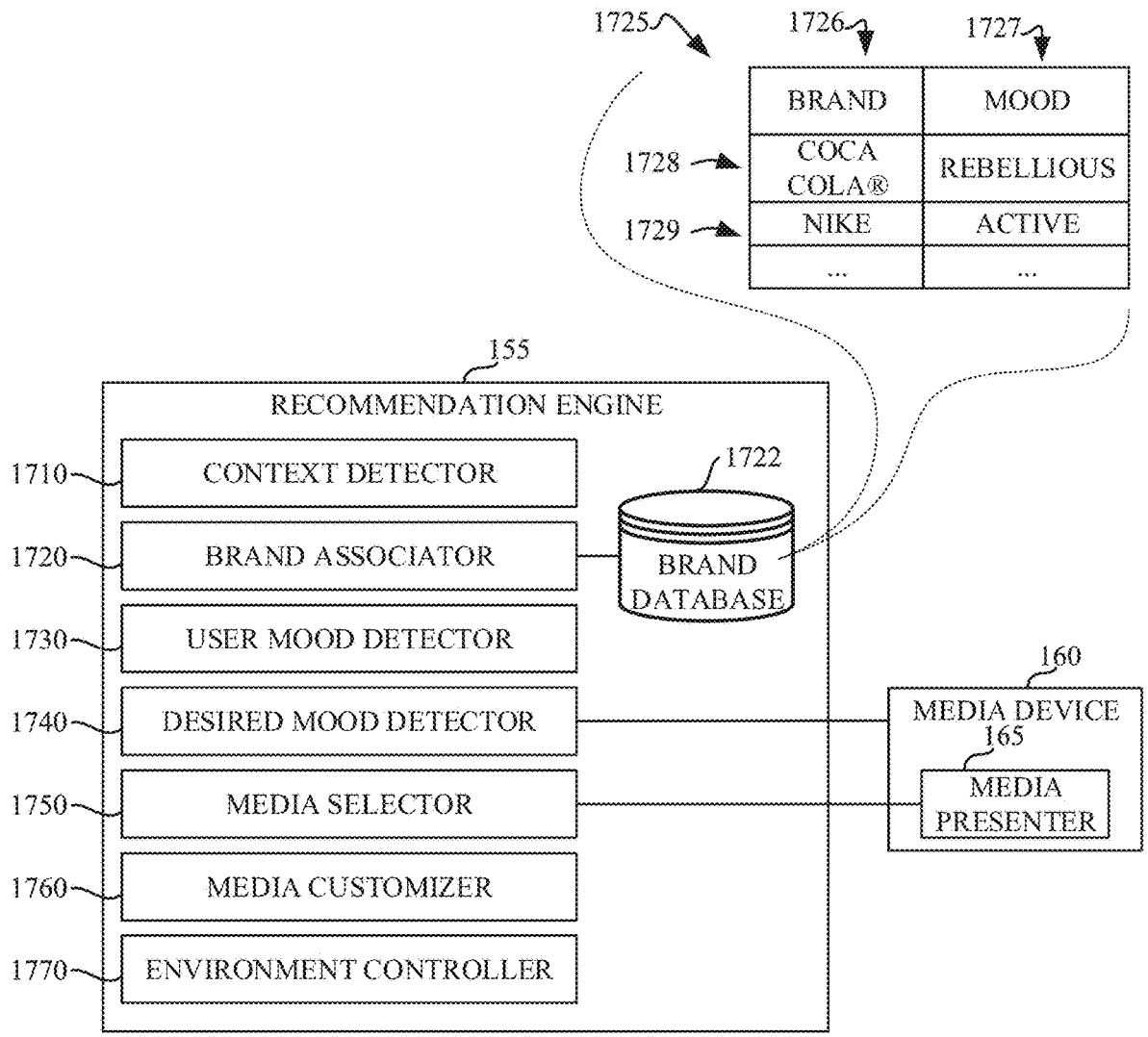
FIG. 17 is a block diagram of an example implementation of the recommendation engine of FIG. 1.

FIG. 17 is a block diagram of an example implementation of the recommendation engine 155 of FIG. 1. The example recommendation engine 155 of the illustrated example of FIG. 17 includes an example context detector 1710, an example brand associator 1720, an example user mood detector 1730, an example desired mood detector 1740, an example media selector 1750, an example media customizer 1760, and example environment controller 1770.

The example context detector 1710 of the illustrated example of FIG. 17 is implemented by a logic circuit such as a silicon-based processor executing instructions, but it could additionally or alternatively be implemented by an ASIC(s), a PLD(s), a FPLD(s), an analog circuit, and/or other circuitry. The example context detector 1710 of the illustrated example of FIG. 17 receives input from one or more sensors 167 of the mobile device 160. The sensor(s) 177 may be, for example, an accelerometer, a temperature sensor, a global positioning system (GPS), a microphone, an altimeter, a gyroscope, an orientation sensor, a magnetic sensor, a light detector, a physiological sensor, a neurological sensor, etc. In examples disclosed herein, the input(s) received from the sensor(s) enable the context detector 1710 to identify an environmental and/or activity context of a user of the media device 160. Environment and/or activity context may be useful for recommending media to a user. For example, if a user is working out, the user's environmental and/or activity context may indicate that media appropriate for a workout such as, for example, an upbeat hip-hop song, would be appropriate. In contrast, a slow classical song might be inappropriate in the context of a workout.

The example brand associator 1720 of the illustrated example of FIG. 17 is implemented by a logic circuit such as a silicon-based processor executing instructions, but it could additionally or alternatively be implemented by an ASIC(s), a PLD(s), a FPLD(s), an analog circuit, and/or other circuitry. In some examples, brands seek to be associated with particular emotion(s) and/or moods. For example a brand that primarily targets a younger audience (e.g., fifteen to twenty five years of age) may desire to be associated with media that is rebellious. As such, the example brand associator 1720 of the illustrated example of FIG. 17 maintains a database 1722 of intended associations of a brand with one or more emotion(s) and/or moods. Such association(s) enable the brand associator 1720 and/or, more generally, the recommendation engine 155 to select media which evokes emotion(s) and/or moods appropriate for the brand. An example data table 1725 that may be stored in the example brand database 1722 is shown in the illustrated example of FIG. 17. The example data table 1725 includes an example brand column 1726 that identifies a brand and an example mood column 1727 that identifies a mood, a trait, and/or an emotion associated with the respective brand. In the illustrated example of FIG. 17, a first example row 1728 identifies that the brand COCA COLA® is associated with a rebellious mood. A second example row 1729 identifies that the brand NIKE® is associated with an active mood.

In the alternative, the association stored in the example brand database 1722 also enables selection of a brand for announcement via an integrated advertisement when a piece of media that evokes the emotion associated with the brand is played. As used herein, an integrated advertisement is defined to be an advertisement that is presented immediately before, after, or during a piece of media (e.g., as an overlaid voiceover and/or audio). In some examples, the integrated advertisement is presented at a volume level greater than that of the media. In some other examples, the integrated advertisement is presented at a volume level softer than that of the media. An example integrated advertisement is "That was Michael Jackson's 'Beat It', brought to you by COCA COLA®."

The example user mood detector 1730 of the illustrated example of FIG. 17 is implemented by a logic circuit such as a silicon-based processor executing instructions, but it could additionally or alternatively be implemented by an ASIC(s), a PLD(s), a FPLD(s), an analog circuit, and/or other circuitry. The example user mood detector 1730 of the illustrated example of FIG. 17 detects a mood of a user of the media device 160. In the illustrated example, the example user mood detector 1730 receives audio of the user's voice via a microphone of the media device 160. In the illustrated example, the example user mood detector 1730 identifies a mood of the user by processing features of a sample of the user's voice obtained by the feature extractor 125 with the classification engine 130 to classify the emotion based on the mood model. However, any other way of identifying a mood of a user may additionally or alternatively be used. For example, the user mood detector 1730 may prompt the user of the media device to indicate their current mood, etc. For example, the user may be requested to transmit a picture of their face, state a current mood, enter their current mood via an input device such as a keypad or a touchscreen, etc. In some examples, Facial Affect Coding (FAC) may be used to infer a mood and/or emotion of the user. In some examples, physiological measurements such as, for example, a galvanic skin response, an electroencephalogram, an electrocardiogram (EKG), etc. are used to infer the mood and/or emotion of the user.

The desired mood detector 1740 of the illustrated example of FIG. 17 is implemented by a logic circuit such as a silicon-based processor executing instructions, but it could additionally or alternatively be implemented by an ASIC(s), a PLD(s), a FPLD(s), an analog circuit, and/or other circuitry. The example desired mood detector 1740 of FIG. 17 identifies the desired mood of a user of the media device 160 based on user input. In some examples, the desired mood detector 1740 periodically prompts the user to identify his/her desired mood. Understanding the user's desired mood and, in some examples, the user's current mood, enables the recommendation engine 155 to recommend media to transition the user from the current mood to the desired mood. For example, if a user's currently in a melancholy mood and the desired mood is one of happiness, media that progresses in mood from melancholy to easy going, to happy may be played over time to gradually adjust the user's mood. Such an approach may be desired over immediately presenting joyful music, which may be jarring to someone in a melancholy mood. In other examples, no attempt to gradually adjust the mood is made. Instead, media matching the desired mood is selected and played immediately. While in the illustrated example, the desired mood is determined by prompting the user, the desired mood may be determined in any other fashion. For example, a preference of the user may be identified based on a user profile (e.g., the user prefers to be melancholy, the user prefers to be happy at a particular time of day, etc.). In some examples, the preference is based on past usage and/or mood/emotion patterns. In some examples, the preference is based on demographic, ethnographic, and/or psychographic profiles used to infer a desired mood and/or emotion of a user.

The example media selector 1750 of the illustrated example of FIG. 17 is implemented by a logic circuit such as a silicon-based processor executing instructions, but it could additionally or alternatively be implemented by an ASIC(s), a PLD(s), a FPLD(s), an analog circuit, and/or other circuitry. The example media selector 1750 of the illustrated example of FIG. 17 recommends media. In the illustrated example, the media selector 1750 selects media that has a smallest (e.g., minimal) difference between the desired emotion and the mood characteristics of the media. As disclosed herein, the difference between a set of one or more emotions of a given piece of media and a desired set of one or more emotions is known as an emotion distance. In the illustrated example, the emotion distance is an aggregate of a difference between emotion scores along various emotions. However, any other function for calculating the emotion distance may additionally or alternatively be used. In the illustrated example, the media selector 1750 selects media having the smallest emotional distance from the set of desired emotions. However, any other method of selecting media may additionally or alternatively be used. For example, particular emotions may be weighted more heavily than others to ensure that those emotions are properly represented in the selected media.

FIG. 18 shows example data that may be used by the example media selector 1750 when selecting media for recommendation. The illustrated example of FIG. 18 includes a set of one or more desired emotions 1810. In the illustrated example, the example set of desired emotions 1810 includes happy 1812, sad 1814, and joyful 1816. In practice, the example set of desired emotions may contain any other emotion(s) and/or parameter(s) for recommending media. The illustrated example of FIG. 18 includes an example table 1820 indicating sets of emotion(s) for various media. The example table includes emotion columns for happy 1822, sad 1824, and joyful 1826. In the illustrated example of FIG. 18, an emotion distance column 1828 is also shown. The example emotion distance column 1828 indicates a sum of differences between the emotion scores for various emotions and the corresponding set of desired emotions. In the illustrated example, three pieces of media are represented: media A 1830, media B 1832, and media C 1834. The example selector calculates a sum of an absolute value of differences along each emotion. For example, an example happy score for media A 1830 is 7.2 and deviates from the desired happy score of 8 by 0.8. The example sad score for media A 1830 deviates from the desired sad score by 0.8. The example joyful score for media A 1830 deviates from the desired joyful score by 1.2. A sum of these differences is represented as the emotion distance (column 1828), and results in an emotion distance of 2.8 for media A 1830. When performing the same calculation for media B 1832, an emotion distance of 6.5 is determined. When performing the same calculation for media C, an emotion distance of 12.8 is determined. Media A 1830 exhibits the smallest emotional distance and, accordingly, is selected for recommendation by the media selector 1750.

Returning to FIG. 17, the example media customizer 1760 of the illustrated example of FIG. 17 is implemented by a logic circuit such as a silicon-based processor executing instructions, but it could additionally or alternatively be implemented by an ASIC(s), a PLD(s), a FPLD(s), an analog circuit, and/or other circuitry. In some examples, media may be customized to fit a particular set of desired emotions. In some examples, the lighting of a commercial is modified by converting and/or re-encoding the commercial with a different lighting setting to convey a different mood and/or emotion. The example media customizer 1760 modifies first media using second media different from the first media to modify or otherwise alter the emotion(s) and/or mood(s) conveyed by the media. For example, a commercial may be modified to include different background music to convey a different desired emotion and/or mood.

The example environment controller 1770 of the illustrated example of FIG. 17 is implemented by a logic circuit such as a silicon-based processor executing instructions, but it could additionally or alternatively be implemented by an ASIC(s), a PLD(s), a FPLD(s), an analog circuit, and/or other circuitry. In some examples, the environment of the user affects the mood of the user. To better facilitate recommendation of media to align with a particular mood, the example environment controller 1770 modifies the environment of the user (e.g., lighting, temperature, scents, etc.).

In the illustrated example, the example environment controller 1770 controls lighting by interfacing with an X10 controller to control light switches and/or dimmers. However, any other standard for lighting control may additionally or alternatively be used such as, for example, Z-wave, Insteon, etc. In the illustrated example, the example environment controller 1770 controls temperature by interfacing with a thermostat and/or Heating, Ventilation, and Air Conditioning (HVAC) system. However, any other ways of controlling lighting, temperature, etc. may additionally or alternatively be used.

Figure 19:
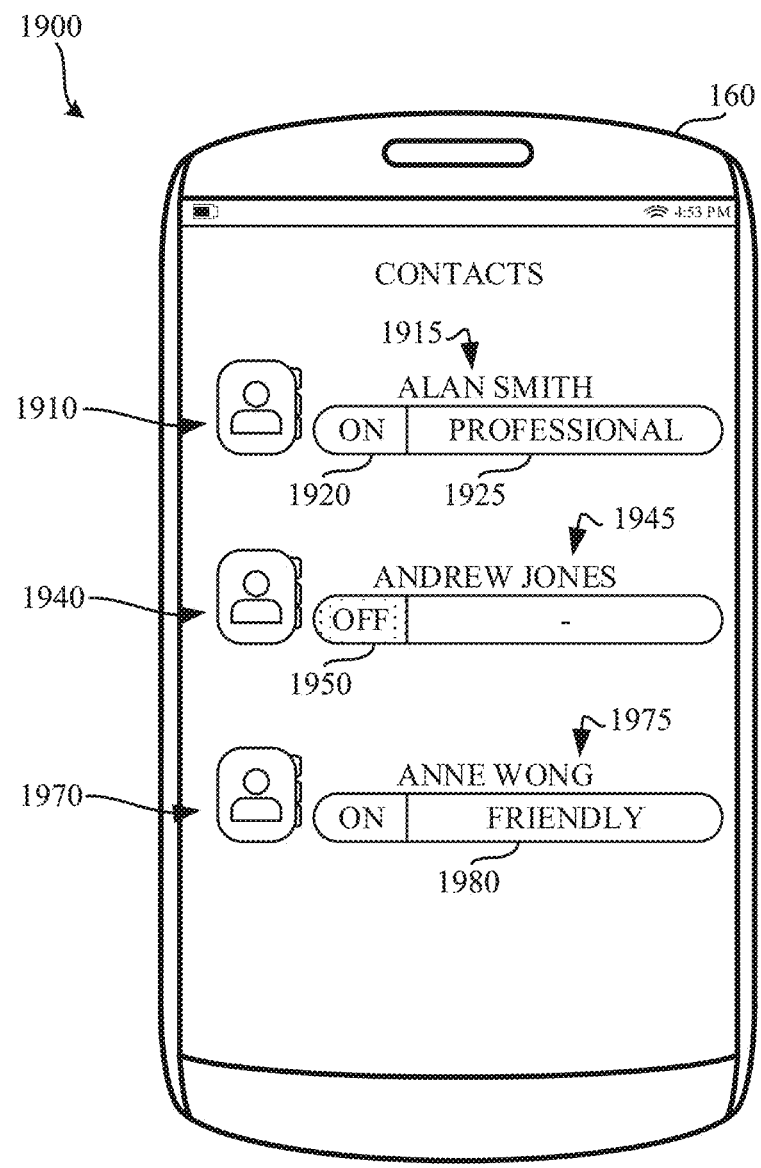
FIG. 19 illustrates an example user interface that may be displayed to indicate a preference for background music to be played during a telephone call with users.

FIG. 19 illustrates an example user interface 1900 that may be displayed by the example media device 160 to indicate a preference for background music to be played during a telephone call with users. The example user interface 1900 includes contact information for three contacts. The first contact 1910 indicates that the preferences apply when a telephone call is conducted with Alan Smith 1915. When the telephone call is conducted with the first contact 1910, background music is to be played as indicated by the switch as "on" 1920, and should set a professional mood as indicated by the "professional" indication in the mood field 1925. The second contact 1940 indicates that no music is to be played when a telephone call is conducted with Andrew Jones as indicated by the switch as "off" 1945. When the telephone call is conducted with the second contact 1940, no background music is to be played and, thus, the mood field is blank. The third contact 1970 indicates that the play music preference applies when a telephone call is conducted with Anne Wong 1975. When the telephone call is conducted with the third contact 1970, background music is to be played, and should set a friendly mood as indicated by the "friendly" indicator in the mood field 1980. The preferences set via the example user interface 1900 enable the example desired mood identifier 1740 of FIG. 17 to identify the desired mood of the user.

Figure 20:
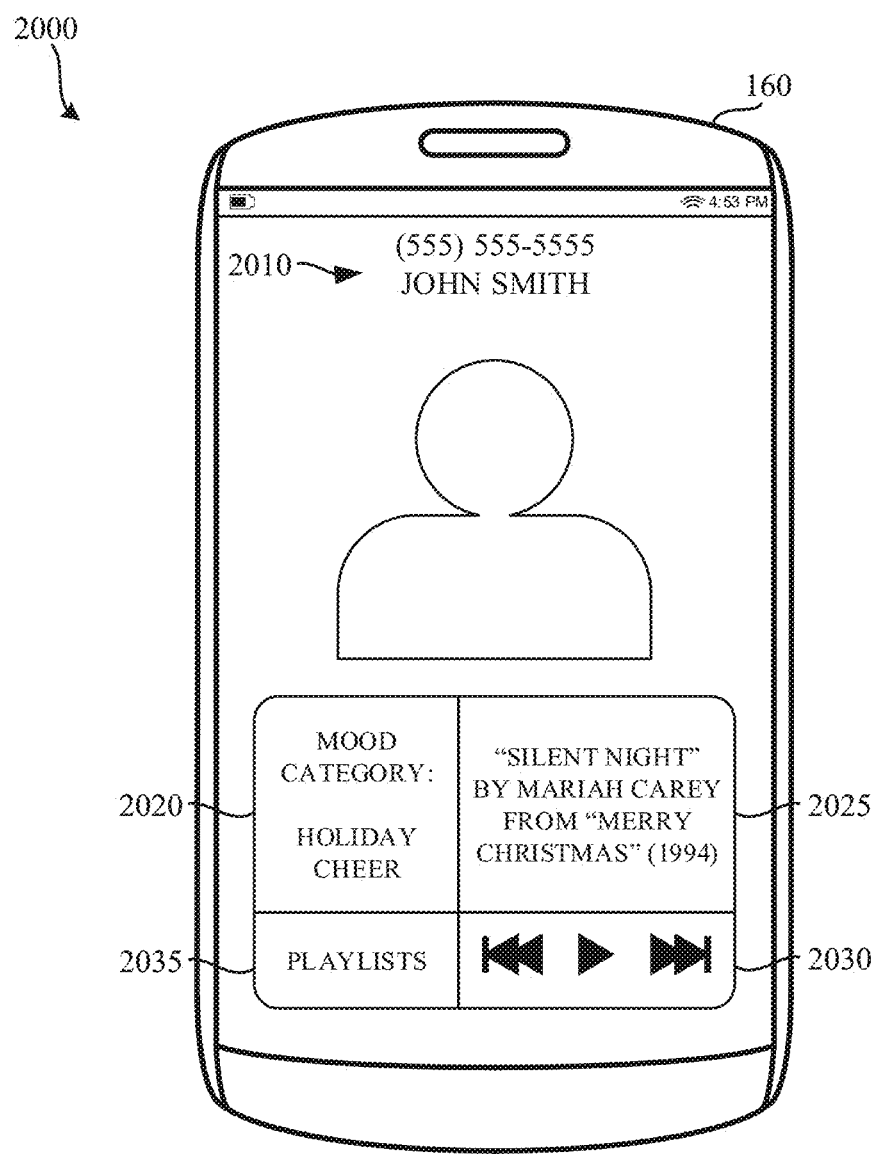
FIG. 20 illustrates an example user interface that may be displayed during a telephone call to enable playback of background music according to a particular mood during a telephone call.

FIG. 20 illustrates an example user interface 2000 that may be displayed by the example media device 160 during a telephone call to enable playback of background music according to a particular mood during a telephone call. The example user interface 2000 of the illustrated example of FIG. 20 identifies a called party 2010. User preferences for the called party 2010 are displayed in a user preferences box 2020. In the illustrated example, the user preferences indicate that background music according to the mood "holiday cheer" should be played. The current media box 2025 displays the current media that is being played. In the illustrated example, the current media is "Silent Night" by Mariah Carey. In the illustrated example, a playlists box 2035 is displayed. The playlist box allows the user to select from other media corresponding to the currently selected mood. In some examples, playlists may be used to enable the user to select particular media that may be presented. In some examples, the user selects media for inclusion in a playlist based on media that is provided from a service provider (e.g., as part of a service). In some examples, the user selects media for inclusion in the playlist based on media that is in the user's personal media library (e.g., local to the media device 160). In some examples, options may additionally or alternatively be provided to the user to enable presentation of only instrumental versions of the media. For example, an option may be provided to enable removal of lyrics from media. A play options box 2030 includes controls to enable the user to control playback of the background music.

While an example manner of implementing the example sample generator 120, the example feature extractor 125, the example classification engine 130, the example mood model validator 145, and/or the recommendation engine 155 of FIG. 1 is/are illustrated in FIGS. 2, 3, 13, 16, and/or 17, one or more of the elements, processes and/or devices illustrated in FIGS. 1, 2, 3, 13, 16, and/or 17 may be combined, divided, re-arranged, omitted, eliminated and/or implemented in any other way. In some examples, different parts of the example system may be independently implemented without the need for other parts to exist. For example, the example recommendation engine 155 may be implemented separately and have access to the trained mood model for providing recommendations. In some examples, the classification engine 130 may be implemented separately. Further, the example audio receiver 115, the example pre-verbal utterance creator 210, the example MIDI notator 220, the example vocoder 230, the example synthesizer 240, the example musician instructor 250, and/or, more generally, the example sample generator 120 of FIGS. 1 and/or 2, the example zero crossing identifier 305, the example rolloff power identifier 310, the example brightness identifier 315, the example flatness identifier 320, the example roughness identifier 325, the example minor third interval identifier 330, the example major third interval identifier 335, the example irregularity identifier 340, the example chroma identifier 345, the example main pitch identifier 350, the example key identifier 355, and/or more generally the example feature extractor 125 of FIGS. 1 and/or 3, the example mood model creator 1320, the example media identifier 1325, the example instantaneous emotion identifier 1330, the example mood summarizer 1340, and/or, more generally, the example classification engine 130 of FIGS. 1 and/or 13, the example mood model database 140, the example known audio accesser 1610, the example known mood data accesser 1620, the example mood derivation instructor 1630, the example semantic mapper 1640, the example mood comparator 1650, the example mood model updater 1660, and/or, more generally, the example mood model validator 145 of FIGS. 1 and/or 16, the example context detector 1710, the example brand associator 1720, the example brand database 1722, the example user mood detector 1730, the example desired mood detector 1740, the example media selector 1750, the example media customizer 1760, the example environment controller 1770, and/or, more generally, the example recommendation engine 155 of FIGS. 1 and/or 17 may be implemented by hardware, software, firmware and/or any combination of hardware, software and/or firmware. Thus, for example, any of the example audio receiver 115, the example pre-verbal utterance creator 210, the example MIDI notator 220, the example vocoder 230, the example synthesizer 240, the example musician instructor 250, and/or, more generally, the example sample generator 120 of FIGS. 1 and/or 2, the example zero crossing identifier 305, the example rolloff power identifier 310, the example brightness identifier 315, the example flatness identifier 320, the example roughness identifier 325, the example minor third interval identifier 330, the example major third interval identifier 335, the example irregularity identifier 340, the example chroma identifier 345, the example main pitch identifier 350, the example key identifier 355, and/or more generally the example feature extractor 125 of FIGS. 1 and/or 3, the example mood model creator 1320, the example media identifier 1325, the example instantaneous emotion identifier 1330, the example mood summarizer 1340, and/or, more generally, the example classification engine 130 of FIGS. 1 and/or 13, the example mood model database 140, the example known audio accesser 1610, the example known mood data accesser 1620, the example mood derivation instructor 1630, the example semantic mapper 1640, the example mood comparator 1650, the example mood model updater 1660, and/or, more generally, the example mood model validator 145 of FIGS. 1 and/or 16, the example context detector 1710, the example brand associator 1720, the example brand database 1722, the example user mood detector 1730, the example desired mood detector 1740, the example media selector 1750, the example media customizer 1760, the example environment controller 1770, and/or, more generally, the example recommendation engine 155 of FIGS. 1 and/or 17 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s) (e.g., a field programmable gate array (FPGA))). When reading any of the apparatus or system claims of this patent to cover a purely software and/or firmware implementation, at least one of the example audio receiver 115, the example pre-verbal utterance creator 210, the example MIDI notator 220, the example vocoder 230, the example synthesizer 240, the example musician instructor 250, and/or, more generally, the example sample generator 120 of FIGS. 1 and/or 2, the example zero crossing identifier 305, the example rolloff power identifier 310, the example brightness identifier 315, the example flatness identifier 320, the example roughness identifier 325, the example minor third interval identifier 330, the example major third interval identifier 335, the example irregularity identifier 340, the example chroma identifier 345, the example main pitch identifier 350, the example key identifier 355, and/or more generally the example feature extractor 125 of FIGS. 1 and/or 3, the example mood model creator 1320, the example media identifier 1325, the example instantaneous emotion identifier 1330, the example mood summarizer 1340, and/or, more generally, the example classification engine 130 of FIGS. 1 and/or 13, the example mood model database 140, the example known audio accesser 1610, the example known mood data accesser 1620, the example mood derivation instructor 1630, the example semantic mapper 1640, the example mood comparator 1650, the example mood model updater 1660, and/or, more generally, the example mood model validator 145 of FIGS. 1 and/or 16, the example context detector 1710, the example brand associator 1720, the example brand database 1722, the example user mood detector 1730, the example desired mood detector 1740, the example media selector 1750, the example media customizer 1760, the example environment controller 1770, and/or, more generally, the example recommendation engine 155 of FIGS. 1 and/or 17 is/are hereby expressly defined to include a tangible computer readable storage device or storage disk such as a memory, a digital versatile disk (DVD), a compact disk (CD), a Blu-ray disk, etc. storing the software and/or firmware. Further still, the example audio receiver 115, the example sample generator 120, the example feature extractor 125, the example classification engine 130, the example mood model database 140, the example mood model validator 145, and/or the example recommendation engine 155 may include one or more elements, processes and/or devices in addition to, or instead of, those illustrated in FIGS. 1, 2, 3, 13, 16, and/or 17, and/or may include more than one of any or all of the illustrated elements, processes and devices.

Flowcharts representative of example machine readable instructions for implementing the example audio receiver 115, the example sample generator 120, the example, feature extractor 125, the example classification engine 130, the example mood model validator 145, the example recommendation engine 155, and/or, more generally, the example mood-based media recommendation system 105 of FIG. 1 are is shown in FIGS. 21, 22, 23, 24, 25, 26, 27, 28, 29, 30, 31, 32, 33, 34, 35, 36, 37, 38, 39, and/or 40. In these examples, the machine readable instructions comprise a program(s) for execution by a processor such as the processor 4112 shown in the example processor platform 4100 discussed below in connection with FIG. 41. The program may be embodied in software stored on a tangible computer readable storage medium such as a CD-ROM, a floppy disk, a hard drive, a digital versatile disk (DVD), a Blu-ray disk, or a memory associated with the processor 4112, but the entire program and/or parts thereof could alternatively be executed by a device other than the processor 4112 and/or embodied in firmware or dedicated hardware. Further, although the example program(s) is/are described with reference to the flowcharts illustrated in FIGS. 21, 22, 23, 24, 25, 26, 27, 28, 29, 30, 31, 32, 33, 34, 35, 36, 37, 38, 39, and/or 40, many other methods of implementing the example audio receiver 115, the example sample generator 120, the example, feature extractor 125, the example classification engine 130, the example mood model validator 145, the example recommendation engine 155, and/or, more generally, the example mood-based media recommendation system 105 of FIG. 1 may alternatively be used. For example, the order of execution of the blocks may be changed, and/or some of the blocks described may be changed, eliminated, or combined.

As mentioned above, the example processes of FIGS. 21, 22, 23, 24, 25, 26, 27, 28, 29, 30, 31, 32, 33, 34, 35, 36, 37, 38, 39, and/or 40 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and transmission media. As used herein, "tangible computer readable storage medium" and "tangible machine readable storage medium" are used interchangeably. Additionally or alternatively, the example processes of FIGS. 21, 22, 23, 24, 25, 26, 27, 28, 29, 30, 31, 32, 33, 34, 35, 36, 37, 38, 39, and/or 40 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and transmission media. As used herein, when the phrase "at least" is used as the transition term in a preamble of a claim, it is open-ended in the same manner as the term "comprising" is open ended.

Figure 21:
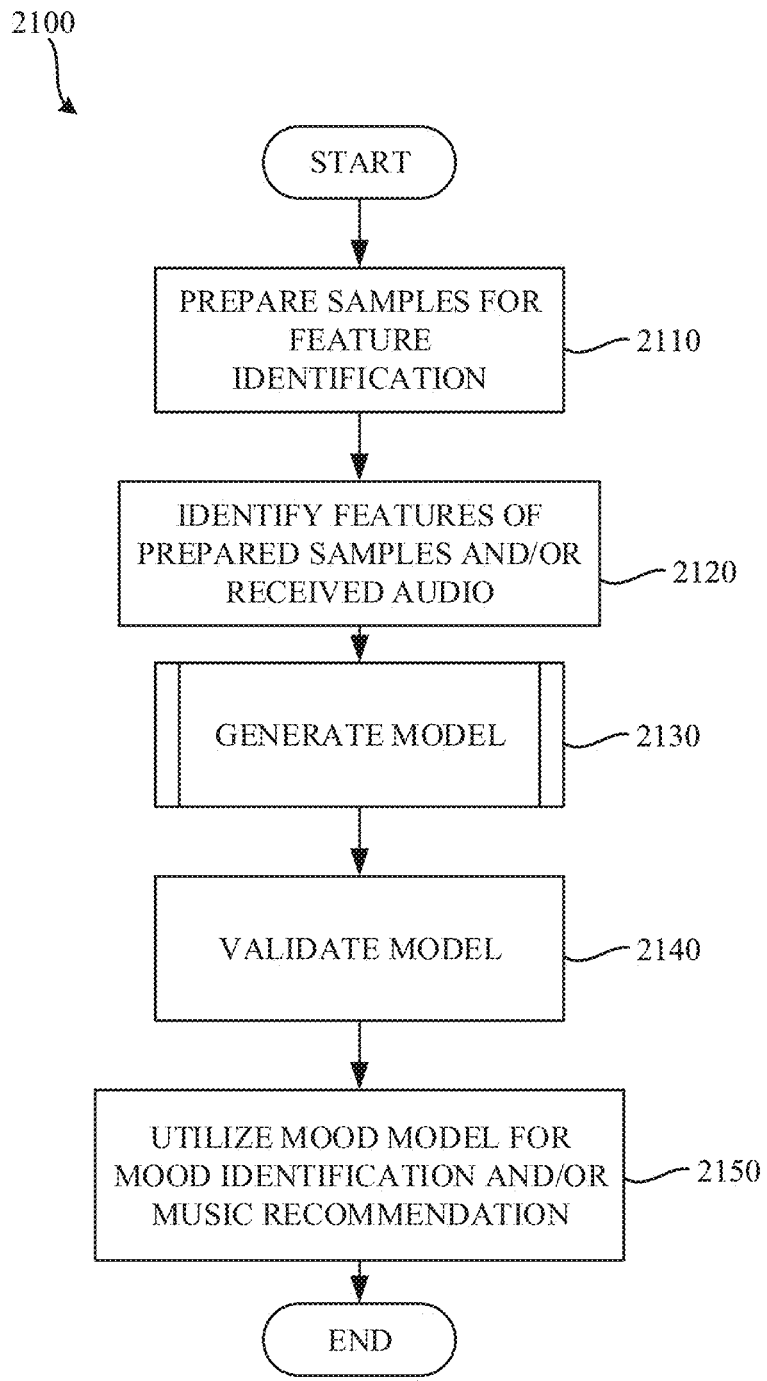
FIG. 21 is a flowchart representative of example machine readable instructions which may be executed to implement the example mood-based media recommendation system of FIG. 1.

FIG. 21 is a flowchart representative of example machine readable instructions 2100 which may be executed to implement the example mood-based media recommendation system 105 of FIG. 1. As disclosed herein, emotion(s) and/or mood(s) are evoked by particular features within pieces of media. However, scientific understanding of how such features affect the human brain is limited. As disclosed herein, the use of a mood model enables linking of the features of media to how such features affect human emotion and/or mood. Audio samples of pre-recorded media (e.g., songs) and/or pre-verbal utterances, MIDI-based versions of the samples, vocoder-based versions of the samples, etc. and their associated known emotional/mood identification are used as training data 135, 137. Using multiple samples that are associated with the same emotion in the training set 135, 137 increases the robustness of the mood model when generated by the classification engine 130.

The example program 2100 of the illustrated example of FIG. 21 begins at block 2110 when the sample generator 120 prepares a sample for feature identification. (block 2110). In some examples, the sample generator 120 creates additional samples (e.g., variants) based on a received sample by using the example pre-verbal utterance creator 210, the example MIDI notator 220, the example vocoder 230, the example synthesizer 240, and/or example musician interpreted/mimicked samples. Creating variant samples based on a received sample enables identification of additional features by the feature extractor 125 which correlate to the same emotion (e.g., joy), resulting in a more accurate mood model created by the classification engine 130. In some examples, the samples are implemented as snippets of songs (e.g., portion(s) of songs such as a few seconds) or other pre-existing samples that are selected for their emotional/mood content by, for example, a user, a panel of users, expert listeners, etc. Once the samples have been prepared, the example feature extractor 125 identifies features of the prepared samples and/or the received sample. (block 2120). In the illustrated example, the example feature extractor 125 identifies features such as, for example, zero crossings, rolloff power, brightness, flatness, roughness, minor third intervals, major third intervals, irregularity, chroma, main pitch, key, etc. However, any other features may additionally or alternatively be identified such as, tempo, articulation, pitch, etc. In the illustrated example, audio features are computed for blocks or samples corresponding to small time windows (e.g., a ten second window). However, any other time window may additionally or alternatively be used such as, for example, twenty-five milliseconds, one hundred milliseconds, thirty seconds, etc. Using the identified features, the example classification engine 130 trains an artificial neural network to associate the identified audio features with the emotions associated with the samples on which the features were based. In the illustrated example, the classification engine 130 selects weighting factors that represent a correlation between particular features and/or values of those features and a particular emotion/mood. Example weighting factors are shown in the example data table 1550 of the illustrated example of FIG. 15B. The artificial neural network is stored as the mood model in the mood model database 140. While in the illustrated example, the mood model is implemented as an artificial neural network, the mood model may be implemented in any other fashion. For example, the mood model may be implemented as a lookup reference table as shown in FIG. 15B.

The example mood model validator 145 validates the stored mood model. (block 2140). In the illustrated example, the example mood model validator 145 validates the mood model by instructing the example classification engine 130 to use the mood model to determine a mood of known media having a known mood (e.g., a mood is already identified in the mood reference database 150). In the illustrated example, the mood model validator 145 accesses the known mood classification of the known media. The example mood model validator 145 compares the mood identified by the classification engine 130 against the known mood accessed from the mood reference database 150. In some examples, the example mood model validator 145 updates the mood model by inserting and/or updating additional rows in the to the example data table 1500 of the example of FIG. 15A to account for misalignment of the derived mood and the reference mood from the mood reference database 150. In a neural network model, this would lead to modification of the bias or weighting of the different nodes in the neural network. In some examples, modifying and/or updating the neural network involves the addition or removal of nodes in the neural network. In some examples, the number of nodes at each layer of the neural network is modified and/or the number of layers in the neural network is modified. In some examples, the example mood model validator 145 modifies a weighting value for a particular feature, such as the example weighting values of the example data table 1550 of FIG. 15B. For example, if a correlation is discovered suggesting that rolloff power of a particular value tends to be a leading indicator of a sorrow, the weighting value for rolloff power as associated with sorrow may be increased to indicate the correlation.

Once the mood model is validated, the example recommendation engine 155 utilizes the mood model for mood identification and/or media recommendation. (block 2150). As disclosed herein, the mood model may be utilized for any number of different purposes. For example, the example mood model may be used to provide consumer music experiences, suggestions of media in association with a brand, provide feedback to musician and/or composers about emotions evoked by media they have created, etc. In some examples, a mood-based music search engine may be provided to enable recommendation of music based on a mood, enable identification of a mood of a user based on the music to which they are listening or have listened to, etc. In some examples, music may be streamed based on the desired mood and/or other user characteristics. In some examples, a mood of a user is identified and media associated with the mood of the user is presented.

In some examples, the example recommendation engine 155 recommends media in association with printed literature and/or an electronic book. For example, e-book segments can be identified and emotion-appropriate music can be played to enhance emotion evoking segments of particular pieces of the literature. For example, the text of the e-book may be analyzed to identify a mood evoked by the passage. In some examples, metadata associated with the text is analyzed to identify the mood. In response to such identification, media may be selected to match the identified mood. In some examples, musical features are synchronized to various e-book passages based on emotions evoked by such passages.

In some examples, emotion enhancing musical features can be used to provide physiologically and/or neurologically-based therapeutic support. For example, subjects exhibiting hypertension may be presented with media evoking a calm emotion. The calming emotion of the media, in some examples, may calm and/or relax the subject, thereby relieving the symptoms of the hypertension.

In some examples, the example recommendation engine 155 is used to enhance a brand. The human brain is typically emotionally engaged in charitable acts that correspond to dopamine-serotonin levels. In some examples, a brand may donate to a cause based on a number of listeners to media associated with such cause within a given time period. Listeners may select their favorite cause and listen to media associated with such cause. At particular times, the cause, the brand, and/or a level of donation to the cause may be announced to the user. Users may look forward to particular announcements, thereby causing a corresponding change in the dopamine-serotonin levels of the user.

In some media presentation scenarios, media is reduced in length to correspond with a length of a commercial, scene, ringtone, etc. In some examples, media may be reduced to fit in a shorter allotted time span for, for example, presentation via different media channels (e.g., radio, online, mobile, television, etc.). Such reduction is often performed manually. However, the reduced media may not be optimal for its desired purpose. As such, the example recommendation engine 155 may recommend particular passages of media for use in a particular scenario (e.g., an advertisement, a scene, a ringtone, etc.) by identifying small segments of media (e.g., a ten second period of a song, a thirty second period of a song, etc.) that evoke a particular emotion.

Figure 22:
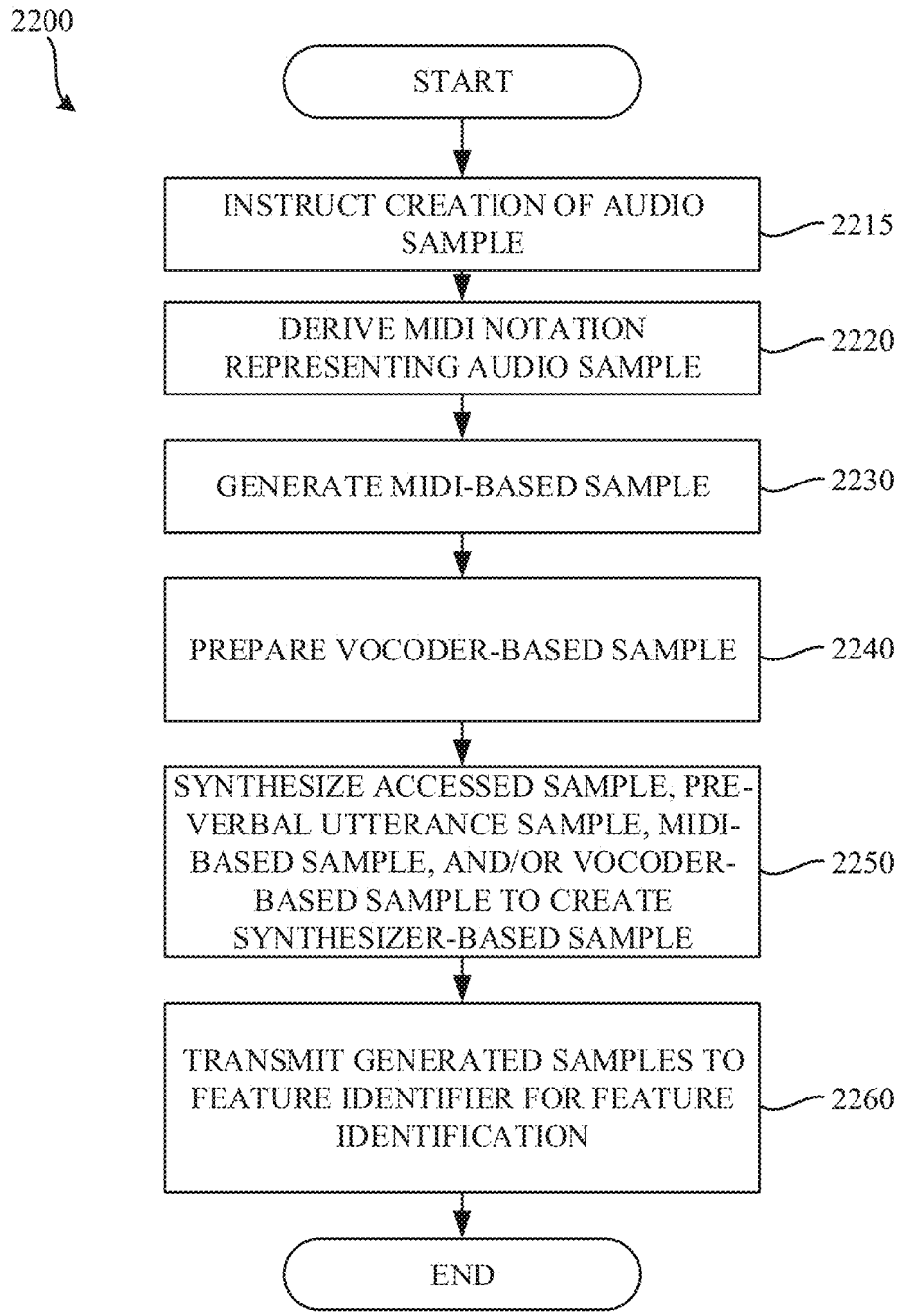
FIG. 22 is a flowchart representative of example machine readable instructions which may be executed to implement the example sample generator of FIGS. 1 and/or 2.

FIG. 22 is a flowchart representative of example machine readable instructions 2200 which may be executed to implement the example sample generator 120 of FIGS. 1 and/or 2. Moreover, FIG. 22 represents example machine readable instructions 2200 that may be executed to implement block 2110 of FIG. 21. Creating a mood model having many samples correlated with a same particular emotion is beneficial in that the resulting mood model can identify many different audio features as mapping to specific emotion(s) and/or mood(s). To that end, the example sample generator 120 prepares variant samples for feature identification in association with a particular emotion or set of emotions. In this example, pre-verbal utterances are used to create the variant samples. However, pre-recorded media with known emotion/mood characteristics could additionally or alternatively be used. The example program 2200 of the illustrated example of FIG. 22 begins when the example pre-verbal utterance creator 210 instructs a person to create a pre-verbal utterance representative of a specific emotion (e.g., a scream). (block 2215).

The example MIDI notator 220 then derives a midi notation representing the pre-verbal utterance. (block 220). In the illustrated example, the MIDI notator 2220 then generates a MIDI-based sample. (block 2230).

The example vocoder 230 prepares a vocoder-based sample. (block 2240). The example vocoder 230 prepares the vocoder-based sample by filtering and synthesizing the MIDI-based sample. However, the vocoder-based sample may be created in any other fashion.

The example synthesizer 240 then the synthesizes vocoder-based sample to create a synthesizer-based sample. (block 2250). In the illustrated example, the synthesizer 240 creates the synthesizer-based sample using a simulated musical instrument (e.g., a trumpet, a saxophone, etc.). The example synthesizer 240 then transmits the generated samples to the feature identifier 125 for feature identification (block 2260). In some examples, samples may be created in any other fashion. For example, the MIDI-notator may be omitted from the sample creation (e.g., the synthesized sample is based on vocoder-based representation of a pre-verbal utterance). In some examples, samples other than pre-verbal utterances are used such as, for example, a song, an audio clip, etc.

In some examples, the example musician instructor 250 instructs a musician to interpretively re-compose a sample using their own creativity (e.g., a sample based on known audio, a sample based on the pre-verbal utterance, a synthesized sample, etc.). In examples disclosed herein, the musicians are presented with a sample and asked to re-compose the sample. In some examples, the musicians are constrained in a manner to not stray too far from a sample to be re-composed. Allowing the musicians to re-compose the synthesized sample into another form re-enforces the connection between composed music and the emotion on which the pre-verbal utterance used to create the composed music is based. The re-composed audio may then be used as an example reference for conveying an emotion and/or mood. In some examples, the example musician instructor 250 instructs the example musician 251 to re-compose the sample based on the synthesized sample (e.g., after the synthesizer 240 has created a synthesized sample in block 2250).

Figure 23:
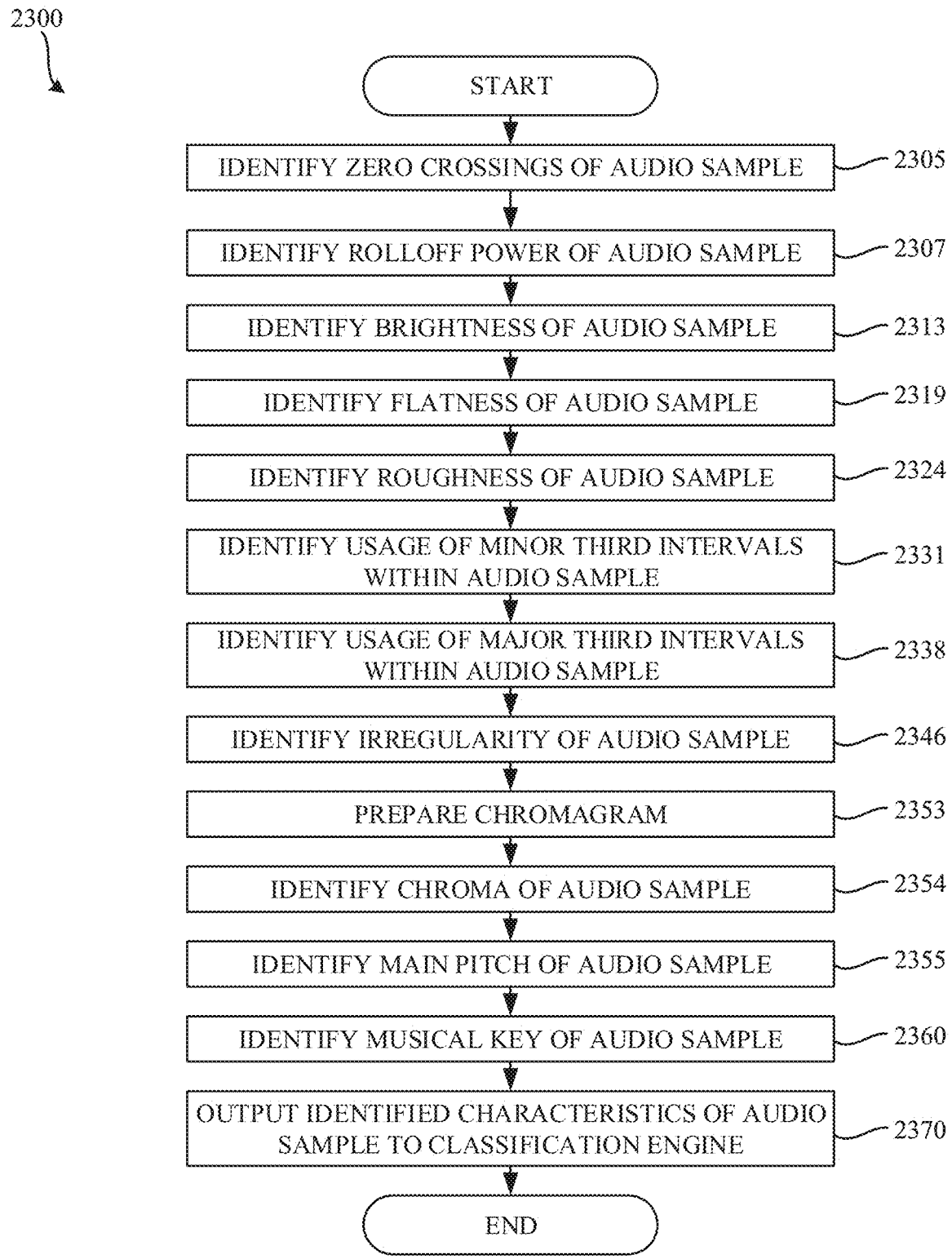
FIG. 23 is a flowchart representative of example machine readable instructions which may be executed to implement the example feature extractor of FIGS. 1 and/or 3.

FIG. 23 is a flowchart representative of example machine readable instructions 2300 which may be executed to implement the example feature extractor 125 of FIGS. 1 and/or 3. Moreover, FIG. 23 represents example machine readable instructions 2200 that may be executed to implement block 2120 of FIG. 21. In each of FIGS. 23A, 23B, 23C, 23D, 23E, 23F, 23G, 23H, and 23I, the determined factor is written to a corresponding field in a row of a table such as, for example, the example data table 1550 of FIG. 15B.

The example program 2300 of the illustrated example of FIG. 23 begins when the zero crossing identifier 305 identifies a zero crossing of a received sample. (block 2305). In the illustrated example, the example zero crossing identifier 305 identifies a count of zero crossings (e.g., instances where an amplitude of the time-domain audio signal is zero) during a given time period. The example zero crossing identifier 305 represents the count of the zero crossings during the time period in hertz. However, the zero crossings may be identified and/or represented in any other way.

Figure 23A:
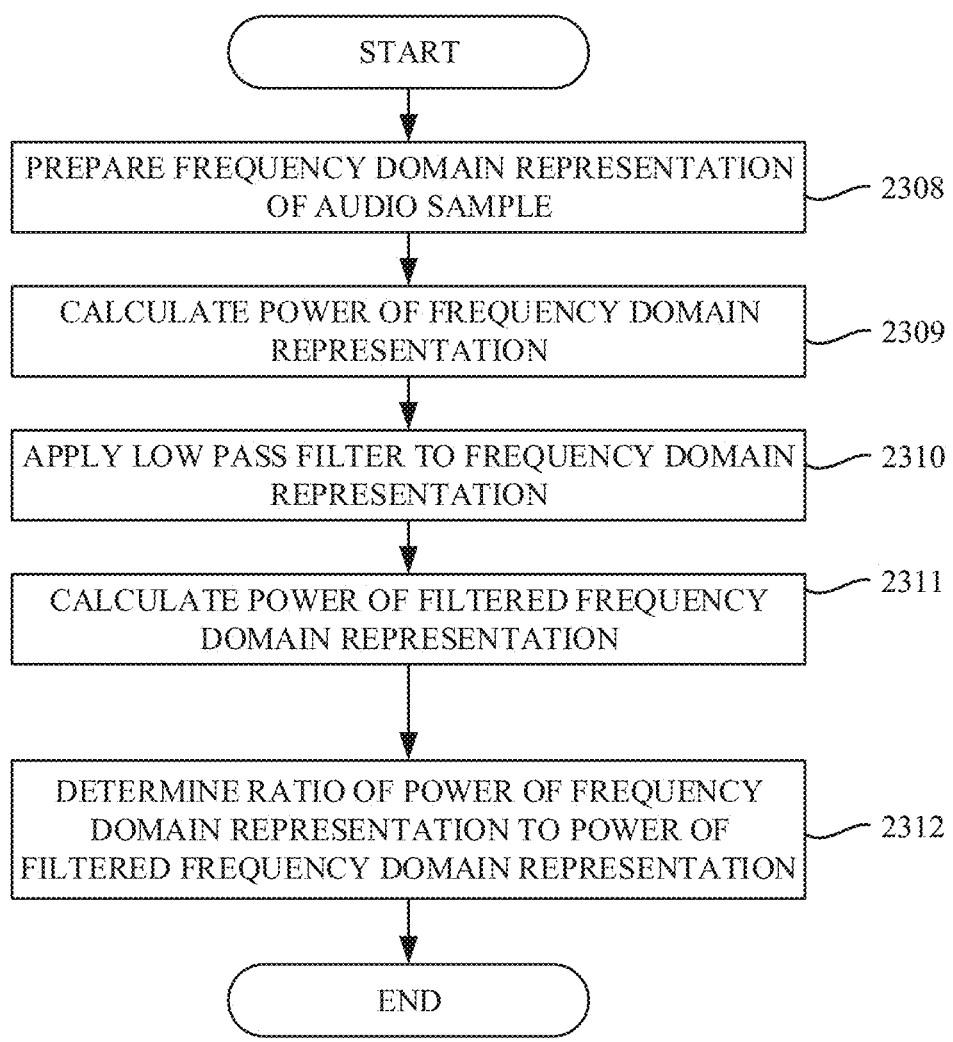
FIGS. 23A, 23B, 23C, 23D, 23E, 23F, 23G, 23H, and 23I are flowcharts representative of example machine readable instructions which may be executed to implement the example feature extractor of FIGS. 1 and/or 3 to identify various features of an audio sample.

The example rolloff power identifier 310 identifies a rolloff power of the sample. (block 2310). FIG. 23A is a flowchart representative of example machine readable instructions which, when executed cause the example rolloff power identifier 310 to identify the rolloff power. The example program of FIG. 23A begins when the example rolloff power identifier 310 prepares a frequency domain representation of a received audio sample. (block 2308). In the illustrated example, the frequency domain representation is prepared by applying a Fourier transform to the audio. However, the frequency domain may be prepared in any other fashion. The example rolloff power identifier 310 calculates a power of the frequency domain representation. (block 2309). The example rolloff power identifier 310 applies a low pass filter to the frequency domain representation to prepare a filtered frequency domain representation. (block 2310). The example rolloff power identifier 310 calculates a power of the filtered frequency domain representation (block 2311). A ratio of powers of the filtered frequency domain representation and the frequency domain representation is created by the rolloff power identifier (block 2312). The power ratio is output (e.g., written to a data table, etc.) as the detected rolloff power of the audio sample. However, the example rolloff power identifier 310 may identify the rolloff power in any other fashion.

Figure 23B:
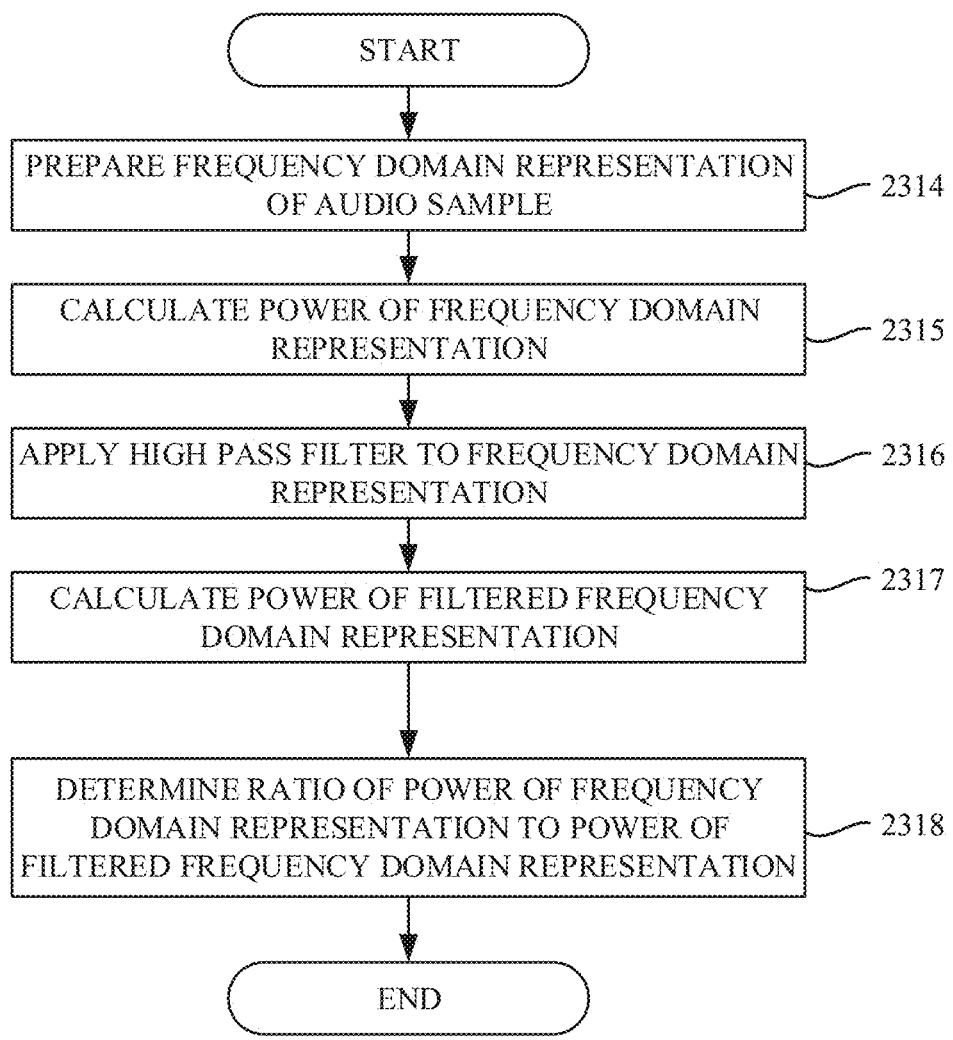

The example brightness identifier 315 identifies a brightness of the received sample. (block 2313). In the illustrated example, the brightness is identified by determining a percentage of a power of a frequency spectrum of the sample that is above a threshold frequency. FIG. 23B is a flowchart representative of example machine readable instructions which, when executed cause the example brightness identifier 315 to identify the brightness. The example program of FIG. 23B begins when the example brightness identifier 315 prepares a frequency domain representation of a received audio sample. (block 2314). In the illustrated example, the frequency domain representation is prepared by applying a Fourier transform to the audio. However, the frequency domain representation may be prepared in any other fashion. The example brightness identifier 315 calculates a power of the frequency domain representation. (block 2315). The example brightness identifier 315 applies a high pass filter to the frequency domain representation to prepare a filtered frequency domain representation. (block 2316). The example brightness identifier 315 calculates a power of the filtered frequency domain representation (block 2317). A ratio of powers of the filtered frequency domain representation and the frequency domain representation is created by the brightness identifier 315 (block 2318). The power ratio is output (e.g., written to a data table, etc.) as the detected brightness of the audio sample. However, the example brightness identifier 315 may identify the brightness in any other fashion.

Figure 23C:
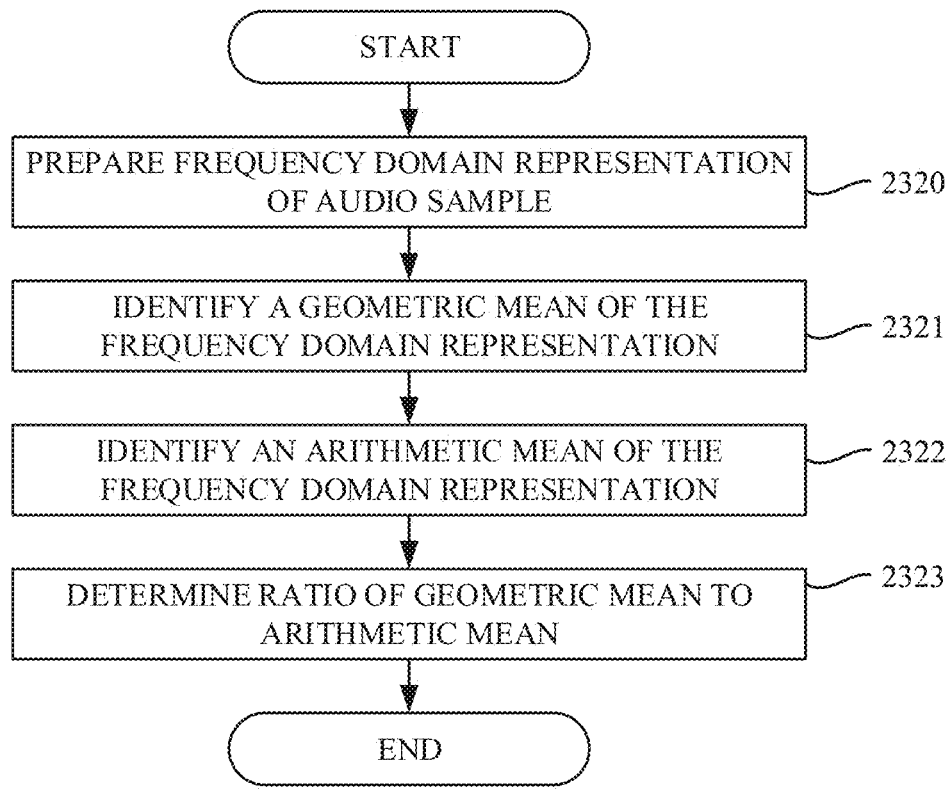

The example flatness identifier 320 identifies a flatness of the received sample. (block 2325). The example flatness identifier 320 identifies the flatness by measuring a spectral flatness in decibels that represents a quantification of noise present in a signal versus distinct tones. FIG. 23C is a flowchart representative of example machine readable instructions which, when executed cause the example flatness identifier 320 to identify the flatness. The example program of FIG. 23C begins when the example flatness identifier 320 prepares a frequency domain representation of a received audio sample. (block 2320). In the illustrated example, the frequency domain representation is prepared by applying a Fourier transform to the audio sample. However, the frequency domain representation may be prepared in any other fashion. The example flatness identifier 320 calculates a geometric mean of the frequency domain representation. (block 2321). As defined herein, the geometric mean indicates the central tendency or typical value of a set of numbers by using a product of their values. The example flatness identifier 320 calculates an arithmetic mean of the frequency domain representation. (block 2322). As defined herein, the arithmetic mean indicates the central tendency or typical value of a set of numbers by using a sum of their values (as distinguished from the product used by the geometric mean). The example flatness identifier 320 determines a ratio of the geometric mean and the arithmetic mean. (block 2323). The ratio is output (e.g., written to a data table, etc.) as the detected flatness of the audio sample. However, the example flatness identifier 320 may identify the flatness in any other fashion.

Figure 23D:
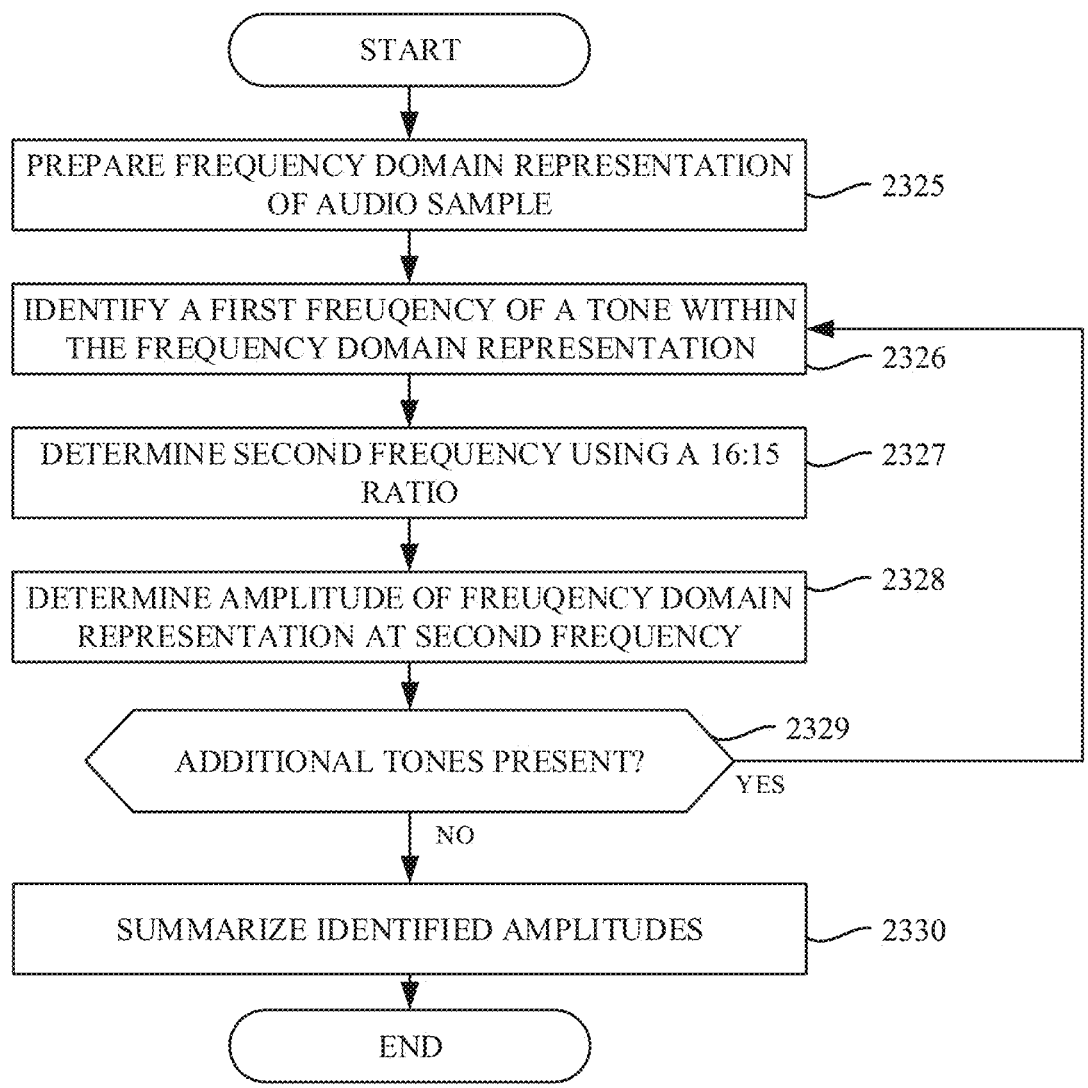

The example roughness identifier 325 identifies a roughness of the sample. (block 2325). In the illustrated example, the roughness is identified by determining a power of dissonant frequencies and/or dissonant tonal intervals within the audio sample. FIG. 23D is a flowchart representative of example machine readable instructions which, when executed cause the roughness identifier 325 to identify the roughness. The example program of FIG. 23D begins when the example roughness identifier 325 prepares a frequency domain representation of a received audio sample. (block 2325). In the illustrated example, the frequency domain representation is prepared by applying a Fourier transform to the audio sample. However, the frequency domain representation may be prepared in any other fashion. The example roughness identifier 325 identifies a first frequency of a tone within the frequency domain representation. (block 2326). In the illustrated example, frequencies are identified when they exhibit an amplitude above a threshold amplitude. The example roughness identifier 325 determines a second frequency having a ratio of sixteen to fifteen (16:15) with respect to the first frequency. (block 2327). For example, if the first frequency is fifteen hundred hertz, the second frequency is identified to be sixteen hundred hertz. The example roughness identifier 325 determines an amplitude of the frequency domain representation at the second frequency. (block 2328). The presence of high amplitude tones at a ratio of sixteen to fifteen represents the presence of dissonant tones in the audio sample. The example roughness identifier 325 determines whether additional tones are present in the sample by, for example, determining if any other tones exhibit an amplitude above the amplitude threshold. (block 2329). If additional tones are present, control proceeds to block 2326, where the frequency of the tone is identified. If no additional tones are present, the amplitude(s) of detected dissonant intervals are summarized. The summarized amplitudes are output (e.g., written to a data table, etc.) as an indicator of the presence of dissonant tones in the sample. However, the example roughness identifier 325 may identify the roughness in any other fashion.

Figure 23E:
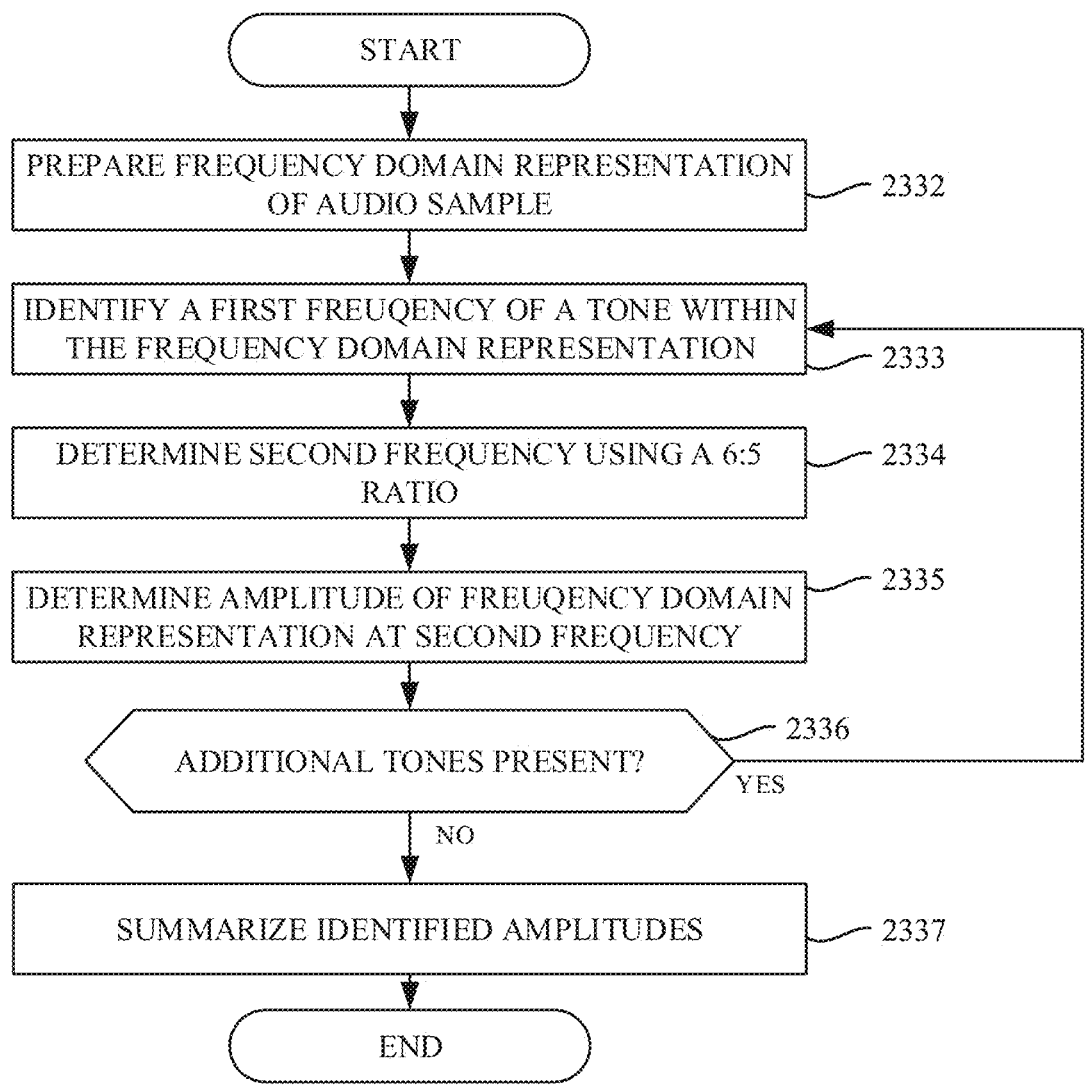

The example minor third interval identifier 330 identifies usage of minor third intervals within the sample. (block 2330). In the illustrated example, the example minor third interval identifier 330 identifies usage of the minor third intervals by determining an amplitude of tonal intervals and/or frequency intervals having a ratio of 6:5 within the audio sample. FIG. 23E is a flowchart representative of example machine readable instructions which, when executed cause the minor third interval identifier 330 to identify the presence of minor third intervals. The example program of FIG. 23E begins when the minor third interval identifier 330 prepares a frequency domain representation of a received audio sample. (block 2332). In the illustrated example, the frequency domain representation is prepared by applying a Fourier transform to the audio sample. However, the frequency domain representation may be prepared in any other fashion. The example minor third interval identifier 330 identifies a first frequency of a tone within the frequency domain representation. (block 2333). In the illustrated example, frequencies are identified when they exhibit an amplitude above a threshold amplitude.

The example minor third interval identifier 330 determines a second frequency having a ratio of six to five (6:5) with respect to the first frequency. (block 2334). For example, if the first frequency is five hundred hertz, the second frequency is identified to be six hundred hertz. The minor third interval identifier 330 determines an amplitude of the frequency domain representation at the second frequency. (block 2335). The presence of high amplitude tones at a ratio of six to five represents the presence of minor third intervals in the audio sample. The example minor third interval identifier 330 determines whether additional tones are present in the sample by, for example, determining if any other tones exhibit an amplitude above the amplitude threshold. (block 2336). If additional tones are present, control proceeds to block 2333, where the frequency of the tone is identified. If no additional tones are present, the amplitude(s) of detected minor third intervals are summarized. The summarized amplitudes are output (e.g., written to a data table, etc.) as an indicator of the presence of minor third intervals in the sample. However, the example minor third interval identifier 330 may identify the usage of minor third intervals in any other fashion.

Figure 23F:
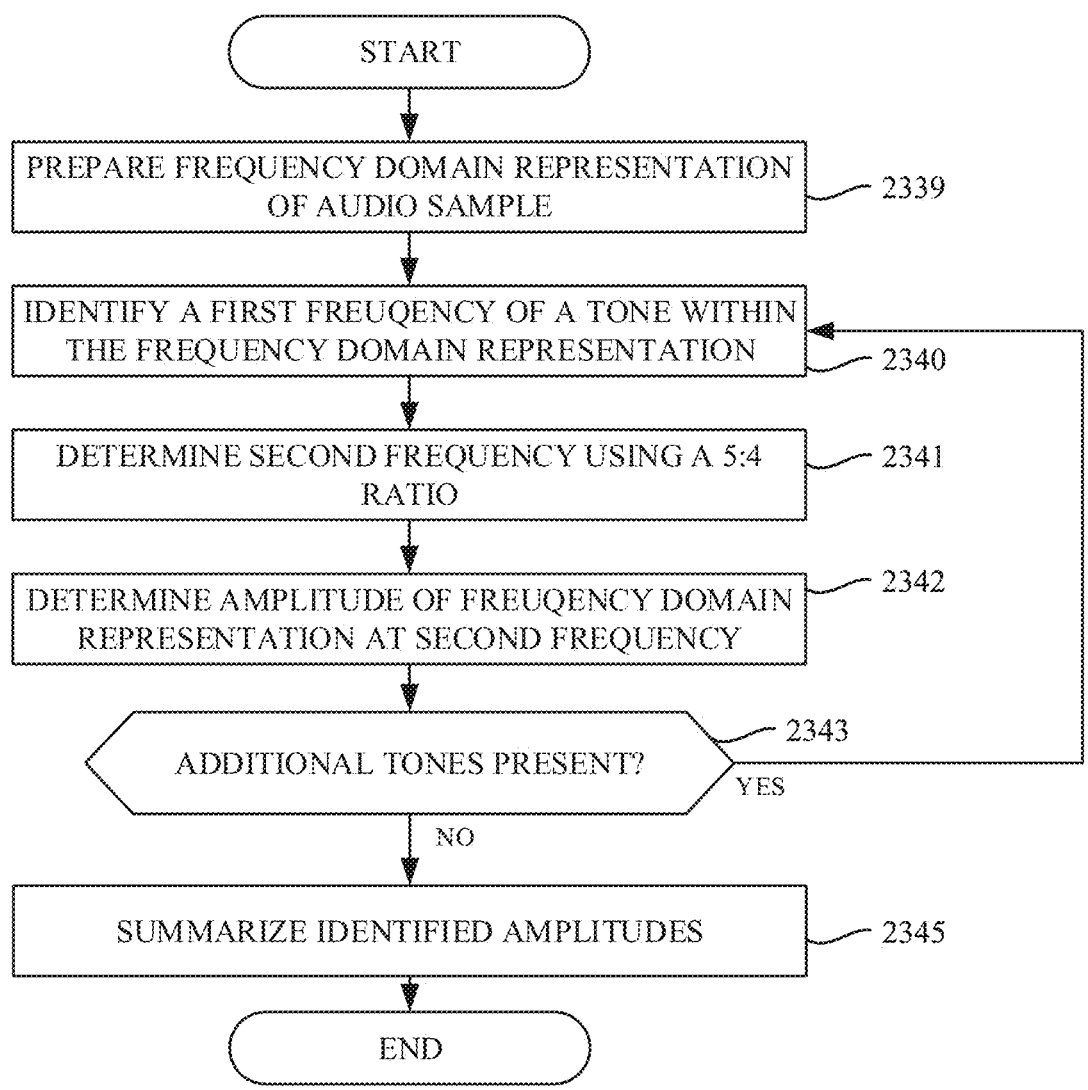

The example major third interval identifier 335 identifies usage of major third intervals within the sample. (block 2335). In the illustrated example, the example major third interval identifier 335 identifies the usage of major third intervals by determining an amplitude of tonal intervals and/or frequency intervals having a ratio of 5:4 within the sample. FIG. 23F is a flowchart representative of example machine readable instructions which, when executed cause the major third interval identifier 335 to identify the presence of major third intervals. The example program of FIG. 23F begins when the major third interval identifier 335 prepares a frequency domain representation of a received audio sample. (block 2339). In the illustrated example, the frequency domain representation is prepared by applying a Fourier transform to the audio sample. However, the frequency domain representation may be prepared in any other fashion. The example major third interval identifier 335 identifies a first frequency of a tone within the frequency domain representation. (block 2340). In the illustrated example, frequencies are identified when they exhibit an amplitude above a threshold amplitude.

The example major third interval identifier 335 determines a second frequency having a ratio of five to four (5:4) with respect to the first frequency. (block 2341). For example, if the first frequency is four hundred hertz, the second frequency is identified to be five hundred hertz. The major third interval identifier 335 determines an amplitude of the frequency domain representation at the second frequency. (block 2342). The presence of high amplitude tones at a ratio of five to four represents the presence of major third intervals in the audio sample. The example major third interval identifier 335 determines whether additional tones are present in the sample by, for example, determining if any other tones exhibit an amplitude above the amplitude threshold. (block 2343). If additional tones are present, control proceeds to block 2340, where the frequency of the tone is identified. If no additional tones are present, the amplitude(s) of detected major third intervals are summarized. The summarized amplitudes are output (e.g., written to a data table, etc.) as an indicator of the presence of major third intervals in the sample. However, the example major third interval identifier 335 may identify the usage of major third intervals in any other fashion.

Figure 23G:
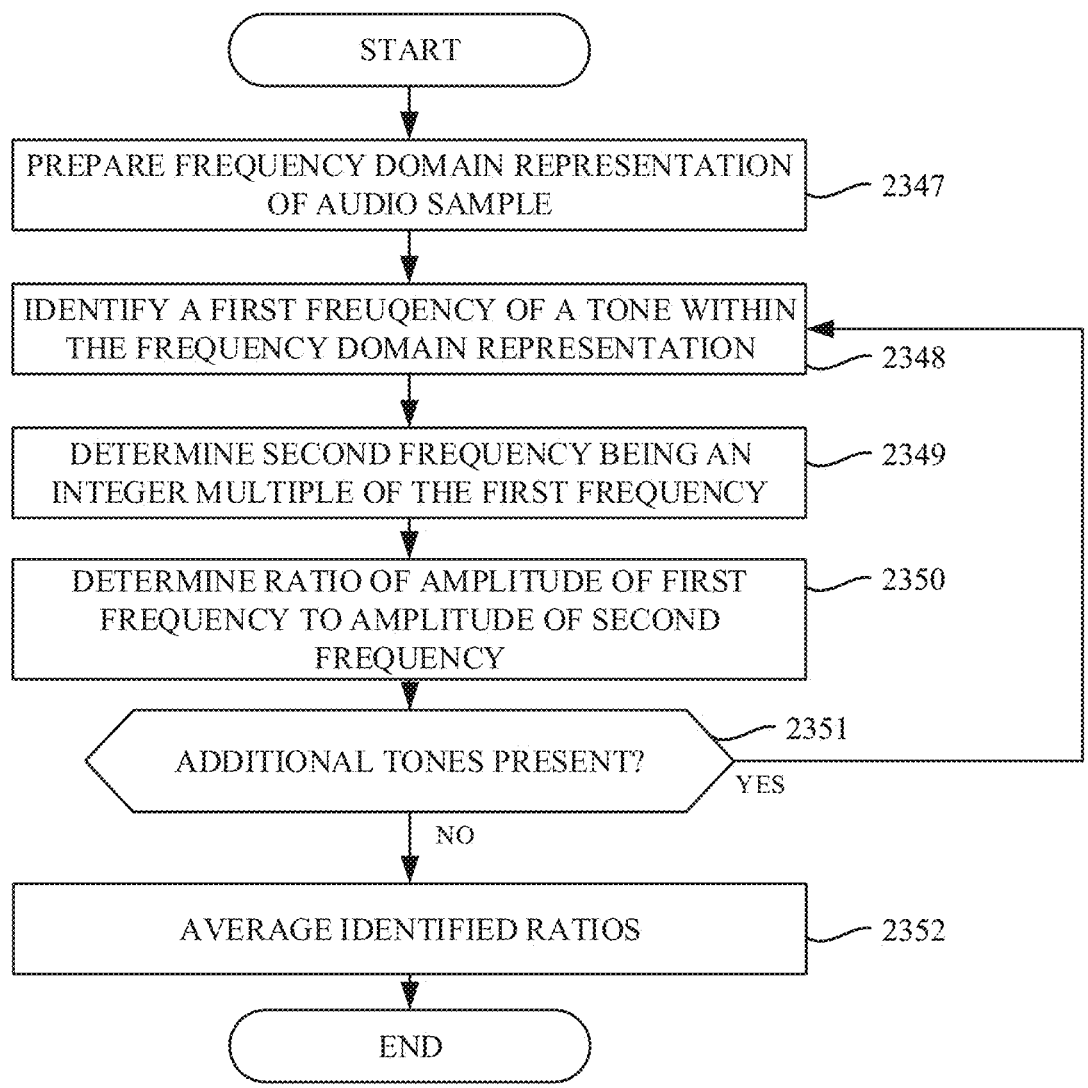

The example irregularity identifier 340 identifies irregularity within the sample. (block 2340). In the illustrated example, the irregularity identifier 340 identifies irregularity by determining an amplitude ratio between root tones and their associated harmonics. FIG. 23G is a flowchart representative of example machine readable instructions which, when executed cause the irregularity identifier 340 to identify the presence of irregularity in the audio sample. The example program of FIG. 23G begins when the irregularity identifier 340 prepares a frequency domain representation of a received audio sample. (block 2347). In the illustrated example, the frequency domain representation is prepared by applying a Fourier transform to the audio sample. However, the frequency domain representation may be prepared in any other fashion. The example irregularity identifier 340 identifies a first frequency of a tone within the frequency domain representation. (block 2348). In the illustrated example, frequencies are identified when they exhibit an amplitude above a threshold amplitude.

The example irregularity identifier 340 determines a second frequency being an integer multiple of the first frequency. (block 2349). For example, if the integer is two and the first frequency is four hundred and forty hertz, the second frequency is identified to be eight hundred and eighty hertz. In the illustrated example, the integer is two. However, any other integer value and/or combination of integer values may additionally or alternatively be used. For example, the second through fifth harmonics (e.g., integer values of two through five) may be used. The irregularity identifier 340 determines a ratio of the amplitude of the frequency domain representation at the second frequency to the amplitude of the frequency domain representation at the first frequency. (block 2350). The presence of a high ratio (e.g., close to one) represents the presence of regularity in the audio sample. The example irregularity identifier 340 determines whether additional tones are present in the sample by, for example, determining if any other tones exhibit an amplitude above the amplitude threshold. (block 2351). If additional tones are present, control proceeds to block 2348, where the frequency of the tone is identified. If no additional tones are present, the ratios of the identified tones are averaged. The averaged ratios are output (e.g., written to a data table, etc.) as an indicator of the presence of irregularity in the sample. However, the example irregularity identifier 340 may identify irregularity in any other fashion.

The example chroma identifier 345 prepares a chromagram. (block 2353). An example chromagram is shown in the illustrated example of FIG. 12. The example chromagram is created by reducing all tones within the sample to a single octave, and representing the intensity of the various tones along a time axis. An example chromagram is shown in the illustrated example of FIG. 12. As shown in the illustrated example of FIG. 12, darker shaded sections represent tones (e.g., notes) that have a higher intensity than those sections represented using lighter shading. The example chroma identifier 345 identifies the chroma of the audio sample. (block 2354). The chroma is a digital representation of the chromagram. In the illustrated example, the chroma is implemented as an array of data representing the intensity of different tones at different times. In some examples, the example chroma identifier 345 processes the chroma to, for example, filter, smooth, parse, etc. the chroma.

Figure 23H:
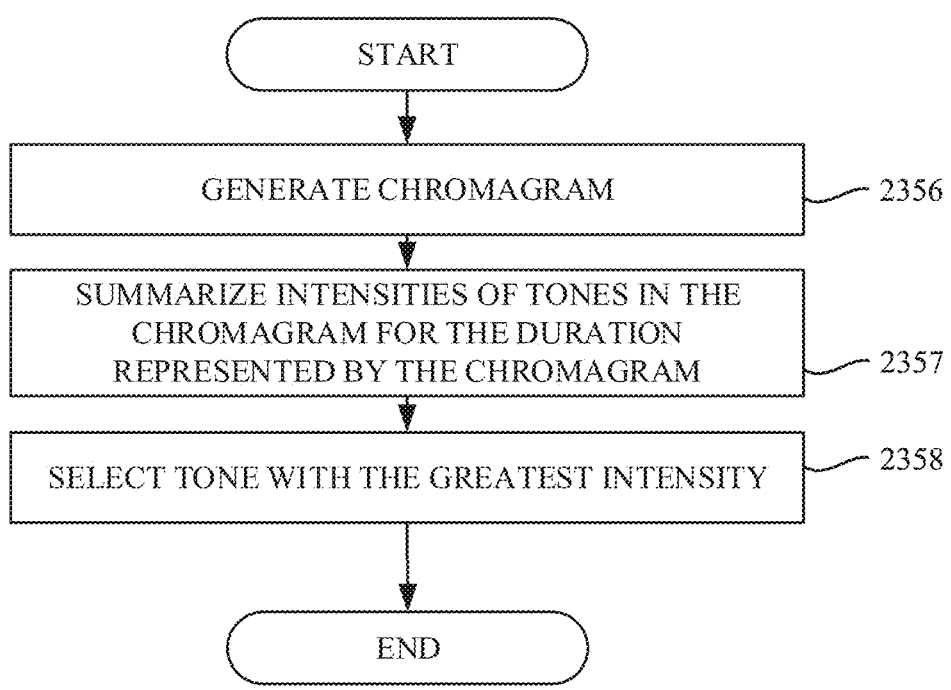

The example main pitch identifier 350 identifies a main pitch of the sample. (block 2355). In the illustrated example, the example main pitch identifier 350 identifies the main pitch by inspecting the chromagram to identify a tone having the greatest intensity throughout the audio sample. FIG. 23H is a flowchart representative of example machine readable instructions which, when executed cause the main pitch identifier 350 to identify a main pitch of the audio sample. The example program of FIG. 23H begins when the chroma identifier 335 prepares a chromagram representing intensities of various tones at various times during an audio sample. (block 2347). The example main pitch identifier 340 summarizes the intensities of the tones identified in the chromagram throughout the duration of the sample represented by the chromagram. (block 2357). In the illustrated example, the intensities are summed. However, the intensities may be processed in any other fashion such as, for example, by determining a mean of the intensities. The example main pitch identifier 340 inspects the summarized intensities and selects a tone (e.g., C, $C^{\#}$, $E^b$, etc.) having the greatest intensity throughout the sample. (block 2358). The tone having the greatest intensity is output (e.g., written to a data table, etc.) as the main pitch. However, the example main pitch identifier 350 may identify the main pitch in any other fashion.

Figure 23I:
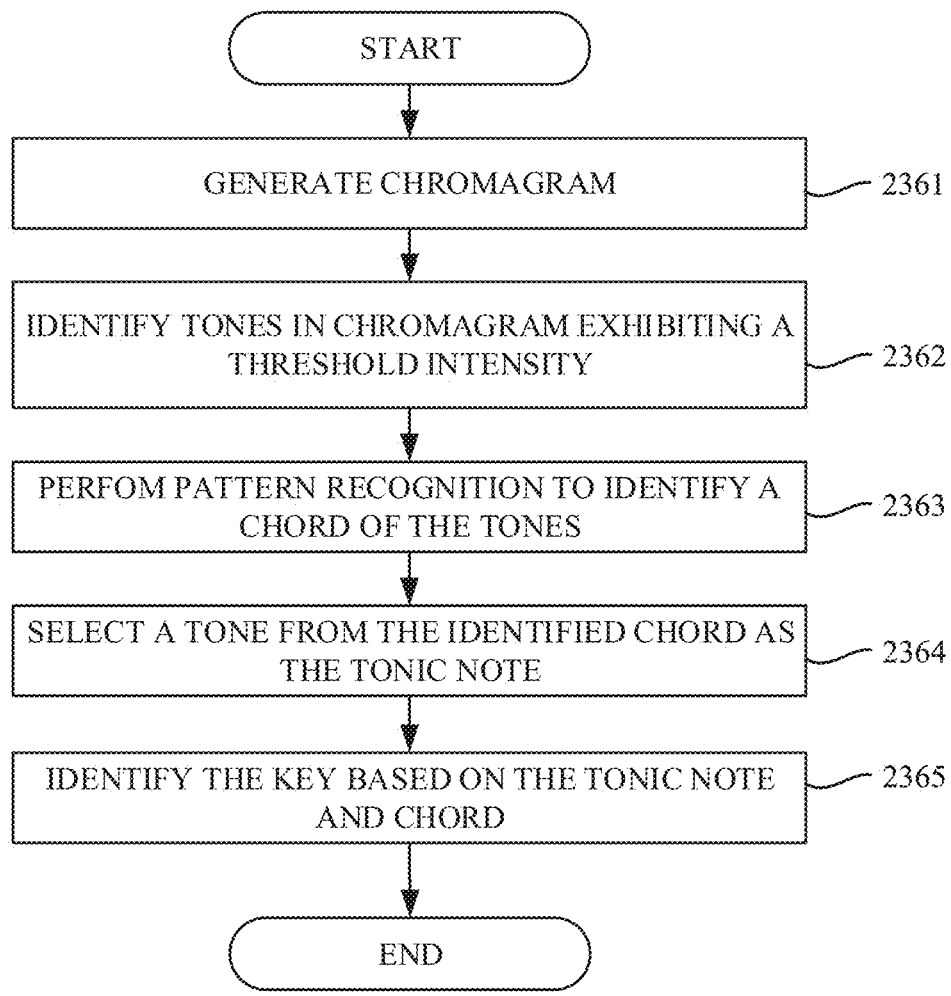

The example key identifier 355 identifies the musical key of the sample. (block 2360). In the illustrated example, the example key identifier 355 identifies the key by analyzing the chromagram to identify a tonic note and a mode of the audio sample. FIG. 23I is a flowchart representative of example machine readable instructions which, when executed cause the key identifier 355 to identify a key of the audio sample. The example program of FIG. 23I begins when the chroma identifier 335 prepares a chromagram representing intensities of various tones at various times during an audio sample. (block 2361). The example key identifier 355 identifies tones present in the chromagram that identify a threshold (e.g., minimum) intensity. (block 2362). In the illustrated example, the threshold (e.g., minimum) intensity is used to filter out tones and/or notes that may have only been used in passing in the sample (e.g., notes that do not represent the key of the sample).

The example key identifier 355 performs pattern matching on the identified tones to identify the presence of a chord. (block 2363). For example, if the tones of "C", "E", and "G" are identified, the chord may be identified as a major chord. The example key identifier selects a tone from the identified chord as the tonic note. (block 2364). For example, if the identified chord included the tones "C", "E", and "G", the key identifier selects the tone "C". In the illustrated example, the tonic note is the lowest note in the chord. However, in some examples, the tonic note may be a note other than the lowest note in the chord. Moreover, in some examples, the tonic note may not be a note that is present in the chord. The example key identifier identifies a key of the audio sample based on the tonic note and the chord. (block 2365). For example, if the tonic note is identified as "C" and the chord is identified as major, the example key identifier may identify the key as "C major". However, any other technique for identifying the musical key of the received sample may additionally or alternatively be used.

The identified features and/or characteristics of the sample are output by the feature extractor 125 to the example classification engine 130. (block 2370). In some examples, the determined factor(s) is/are written to a corresponding field in a row of a table such as, for example, the example data table 1550 of FIG. 15B.

Figure 24:
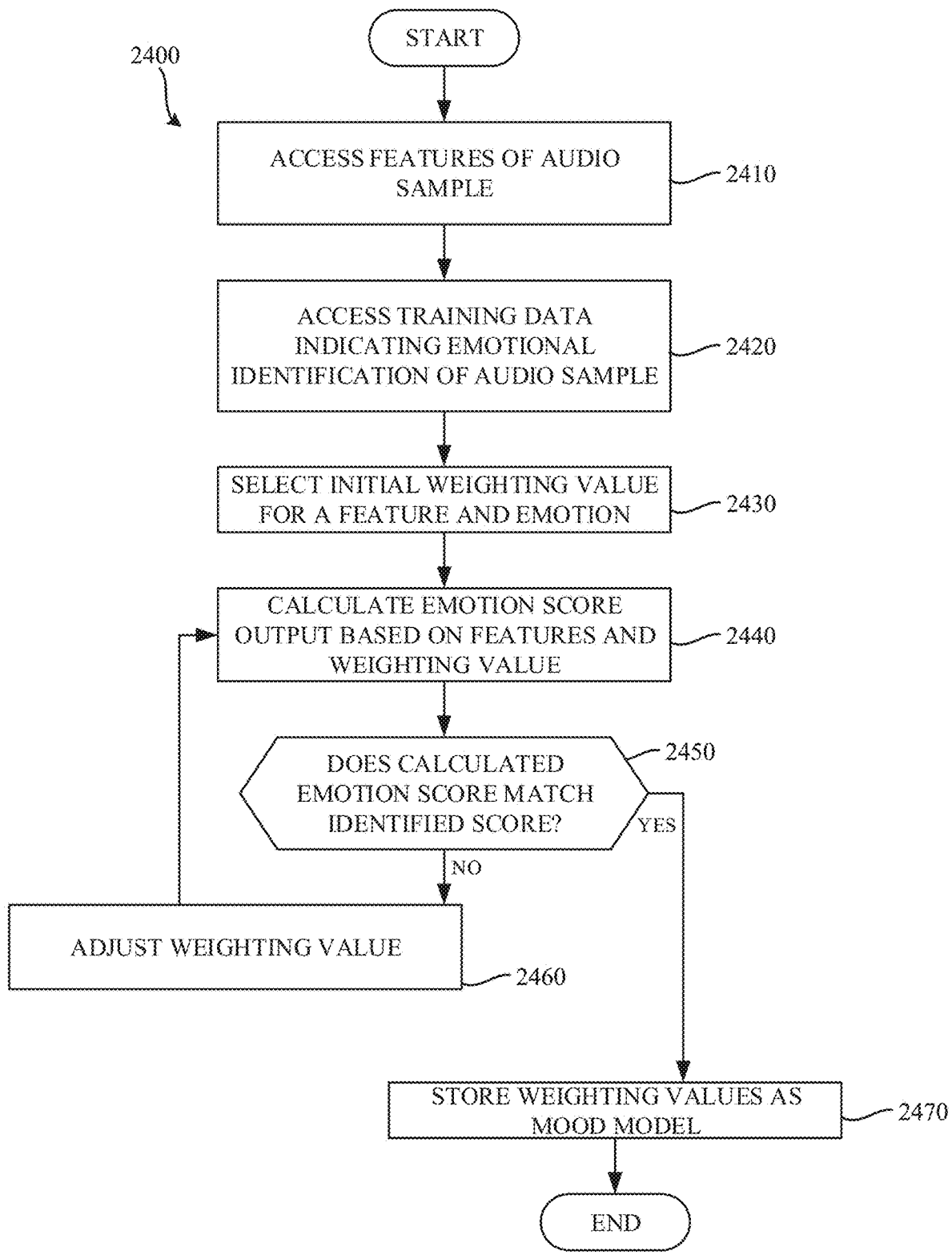
FIG. 24 is a flowchart representative of example machine readable instructions which may be executed to implement the example classification engine of FIGS. 1 and/or 13 to generate rules for classifying an emotion of audio.

FIG. 24 is a flowchart representative of example machine readable instructions 2400 which may be executed to implement the example classification engine 130 of FIGS. 1 and/or 13 to generate rules for identifying an emotion of media. Moreover, FIG. 24 represents example machine readable instructions 2400 that may be executed to implement block 2130 of FIG. 21. The example program 2400 of the illustrated example of FIG. 24 begins when the mood model creator 1320 of the example classification engine 130 accesses features of an audio sample (e.g., a pre-verbal utterance, a synthesized variant of a pre-verbal utterance, a song, etc.). (block 2410). In the illustrated example, the features of the audio sample are received from the example feature extractor 125. The example mood model creator 1320 accesses the example training data 135. (block 2420). The example training data 135, 137 indicates an emotion and, in some examples, an intensity of the emotion, that is associated with the sample on which the identified features are based. The training data can be based on pre-verbal utterances as explained above and/or other available data (e.g., the Gracenote™ database).

The example mood model creator 1320 then analyzes the identified features in connection with the indicated emotion to create a mood model. In the illustrated example, the mood model is implemented as an artificial neural network. However, the mood model may be implemented in any other fashion such as, for example, a regressive model, a Bayesian model, a table of reference emotion values (e.g., FIGS. 15A, 15B, and/or 15C), etc. In the illustrated example, the output represents an emotion score that includes information about an intensity of a particular emotion. For example, using the example weighting values of the example data table 1550 of FIG. 15B, an emotion score rated on a scale of zero to ten (0-10) may be created to indicate an intensity of an emotion. Example calculated intensity scores for different emotions are shown in the example data table 1820 of FIG. 18. In the illustrated example, the mood model is implemented by a single artificial neural network that has a number of outputs corresponding to a number of identified emotions. However, in some examples, the mood model is implemented using multiple artificial neural networks, each having a single output corresponding to an identified emotion. In some examples, the weighting data of FIG. 15B is used as weighting values for various nodes of the artificial neural network.

In the illustrated example, the mood model creator 1320 creates the mood model by selecting an initial weighting value for a feature and an emotion. (bloc 2430). For example, with reference to the example data table 1550 of FIG. 15B, the example mood model creator 1320 selects a value for each feature/emotion pair. Higher weighting values may, in some examples, indicate that a particular feature is more highly correlated with a particular emotion. For example, the flatness value identified for sadness (row 1572, column 1556 of the illustrated example of FIG. 15B) results in a weighting value of 0.9 (e.g., a high correlation). Using the selected weighting values, the example mood model creator calculates an emotion score for the media. (block 2440). In the illustrated example, the mood model creator 1320 calculates the emotion score as an intensity of an emotion on a scale of zero to ten (e.g., 0 to 10). However, any other scale may additionally or alternatively be used.

The example mood model creator 1320 determines whether the calculated emotion score matches the suggested emotion score from the training data (block 2450). In the illustrated example, a match is identified when the calculated score is within a threshold percentage (e.g., ten percent) of the emotion score from the training data. However, any other way of identifying a match may additionally or alternatively be used. If the calculated emotion intensity score does not match the emotion intensity score from the training data, the example mood model creator 1320 adjusts the weighting value (block 2460) and recalculates the emotion score. If a match is detected, the weighting values are stored as part of the mood model in the mood model database 140. (block 2470).

In some examples, additional factors are used when creating the mood model (e.g., additional non-feature based columns and weighting factors may be implemented in the example data table 1550 of FIG. 15B). For example, across different cultures, countries, and/or genders, vocalizations of emotions such as joy, humor, anger, pain, and/or surprise are well representative of these emotions. However, other emotions such as, for example, love, endearment, and/or courage are not necessarily well representative across various cultures, countries, and/or genders. In some examples, females rate vocalized emotions as being more representative of that emotion than men. For example, women rate vocalizations of joy, peace, contentment, desire, lust, and/or fear as more representative of the respective emotion than men. Moreover, while some countries and/or regions are similar in judging vocalized representations of emotion, some other countries and/or regions do not find the same vocalizations to be as representative of the same emotion. For example, persons in the United Kingdom tend to find vocalized emotions to be less representative of those emotions than in the United States, Brazil, and India. In some examples, multiple mood models may be created for use based on different demographic, ethnographic, geographic, characteristics of the user for which media is recommended.

Once the mood model is created, the example mood model creator 1320 stores the mood model in the mood model database 1370. (block 2440). Storing the mood model enables the model to be recalled at a later time for use in identifying an emotion of media being analyzed.

Figure 25:
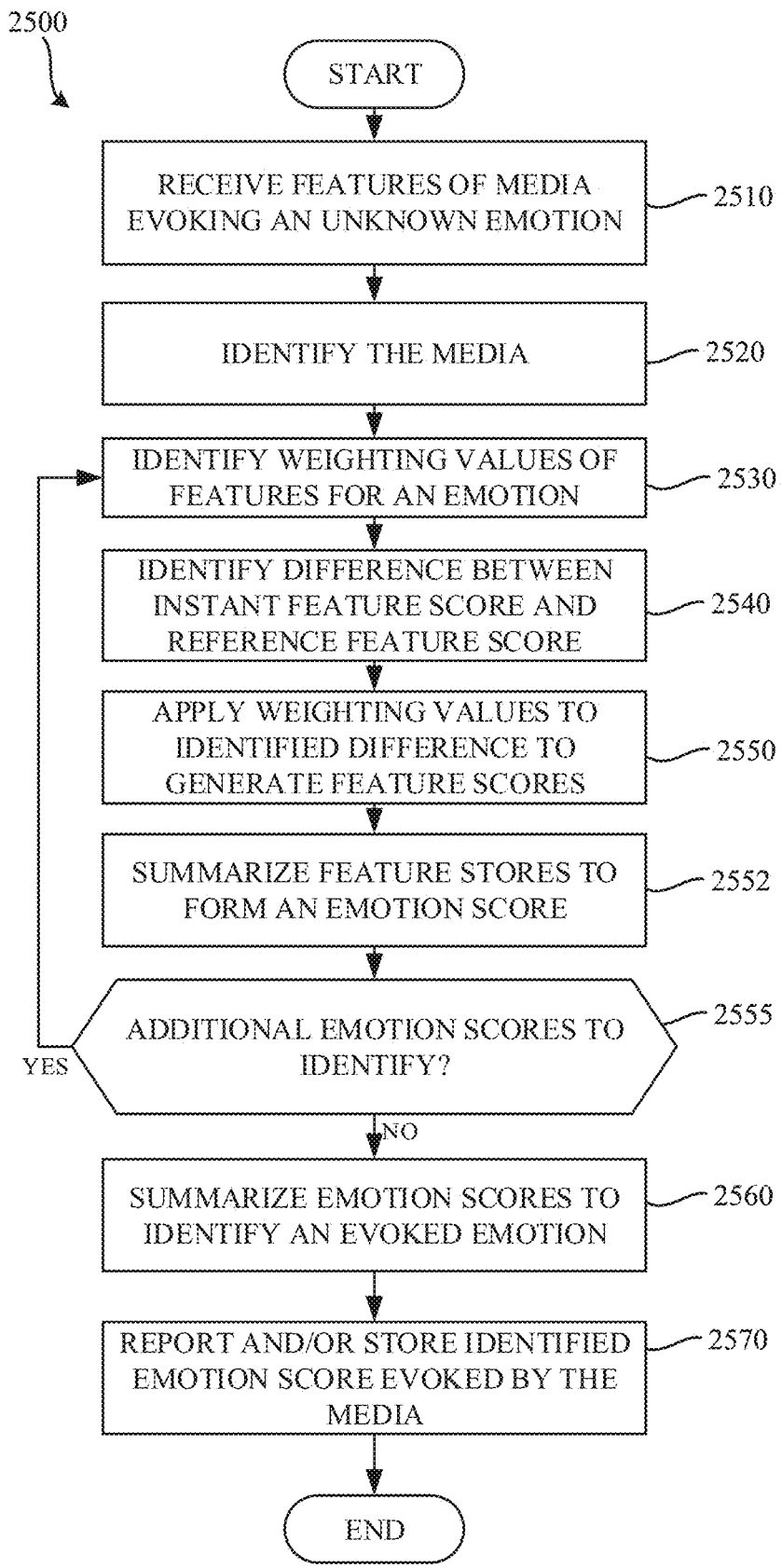
FIG. 25 is a flowchart representative of example machine readable instructions which may be executed to implement the example classification engine of FIGS. 1 and/or 13 to identify an emotion conveyed by audio.

FIG. 25 is a flowchart representative of example machine readable instructions 2500 which may be executed to implement the example classification engine of FIGS. 1 and/or 13 to identify an emotion conveyed by media. Moreover, the example machine readable instructions 2500 of the illustrated example of FIG. 25 may be used to apply the mood model generated using the example machine readable instructions 2400 of FIG. 24. The example program 2500 of the illustrated example of FIG. 25 begins when the instantaneous emotion identifier 1330 receives features of media evoking an unknown emotion. (block 2510). The example media identifier 1325 identifies the media. (block 2520). In the illustrated example, the example media identifier 1325 identifies the media by analyzing the media for the presence of a code. The code enables the media identifier 1325 to perform a lookup of the code against a reference database to identify the media. However, any other technique for identifying media may additionally or alternatively be used such as, for example, signaturing, metadata, codes, etc.

The example instantaneous emotion identifier 1330 applies the mood model created by the mood model creator 1320 to identify an emotion evoked by the media by analyzing the features received from the feature extractor 125. In the illustrated example, the mood model is applied by identifying weighting values of features for an emotion. (block 2530). The example instantaneous emotion identifier 1330 calculates a difference value between the instant feature and a reference feature value. (block 2540). In some examples, the weighting values are applied by calculating a difference between the reference value for a given feature/emotion pair and the value of the identified feature. In the illustrated example, differences are calculated by identifying an absolute value of a difference between the instant feature value and the reference feature value. In some examples, the difference is calculated by determining a similarity of the instant feature value and the reference feature value. For example, when calculating a difference between a reference chroma and an instant chroma, a difference value measuring the similarity of the two chroma is calculated. In some examples, a difference between an instant main pitch and a reference main pitch is calculated by identifying a number of semitones between the two pitches. If, for example, the reference feature and the instant feature are identical, a difference value of zero (or approximately zero (e.g., one thousandth, one hundredth, etc.) is used.

In the illustrated example, the instantaneous emotion identifier 1330 applies the weighting values to identified features of the media to create a feature score associated with the feature/emotion pair. (block 2550). In the illustrated example, the weighted feature score is calculated by dividing the respective weight values by their respective difference values. An example calculation is shown in the illustrated example of FIG. 25A. FIG. 25A represents an example calculation 2579 of an example joy score for media to be identified. The example reference value column 2580 includes reference values for joy (e.g., reference values from the example data table 1550 of FIG. 15B). The example value of instant media column 2581 represents values of features identified for the instant media. The example difference column 2582 represents a calculated difference between the reference value column 2580 and the instant value column 2581. The example weight column 2583 represents weighting values for different features (e.g., weighting values from the example data table 1550 of FIG. 15B). The example feature score column 2584 represents a weighted feature score for each feature. As described above, in the illustrated example, the weighted feature score is applied by dividing the respective weight values by their respective difference values. For example, the zero crossing column 2585 indicates a weighting value of fifteen (15), and a calculated difference of ten. Accordingly, the calculated score for the zero crossing feature is one and a half (1.50). In the illustrated example, the example instantaneous emotion identifier 1330 calculates a sum of the individual feature scores to create an emotion score. (block 2552). In the illustrated example, the calculation of the emotion score for joy results in a score of 8.75.

The example instantaneous emotion identifier 1330 determines whether there are other emotion scores to identify. (block 2555). For example, emotion scores may be identified for any number of emotions such as, for example, joy, sadness, peace, anger, courage, fear, desire, disgust, etc. If additional emotions scores are to be generated, the example instantaneous emotion identifier 1330 identifies weighting values for the next emotion (block 2530). If there are no additional emotion scores to identify (block 2555), the example mood summarizer summarizes the emotion scores to identify an evoked mood. (block 2560). The example mood summarizer 1340 identifies an emotion having a highest emotion score. For example, media to be identified may receive a joy score of 1.2, an anger score of 7.9, and a sadness score of 4.3, and the mood summarizer may identify the media as being angry. In some examples, the mood summarizer 1340 identifies a mood of the media by identifying emotions that have a score over a threshold value. For example, if a threshold value of 4.0 is used and the media to be identified receives a joy score of 1.2, an anger score of 7.9, and a sadness score of 4.3, and the mood summarizer 1340 may identify the media as primarily being angry and secondarily being sad. The instantaneous emotion identifier 1330 and/or the mood summarizer 1340 stores the instantaneous and/or summarized emotion information in the mood model database 1380 in association with the identification of the media made by the example media identifier 1325. (block 2570) In some examples, the example instantaneous emotion identifier 1330 and/or the mood summarizer 1340 reports the instantaneous and/or summarized emotion information to a requesting party such as, for example, the example mood model validator 145, the example recommendation engine 155, etc.

Figure 26:
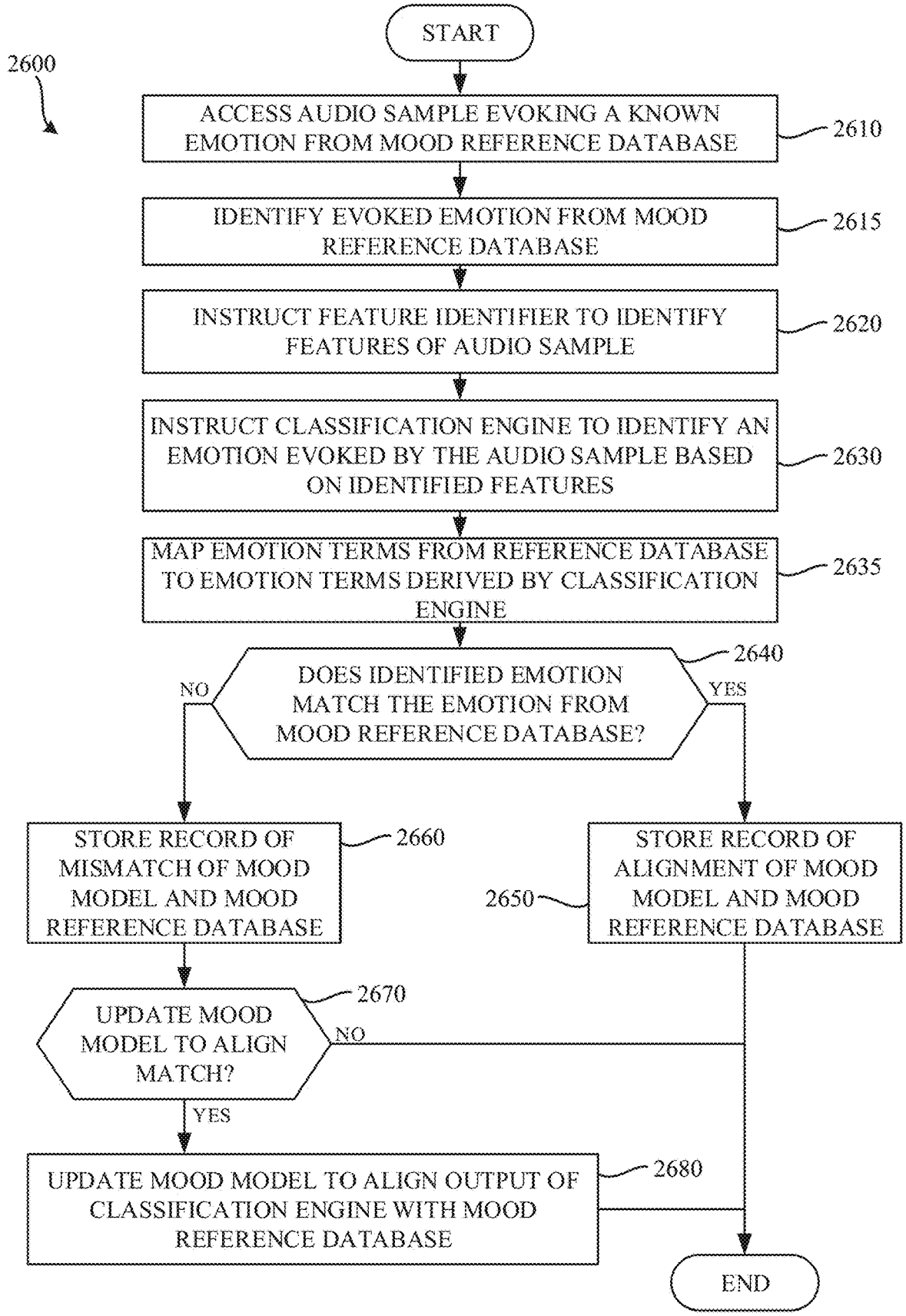
FIG. 26 is a flowchart representative of example machine readable instructions which may be executed to implement the example mood validator of FIGS. 1 and/or 16 to validate a mood model created by the example classification engine.

FIG. 26 is a flowchart representative of example machine readable instructions 2600 which may be executed to implement the example mood validator 145 of FIGS. 1 and/or 16 to validate a mood model created by the example classification engine 130. Moreover, the example machine readable instructions 2600 of the illustrated example of FIG. 26 may be used to validate the mood model as described in connection with block 2140 of FIG. 21. The example program 2600 of the illustrated example of FIG. 26 begins when the known audio accesser 1610 access an audio sample evoking a known emotion from the mood reference database 150. (block 2610). The example known mood data accesser 1620 identifies the emotion evoked by the accessed media from the mood reference database 150. (block 2615). In examples disclosed herein, the example mood reference database 150 is implemented by a Gracenote™ database that is used to identify emotions associated with known audio. However, any other database may additionally or alternatively be used. The Gracenote™ database provides emotion information that is tagged to music on a song-by-song basis.

The example mood derivation instructor 1630 transmits the audio sample to the example classification engine 130 with an associated instruction to identify an emotion, mood, and/or an intensity of an emotion/mood evoked by the audio sample. (block 2630). In response to the instruction, the example classification engine 130 identifies the emotion, mood, and/or the intensity of the emotion/mood evoked by the audio sample. The example mood derivation instructor 1630 receives an indication of the identified emotion, mood, and/or intensity of the emotion/mood (e.g., the sample evokes an emotion of sadness with an intensity of 7.2). In some examples, emotions identified by the classification engine 130 might not use the same descriptive words as emotions identified in the mood reference database 150. For example, the example classification engine 130 might identify sadness while the example mood reference database identifies sorrow. To accommodate the pre-tagged emotions, the semantic mapper 1640 creates a semantic emotion map to map the emotion descriptors used in the mood reference database 150 to the emotions identified by the classification engine 130. (block 2635). In the illustrated example, the semantic emotion map is created using standard semantic distance or closeness mapping. However any other technique for generating a semantic map may additionally or alternatively be used such as, for example, frequency of co-occurrence in regular internet space (e.g., google word distances), frequency of co-occurrence in specific body of information (e.g., word distances based on occurrence in Wikipedia), or a manually curated maps. Using the semantic emotion maps, the mood model validator 145 translates the emotion identified by the classification engine 130 to emotions identified in the mood reference database 150.

The example mood comparator 1650 compares the translated emotion and/or mood to the reference emotion and/or mood to determine if there is a match. (block 2640). If there is a match, the mood comparator 1650 stores a record of the alignment between the reference database 150 and the mood model. (block 2650). If the translated emotion and/or mood does not match the reference emotion (block 2640), the mood comparator 1650 stores a record of the mismatch between the mood model and the reference database 150. (block 2660). The example mood model updater 1660 determines whether the mood model should be updated to better align the misaligned identification. (block 2670). In examples disclosed herein, the example mood model updater 1660 determines that the mood model should be updated when, for example, a detected intensity of a given emotion and/or mood deviates from a reference intensity of the given mood and/or mood identified in the mood reference database by more than a threshold percentage (e.g., 50%). For example, if media is identified as having a sad score of 9.2 via the mood model, but is identified as having a sad score of 0.5 via the reference database, the mood model updater 1660 identifies that the mood model should be updated. In some examples, the mood model updater 1660 determines that the mood model should be updated when, for example, a threshold number of emotion and/or mood classifications do not match the mood reference database 150. For example, if fifty identifications of sadness (from the reference database) were identified as happiness (by the mood model), and the threshold number of misclassifications is forty, the example mood model updater 1660 determines that the mood model should be updated. However, any other way of identifying whether the mood model should be updated may additionally or alternatively be used.

In some examples, the mood model updater 1660 does not update the mood model when it detects a potential error in the mood reference database 150. For example, some mood reference databases classify and/or tag an entire song with emotion(s) and/or mood(s) as opposed to labeling smaller segments of the song with the emotion(s) and/or mood(s). When a song has multiple different sections (e.g., a happy section followed by a sad section followed by a joyful section), the mood reference database 150 may only identify the song as happy. While such an identification is not incorrect, it is incomplete. In such an example, the example mood model updater 1660 does not update the mood model. In some other examples, the example mood model updater 1660 identifies that the mood model should be updated. (block 2670). The example mood model updater 1660 then updates the mood model stored in the mood model database 140 to align the output of the classification engine 130 with the mood reference database 150. In the illustrated example, the example mood model updater 1660 updates the mood model by modifying the weighting values of the mood model. For example, the mood model updater 1660 may modify the zero crossing value (e.g., column 1562 of FIG. 15C) for joy (e.g., row 1552 of FIG. 15C) to indicate a different correlation between a feature of the media and a particular emotion. In some examples, the mood model updater 1660 uses, for example, reinforcement learning to train the artificial neural network of the mood model. However, in some examples, the mood model updater 1660 updates the training data 135 such that the emotional identification of the song from the reference database is accounted for when a new and/or subsequent mood model is created by the example mood model creator 1320. In some examples, after adding the emotional identification of the song and the song to the training data 135, the example mood model updater 1660 requests the classification engine 130 to update the mood model.

Figure 27:
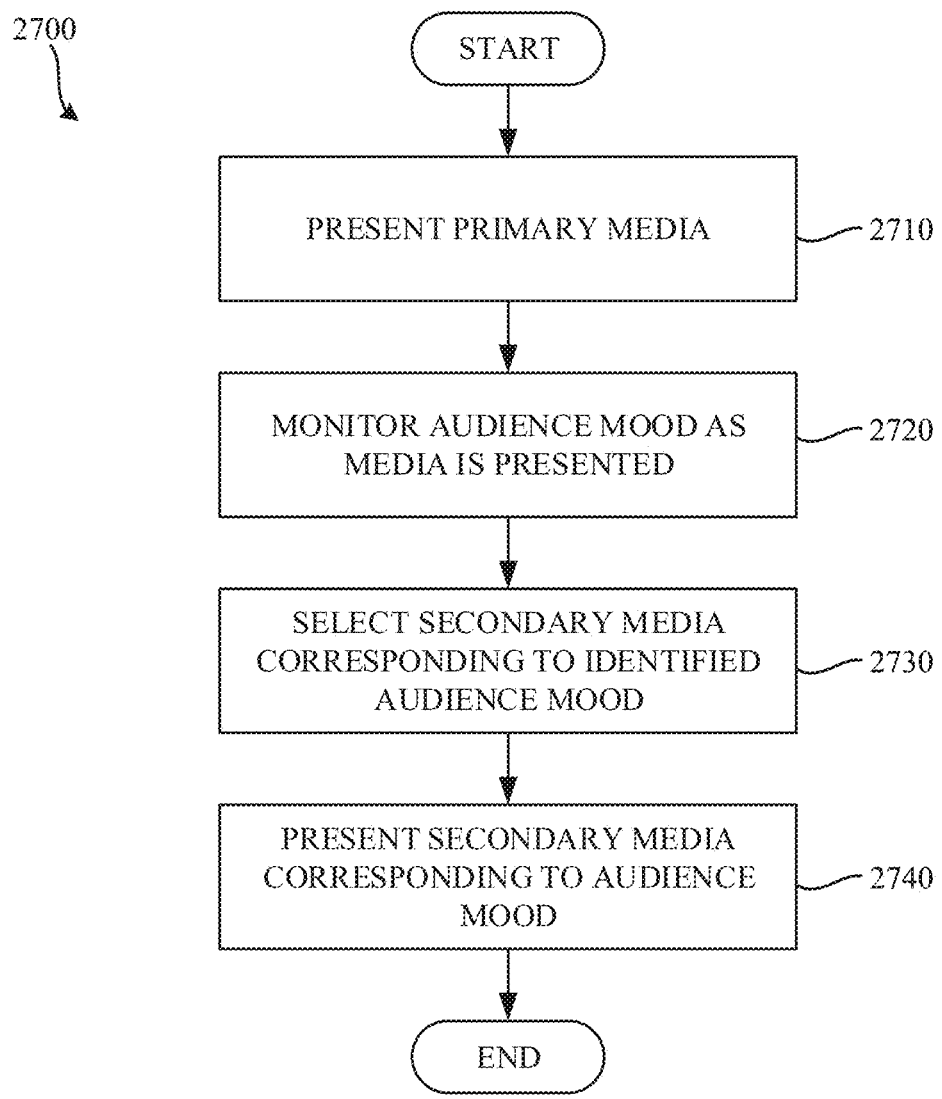
FIG. 27 is a flowchart representative of example machine readable instructions which may be executed to implement the example recommendation engine of FIGS. 1 and/or 17 to select an advertisement corresponding to an identified mood of an audience.

FIG. 27 is a flowchart representative of example machine readable instructions 2700 which may be executed to implement the example recommendation engine 155 of FIGS. 1 and/or 17 to select media (e.g., an advertisement) corresponding to an identified mood of an audience. Online advertising is commonly featured in connection with online searches of media. For example, advertisements can be displayed along with search results, such as along a margin of a search results page. Once a search result is selected and a page is displayed to view the selected content, advertisements can also be displayed next to the content. In addition, advertisements can be played before, during, or after playing the selected content. For example, when a video is played, an advertisement may play before the video is presented. In other examples, particularly when the video is of an extended length (e.g., longer than ten minutes), advertisements may appear periodically during the video as commercial breaks.

The human brain devotes substantial resources to process emotions. The human brain places high importance on what it perceives to be particularly relevant data such as, for example, a personalized product, a personalized message, etc. Selecting an appropriate advertisement based on an emotion of a user can increase the effectiveness of the advertisement and the user's opinion of the associated brand. Accordingly, rather than select advertisements based on a product or brand, advertisements may be selected based on an emotion exhibited by a user. Furthermore, advertisements may be customized using elements such as music or musical sequences to further refine the emotion to that of the user.

The example program 2700 of the illustrated example of FIG. 27 begins when the media presenter 165 of the media device 160 presents primary media. (block 2710). The example user mood detector 1730 of the example recommendation 155 monitors a mood of an audience as the media is presented. (block 2720). In the illustrated example, the user mood detector 1730 monitors for facial expressions and facial action coding. The example user mood detector 1730 monitors the user via, for example a camera-based device such as a camera of the media device 160. However, any other method of identifying an emotion and/or mood of a user may additionally or alternatively be used such as, for example, heart rate monitoring, blood pressure monitoring, neurological based monitoring, etc. For example, a user exhibiting a higher than normal blood pressure and/or a higher than normal heart rate may be identified as being tense and/or exhibiting fear.

The example media selector 1750 selects second media (e.g., an advertisement) based on the identified user emotion and/or mood. (block 2730). As described in connection with FIG. 18, the example media selector 1750 identifies media having a smallest emotional distance between the current emotion(s) and/or mood(s) of the primary media and a desired emotion(s) emotion(s) and/or mood(s) (e.g., the emotion and/or mood exhibited by the user). In the context of advertisement selection, in some examples, the emotional distance is paired with a cost index to enable advertisers to identify an advertisement that is both well suited for matching an emotion of a user and whose cost of presenting the advertisement to the user meets a budget or cost threshold. For example, advertisements that are expensive to present to a user because of, for example, royalties, licenses, etc. may be presented in situations when the emotion(s) emotion(s) and/or mood(s) evoked by the advertisement are highly correlated with the emotion(s) emotion(s) and/or mood(s) of the user (e.g., the advertisement has a high likelihood of leaving a positive impression on the user). As such, advertisements that are highly correlated with the emotion(s) emotion(s) and/or mood(s) of the user may demand a higher price because they provide a better value and/or better emotional impact on the user per advertising dollar spent. Once the secondary media (e.g., the advertisement) is selected for presentation, the example media presenter 165 of the example media device 160 presents the secondary media to the user. (block 2740).

Figure 28:
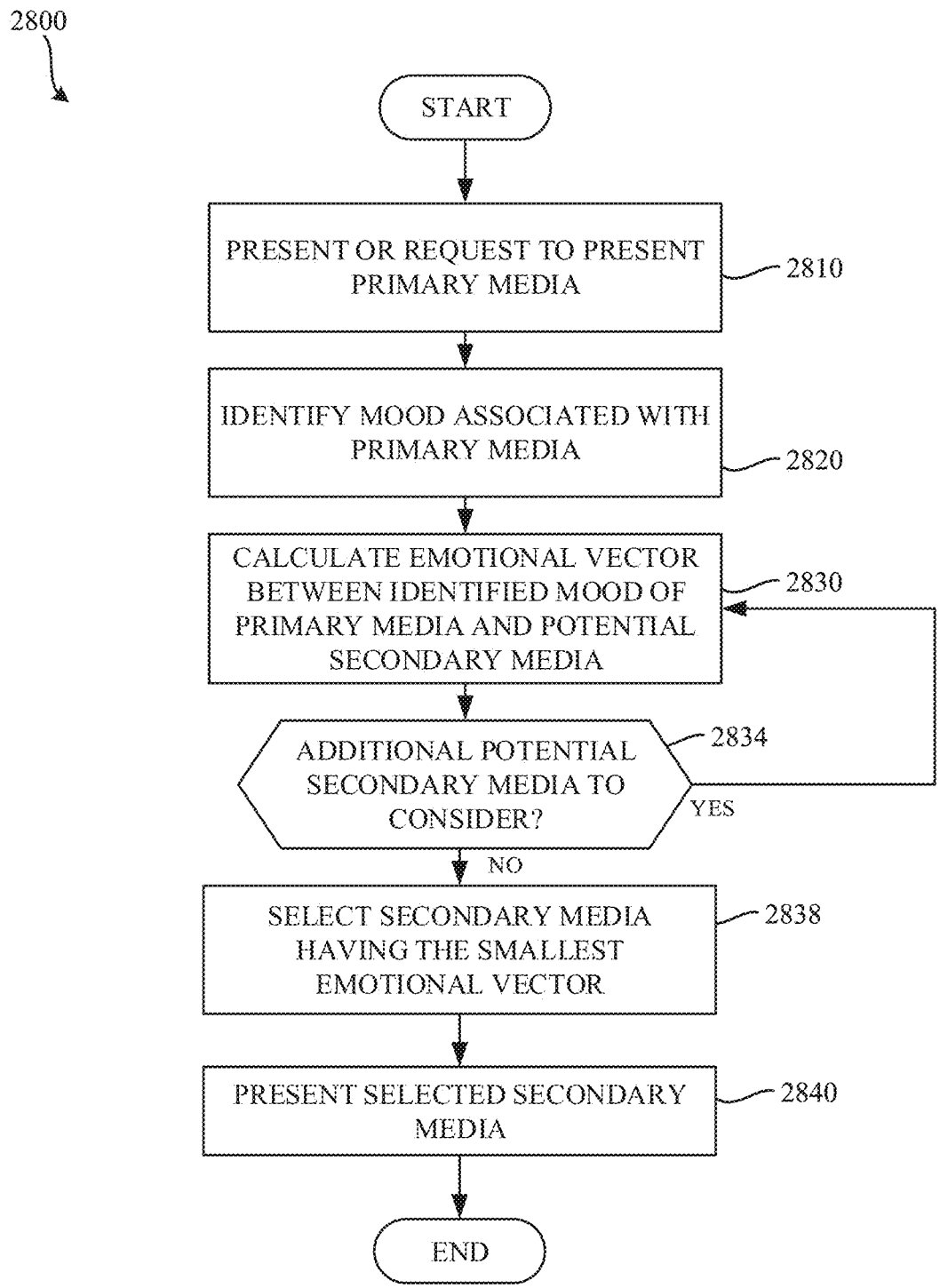
FIG. 28 is a flowchart representative of example machine readable instructions which may be executed to implement the example recommendation engine of FIGS. 1 and/or 17 to select an advertisement corresponding to an identified mood of media.

FIG. 28 is a flowchart representative of example machine readable instructions 2800 which may be executed to implement the example recommendation engine 155 of FIGS. 1 and/or 17 to select an advertisement corresponding to an identified mood of media. In contrast to the illustrated example of FIG. 27, the illustrated example of FIG. 28 bases the advertisement selection on an identified mood of primary media currently presented or selected for presentation.

The example program 2800 of the illustrated example of FIG. 28 begins with the media presenter 165 of the example media device 160 presenting or requesting to present primary media. (block 2810). In examples disclosed herein, the primary media requested by a user can include music, videos, documentaries, how-to videos, news reports, movies, television shows, or any other media. In some examples, the primary media may include and/or be associated with metadata information. In some examples, secondary media (e.g., an advertisement, a television show, a video, etc.) to be presented with the primary media is automatically selected such that the mood of the selected secondary media (e.g., the advertisement) matches a mood of the primary media.

In the illustrated example, the media selector 1750 transmits a request including the primary media and/or segments of the primary media to the feature extractor 125 to initiate identification of an emotion and/or mood associated with the primary media. (block 2820). The example media selector receives emotion and/or mood data from the classification engine 130 in response to the request. In some examples, the request may include metadata (e.g., a title, a track number, an album name, an artist name, etc.) associated with the primary media such that, in the event that the classification engine 155 has already identified an emotion and/or mood evoked by the primary media and/or the mood of the primary media, the identified emotion and/or mood information may be supplied to the media selector 1750 without parsing the primary media into features and/or analyzing the feature set. In some other examples, social media information may be collected and/or analyzed to identify the emotion(s) and/or mood(s) of the primary media. In some examples, a determined emotion and/or mood of the primary media can be associated with various categories such as surprise/novelty, fear/anger, nostalgia, edgy/sensual, comedic/funny, etc. In some examples, other types of emotions and/or moods can include serious (e.g., a news report), solemn (e.g., a memorial or an in memoriam), sad, happy, excited, romantic, hopeful, inspired, etc. In some examples, a news report is categorized as serious, a memorial is categorized as solemn, and an awards show is categorized as excited, romantic, hopeful, and/or inspired.

As described in connection with FIG. 18, the example media selector 1750 calculates an emotional distance using emotional scores of the primary media and potential secondary media. (block 2830). As described in connection with FIG. 18, the example emotional distance is calculated by determining a sum of an absolute value of differences for each emotion. For example, an example happy score for media A 1830 of FIG. 18 is 7.2 and deviates from the desired happy score of 8 by 0.8. The example sad score for media A 1830 of FIG. 18 deviates from the desired sad score by 0.8. The example joyful score for media A 1830 of FIG. 18 deviates from the desired joyful score by 1.2. A sum of these differences is represented as the emotion distance (column 1828), and results in an emotion distance of 2.8 for media A 1830. The example media selector 1750 determines whether there are other potential secondary media to be considered. (block 2834). If additional media is to be considered, the example media selector calculates an emotional distance between the identified mood of the primary media and the potential secondary media. (block 2830). For example, with reference to the example of FIG. 18, the example media selector 1750 may identify the emotion distance associated with media B 1832 of FIG. 18 to be 6.5. The example media selector 1750 may identify the emotion distance associated with media C 1834 of FIG. 18 to be 12.8. If no additional media is to be considered (block 2834), the example media selector 1750 selects secondary media (e.g., an advertisement) based on the calculated emotion distances. (block 2838). In the illustrated example, the example media selector 1750 selects the secondary media having a smallest emotional distance (e.g., the smallest emotional difference) between the emotions of the primary media and the emotions of the secondary media. Selecting appropriate media is important because, for example if a happy or romantic advertisement is chosen when a media presented adjacent the selected advertisement is sad, the selected advertisement might seem inappropriate or even offensive to the user. In the context of advertisements, in some examples, the example media selector 1750 may select advertisements for presentation based on specified keywords and/or price (e.g., a cost of presenting the advertisement, a cost of the product identified in the advertisement, etc.). For example, some online video streaming services offer advertisement placements to clients that provide their own advertisements, keyword selections, and price limits. The keywords may, in some examples, be used to select the advertisement for presentation to an audience that is most likely to be interested in the goods or services provided in the advertisement. Once the secondary media is selected for presentation, the example media presenter 165 of the example media device 160 presents the secondary media to the user. (block 2840). While, in the illustrated example, the secondary media is presented after the primary media, the secondary media may be shown at any other time such as, for example, before the primary media, during the primary media, etc.

Figure 29:
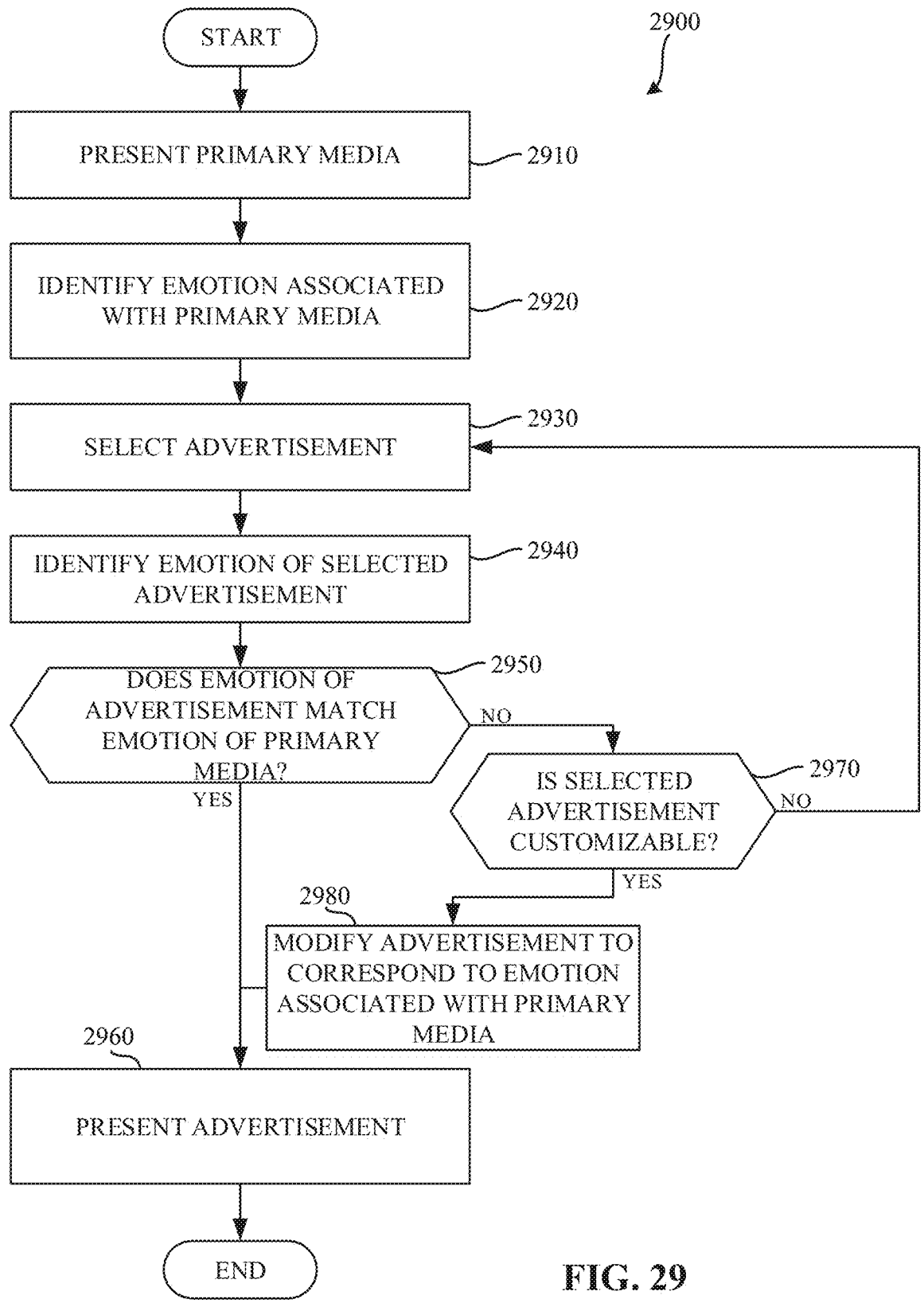
FIG. 29 is a flowchart representative of example machine readable instructions which may be executed to implement the example recommendation engine of FIGS. 1 and/or 17 to modify a mood of an advertisement to correspond to a mood of presented media.

FIG. 29 is a flowchart representative of example machine readable instructions 2900 which may be executed to implement the example recommendation engine 155 of FIGS. 1 and/or 17 to modify an emotion and/or a mood of an advertisement to correspond to an emotion and/or a mood of presented media. In some examples, media (e.g., an advertisement) may be customized to more closely match a desired emotion and/or mood. For example, matching a mood of music in an advertisement to the mood of content played before and/or after the advertisement can improve the user's experience with the advertisement and lead to a more favorable impression of the product, service, or business/entity associated with the advertisement. For example, if a user requests a sad video, an advertisement played before and/or after the sad video can be modified to use music that is also sad. Presenting customized media (e.g., a customized advertisement) results in presentations that are less likely to offend and/or disrupt the user and/or the media exposure experience. Mood matched advertisements will also appear to be less abrupt next to the surrounding content. As a result, users are more likely to be receptive to the customized advertisement.

The example program 2900 of the illustrated example of FIG. 29 begins at block 2910 when the media presenter 165 presents and/or requests primary media. (block 2910). The example media selector 1750 interacts with the feature extractor 125 and/or the classification engine 130 to identify an emotion (e.g., an instantaneous emotion) of the primary media. (block 2920). In the illustrated example, the primary media is presented before and/or during identification of an emotion evoked by the media. However, in some examples, the primary media may instead be selected for presentation at a later time (e.g., added to a playlist) and/or may be selected based on the mood of the media.

Based on the identified emotion and/or mood, the media selector 1750 selects an advertisement. (block 2930). In the illustrated example, the advertisement is selected based on its mood, such that the mood of the advertisement matches the mood of the primary media. For example, if the primary media is a television show featuring vampires, and is categorized as fantasy or supernatural drama, the media selector 1750 may select an advertisement that is categorized as dramatic, dark, and/or moody. However, in some examples, the advertisement is selected based on its subject matter, such that the subject matter of the advertisement matches the subject matter and/or emotion evoked by the primary media. For example, if the media selection is a television show featuring vampires and is categorized as fantasy or supernatural drama, the media selector 1750 may select an advertisement that includes vampires and/or other supernatural characters.

The example media selector identifies an emotion and/or mood evoked by the selected advertisement. (block 2940). In the illustrated example, the media selector 1750 interacts with the feature extractor 125 and/or the classification engine 130 to identify an emotion and/or mood of the selected advertisement. In other examples, the advertisement may be pre-labeled with an emotion and/or mood (e.g., by processing it with the mood model at an earlier time, based on metadata, etc.) If the example media selector 1750 determines that the emotion and/or mood of the selected advertisement matches the emotion and/or mood of the primary media (block 2950), the media selector 1750 directs the media presenter 165 to present the selected advertisement. (block 2960). If the example media selector 1750 determines that the emotion and/or mood of the selected advertisement does not match the emotion and/or mood of the primary media (block 2950), the media customizer 1760 determines whether the selected advertisement is customizable. (block 2970). If the selected advertisement is not customizable (block 2970), an alternative advertisement can be selected (block 2930) and a determination can be made about whether the alternative advertisement evokes an emotion and/or mood matching an emotion of the primary media (block 2950). This process continues until an advertisement is selected that evokes an emotion and/or mood matching the emotion and/or mood of the primary media.

If customization of the selected advertisement is available (block 2970), a customized advertisement can be created with music that evokes an emotion and/or mood matching the emotion and/or mood evoked by the primary media. In the illustrated example, music accompanying an advertisement is changed to match the emotion and/or mood of the primary media. In some examples, aspects of the advertisement can be selected to stay constant across multiple versions, and other aspects of the advertisement can be selected to be variable (e.g., interchangeable with other options). For parts of the advertisement that are anchored across various versions, neuro-compression can be applied in some examples such that important aspects of the advertisement are retained in the compressed version. In some examples, neuro-iconic signatures can be embedded in the anchored parts of the advertisement. In some examples, the anchored parts of the advertisement may be characters, words, people, etc. in the foreground of the advertisement. In contrast, variable parts of the advertisement may be the background, lighting, music, colors present in the advertisement, etc. In the illustrated example, the advertisement is customized to evoke an emotion and/or mood corresponding to an emotion and/or mood of the primary media. For example, musical tracks accompanying the advertisement can be selected to compliment the emotion(s) and/or mood(s) associated with the primary media. In some examples, a portion of a musical track is selected because, for example the selected portion corresponds to a particular emotion and/or mood (whereas the musical track as a whole may correspond to a different emotion and/or mood). In some examples, other properties of the advertisement may be modified. For example, different hues and/or tones can be selected to compliment the emotions and/or mood of the primary media. If more subtle variations are desired, the backgrounds can remain the same or similar across various versions of an advertisement. For example, a room with a window may appear in multiple variations of the advertisement, but lighting as seen through the window might be altered across those multiple versions.

Once the advertisement has been customized, the example media selector 1750 directs the media presenter 165 to present the customized advertisement (block 2960).

Figure 30:
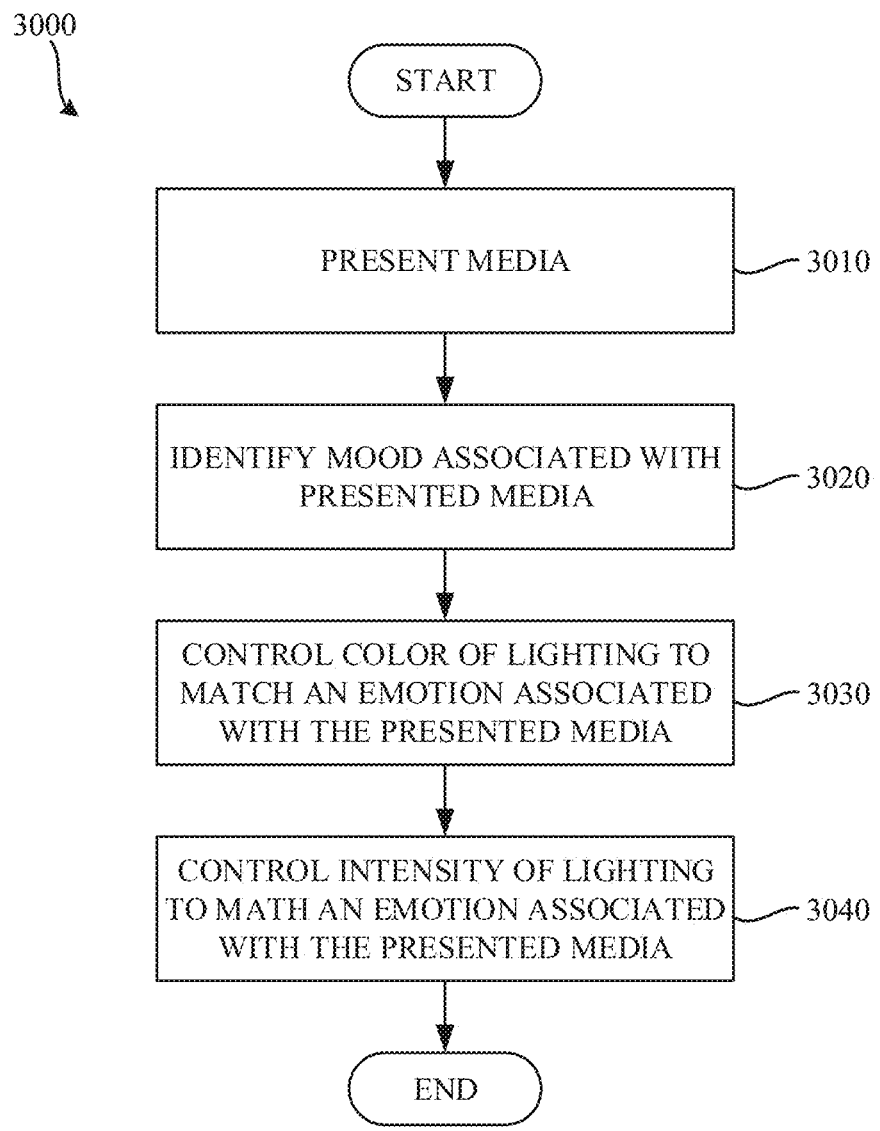
FIG. 30 is a flowchart representative of example machine readable instructions which may be executed to implement the example recommendation engine of FIGS. 1 and/or 17 to control an environment in response to identification of a mood of presented media.

FIG. 30 is a flowchart representative of example machine readable instructions 3000 which may be executed to implement the example recommendation engine 155 of FIGS. 1 and/or 17 to control an environment in response to identification of a mood of presented media. In some examples, based on the emotion and/or mood evoked by media presented to a user, lighting background, and/or graphics associated with social media can be presented and/or modified. The example program 3000 of the illustrated example of FIG. 30 begins at block 3010 when the media presenter 165 presents media. (block 3010). In the illustrated example, the media is presented before and/or during identification of an emotion and/or mood of the media. However, in some examples, the media is presented at a later time after it has been processed for emotional classification. In the illustrated example, the example media selector 1750 passes the media to the feature extractor 125 which extracts features for use by the classification engine 130 in identifying an emotion and/or mood of the presented media. (block 3020).

Based on the identified emotion and/or mood, the environment controller 1770 controls a color of lighting (e.g., green, blue, red, etc.) to match the identified emotion. (block 3030). The environment controller 1770 controls an intensity of the lighting (e.g., lights in a house are dimmed as media is presented) to match the identified emotion and/or mood. (block 3040). For example, the intensity of the lighting may be increased when happy media is presented versus being dimmed when sad media is presented. In some examples, the color and/or intensity of the lighting are modified based on other musical characteristics such as, for example, rhythm, amplitude, pitch, etc. In the illustrated example, the lighting is controlled by interfacing with a home automation system. However, any other way of controlling lighting may additionally or alternatively be used. Moreover, lighting may be controlled in many different contexts such as, for example, room lighting in a home theatre, dance music lighting, disk-jockey lighting, stage lighting at a concert, etc.

Figure 31:
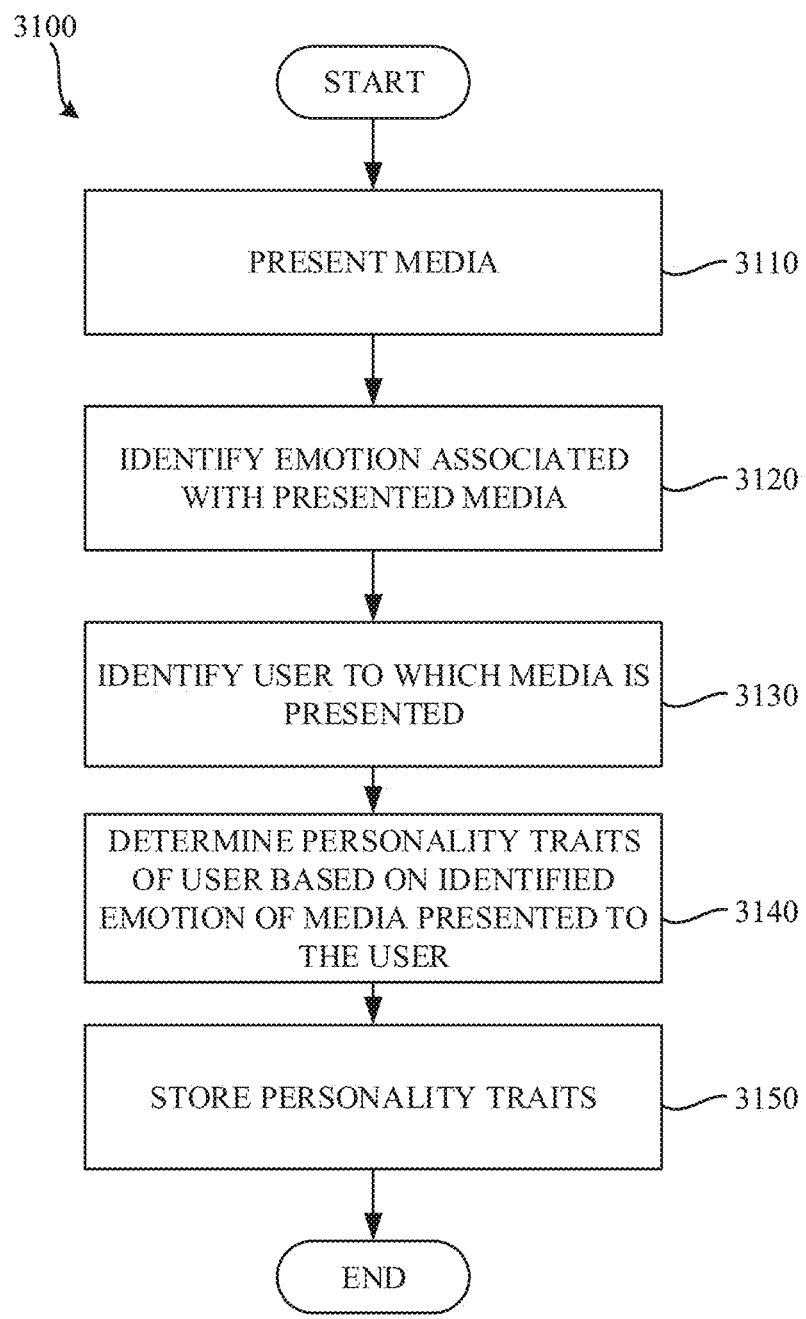
FIG. 31 is a flowchart representative of example machine readable instructions which may be executed to implement the example recommendation engine of FIGS. 1 and/or 17 to determine personality traits of a user based on a mood of media presented to the user.

FIG. 31 is a flowchart representative of example machine readable instructions 3100 which may be executed to implement the example recommendation engine of FIGS. 1 and/or 17 to determine a personality trait of a user based on an emotion and/or a mood of media presented to the user. In some examples, personality profiles are generated based on mood-based music features included in a user playlist and/or media access history. Characteristics of individuals can be determined and stored in a user profile. The user profile may be useful to, for example, enable recommendation of media to the user. In some examples, the user profile functions as a backup to other recommendation approaches. For example, recommendations based on the profile may be used in examples where the mood of the user is not identifiable, the mood of the media presented to the user is not identifiable, etc.

The example program 3100 of the illustrated example of FIG. 31 begins at block 3110 when the media presenter 165 presents media. (block 3110). In the illustrated example, the media is presented before and/or during identification of an emotion and/or mood of the media. However, in some examples, the media is presented at a later time after it has been processed for emotional classification. In the illustrated example, the example media selector 1750 passes the media to the feature extractor 125 which extracts features for use by the classification engine 130 in identifying an emotion and/or mood of the presented media. (block 3120). The example media selector 1750 identifies the user to which the media is and/or was presented. (block 3130). In the illustrated example, the user is identified by determining a username of a user that is logged into the media device 160. However, any other way of identifying the user may additionally or alternatively be used such as, for example, facial recognition via a camera of the media device 160, etc. The media selector 1750 determines personality traits of the identified user based on the identified emotion and/or mood of the presented media over time. (block 3140). For example, the user may be identified as having a personality trait of being a happy person when the user frequently listens to media evoking an emotion of happy. The media selector 1750 then stores the determined personality traits. (block 3150). In the illustrated example, the personality traits are used to facilitate recommendation of media to the user. However, in some examples, personality traits and/or media exposure information associated with other users may be used to facilitate recommendation of media to the user. For example, media may be recommended when it is labeled as "liked" (e.g., via a social media outlet such as, for example, Facebook, twitter, etc.) by others that exhibit similar personality traits.

Figure 32:
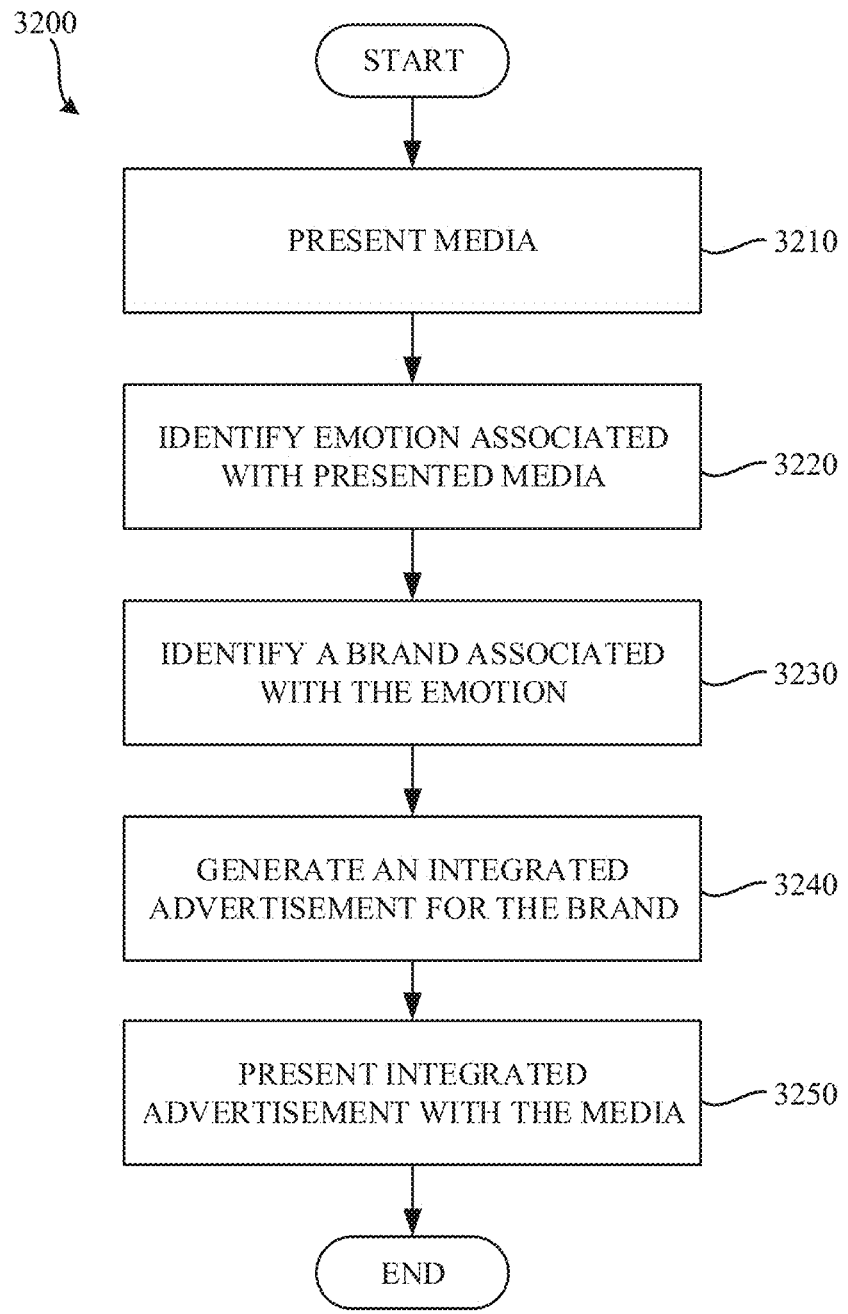
FIG. 32 is a flowchart representative of example machine readable instructions which may be executed to implement the example recommendation engine of FIGS. 1 and/or 17 to generate and present an integrated advertisement.

FIG. 32 is a flowchart representative of example machine readable instructions 3200 which may be executed to implement the example recommendation engine 155 of FIGS. 1 and/or 17 to generate and present an integrated advertisement. As used herein, an integrated advertisement is an advertisement that is presented immediately before or after a piece of media. Integrated advertisements can be more appealing to audience members because they are less disruptive than traditional advertisements and because they provide interesting information about the audio that the audience member is accessing. In some examples, an integrated advertisement provides useful and/or interesting information associated with the presented media, which can enhance an audience member's relationship with the brand.

Advertisement breaks in media can be disruptive to a media presentation experience. For example, advertisements in the free version of a streaming media application (e.g., Pandora, Spotify, etc.) may break up a flow of the music presented and can feel jarring or disruptive to a listener. Accordingly, in some examples disclosed herein, advertising breaks of this kind are avoided. Instead, integrated advertisements are presented that include both information about the presented media and information about a brand that may be sponsoring the advertisement. For example, when a song is played, a tagline of "a gift for you from COCA COLA®" may be intermingled with information about the song such as the name of the label and name of song. In some examples, a message can be played such as "next playing is 'Happy' by Pharrell Williams from 2014, brought to you by COCA COLA®." In some examples, a branded statement pertaining to an advertisement can be added to this information. In some examples, the integrated advertisement is presented after the media (e.g., "that was 'Happy' by Pharrell Williams from 2014, brought to you by COCA COLA®"). In some examples, the integrated advertisement is played at various points in the media. For example, the integrated advertisement may be blended into the beginning or ending of a song, such that it overlaps the song. In some examples, the integrated advertisement is played before or after a song without disrupting the actual song.

The example program 3200 of the illustrated example of FIG. 32 begins at block 3210 when the media presenter 165 presents media. (block 3210). In the illustrated example, the media is presented before and/or during identification of an emotion and/or mood of the media. However, in some examples, the media is presented at a later time after it has been processed for emotional classification. In the illustrated example, the example media selector 1750 passes the media to the feature extractor 125 which extracts features for use by the classification engine 130 in identifying an emotion and/or mood of the presented media. (block 3220).

The example media selector 1750 selects a brand associated with an identified emotion, mood, and/or other characteristic of the presented media. (block 3230). For example, if the media is identified as evoking a happy, cheerful, and/or other positive emotion and/or mood, a brand that desires to be associated with these characteristics may be selected. The media selector 1750 generates an integrated advertisement. (block 3240). In the illustrated example, the integrated advertisement includes information about the selected brand. However, the integrated advertisement may additionally or alternatively include other information such as, for example, a name of the presented media, a name of an artist associated with the presented media, trivia about the media, etc.

In some examples, the integrated advertisement is generated as a pre-recorded message that includes information about a song and an associated brand. In some examples, the integrated advertisement is a computer generated message based on algorithms to determine which advertiser or brand is sponsoring the presented media, and what information about the media is presented. In some examples, a different integrated advertisement is generated each time there is an advertisement spot available. If an integrated advertisement is generated each time there is an advertisement spot, many permutations of information about a media file and information about a brand are available. This variation can keep the information more interesting and enticing for listeners. In some examples, facts or slogans about a brand can be included in an integrated advertisement. The media selector 1750 instructs the media presenter 165 of the media device 160 to present the integrated advertisement. (block 3250).

Figure 33:
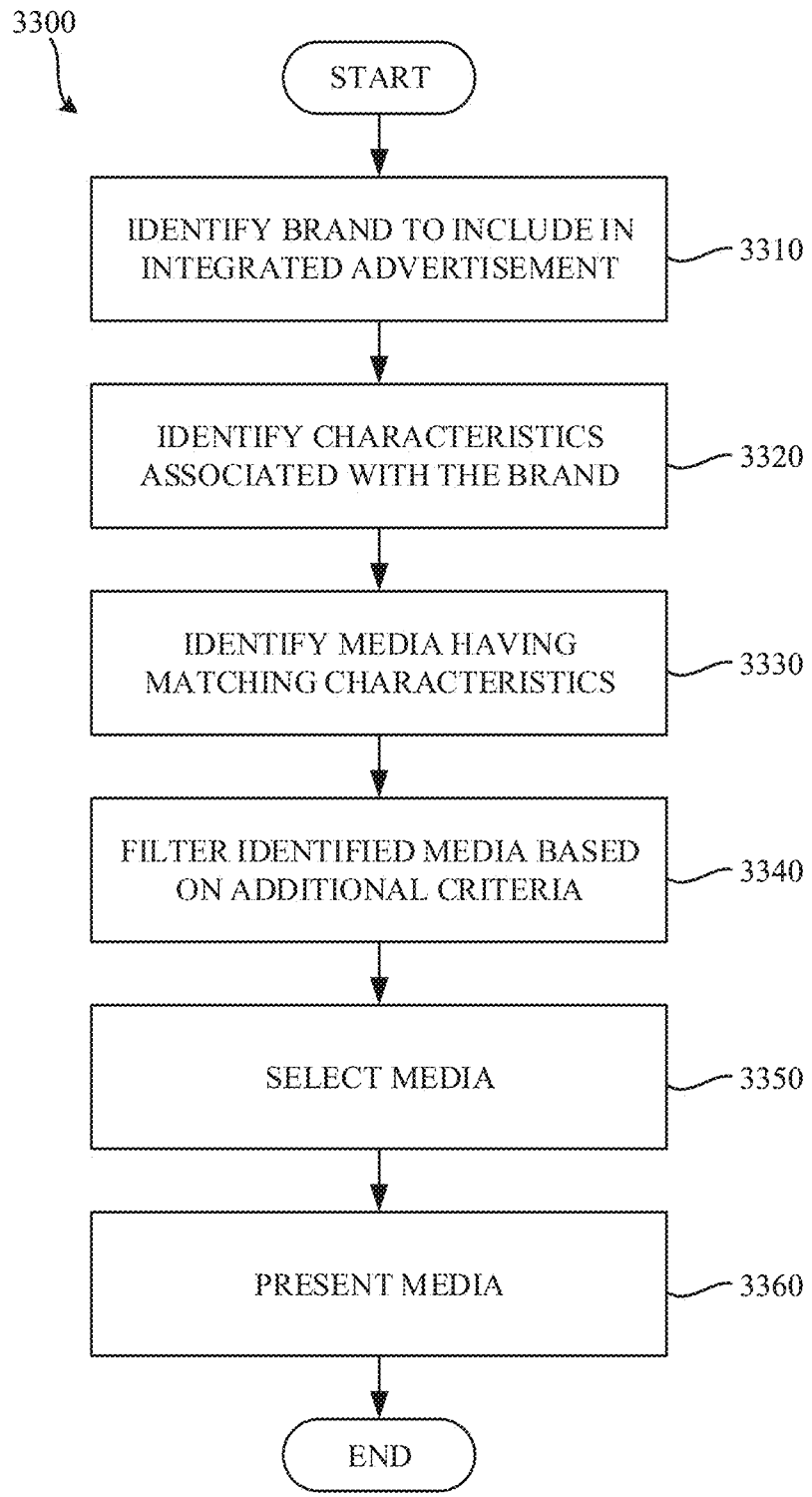
FIG. 33 is a flowchart representative of example machine readable instructions which may be executed to implement the example recommendation engine of FIGS. 1 and/or 17 to identify media to be presented proximate an integrated advertisement.

FIG. 33 is a flowchart representative of example machine readable instructions 3300 which may be executed to implement the example recommendation engine 155 of FIGS. 1 and/or 17 to identify media to be presented proximate an integrated advertisement. In some examples, media is selected for presentation based on an association and/or correlation with a particular brand. For example, the song "Happy" may be categorized as an energetic song, and may be paired with COCA COLA® to suggest being upbeat and/or appeal to a youth crowd. In some examples, happy songs could be paired with happy brands. When a brand requests that media and/or integrated advertisements be presented to a user, the media and/or integrated advertisement(s) can be selected to align with the brand and/or the emotion and/or mood the brand wishes to evoke.

The example program 3300 of the illustrated example of FIG. 33 begins when the example media selector 1750 identifies a brand to be included in an integrated advertisement. (block 3310). The media selector 1750 identifies characteristics associated with the brand. (block 3320). In the illustrated example, characteristics are identified using keywords associated with the brand. In the illustrated example, the keywords associated with the brand are specified by an entity (e.g., a person, a company, a political campaign, etc.) represented by the brand. However, keywords may be obtained in any other fashion such as, for example, an internet search, via social media, etc. However, in some examples, the owner of the brand may specify particular emotion(s) and/or mood(s) that it wishes to be associated with the brand. The example media selector 1750 identifies media evoking matching emotions and/or moods to those specified by the brand. (block 3330). In the illustrated example, multiple pieces of media may be identified as potentially aligning with the characteristics of the brand. Accordingly, in some examples, media is filtered based on additional criteria such as, for example, a popularity of the media, a year the media was created, a cost associated with presenting the media (e.g., licensing and/or royalty fees), etc. (block 3340). The example media selector 1750 selects media from the filtered set of media for presentation to the user. (block 3350). Once the media is selected for presentation, the example media presenter 165 of the example media device 160 presents the media to the user. (block 3360). In some examples, the example media presenter 165 prepares an integrated advertisement identifying the brand sponsoring the selecting media.

Figure 34:
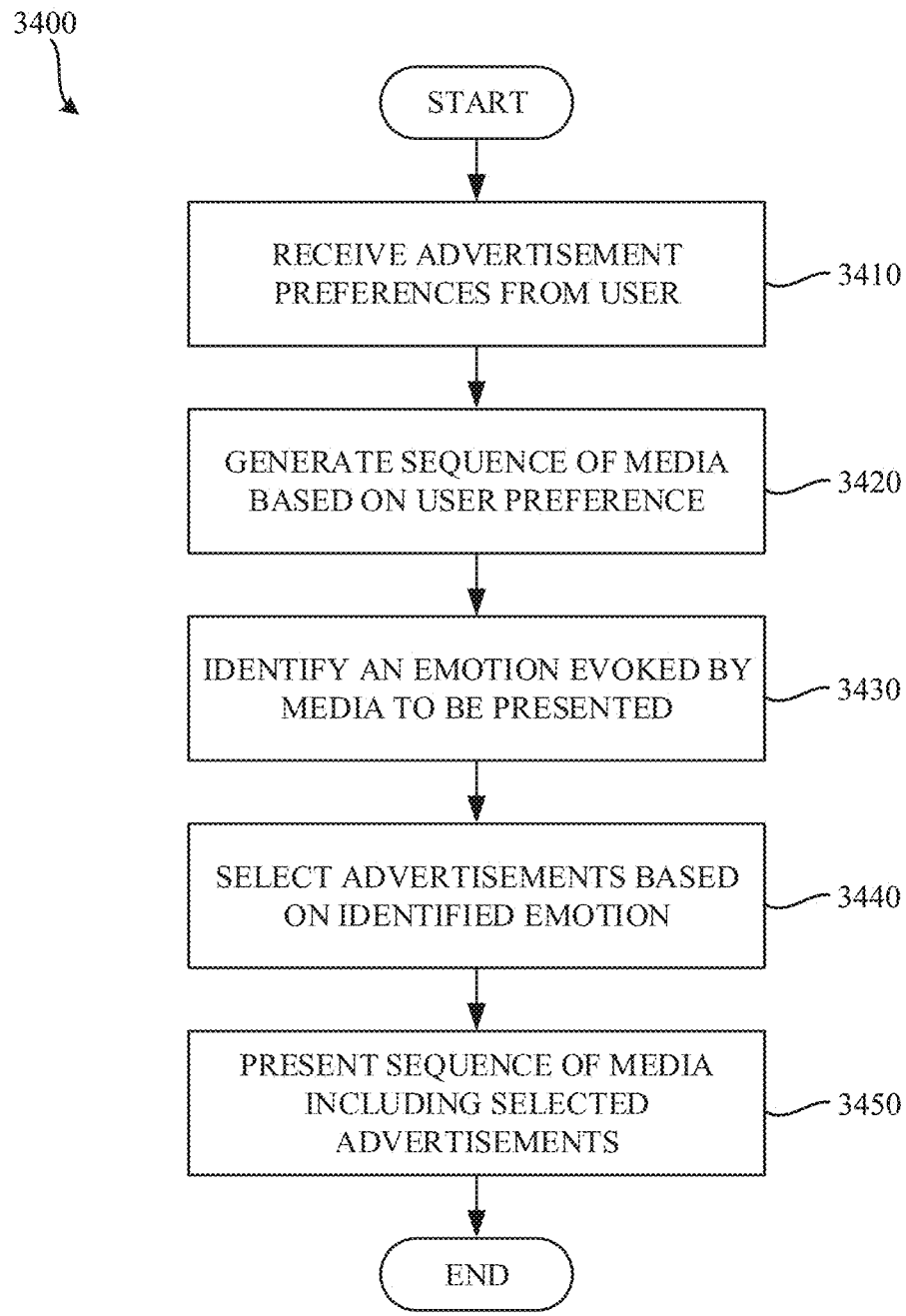
FIG. 34 is a flowchart representative of example machine readable instructions which may be executed to implement the example recommendation engine of FIGS. 1 and/or 17 to generate a sequence of media and advertisements based on a user preference.

FIG. 34 is a flowchart representative of example machine readable instructions 3400 which may be executed to implement the example recommendation engine 155 of FIGS. 1 and/or 17 to generate a sequence of media and advertisements based on a user preference. Unexpected advertisement breaks during a media presentation can be disruptive to a media exposure experience. For example, advertisements may break up a flow of presented media and can feel jarring or disruptive to an audience member. In examples disclosed herein, the user is provided options regarding the presentation of advertisements in the media. In some examples, a user can choose a number of advertisement breaks and a number of advertisements per advertisement break. For example, a user may select five advertisements in each of two advertisement breaks, two advertisements in each of five advertisement breaks, one advertisement break including ten advertisements, etc. In some examples, the user is able to select the individual advertisements that will be played during the advertisement breaks. This choice can be presented in various ways, such as by allowing the user to select specific advertisements, a category of advertisements, a particular brand featured in the advertisements, etc. Providing choices in the form of advertising presentation options keeps advertising transparent to the user. This transparency, when coupled with the ability to customize an advertisement, can produce listening experiences that are more pleasant to a user, and consequently make the advertisements more appealing and effective.

The example program 3400 of the illustrated example of FIG. 34 begins at block 3410 when the media selector 1750 receives advertisement preferences from the user. (block 3410). In the illustrated example, the advertisement preferences are received via a user interface of the media device 160. However, the advertisement preferences may be received in any other manner such as, for example, by performing a lookup of the advertisement preferences in association with the user. Based on the preferences, the media selector 1750 generates a sequence of media (e.g., content and advertisements). (block 3420). The example media selector 1750 identifies an emotion and/or mood of media to be presented during the sequence of media. (block 3430). In the illustrated example, the example media selector 1750 passes the media to the feature extractor 125 which extracts features for use by the classification engine 130 in identifying the emotion and/or mood of the media. However, the emotion and/or mood may be identified in any other way such as, for example, by inspecting metadata associated with the media. The example media selector 1750 then selects an advertisement for presentation based on the identified emotion and/or mood. (block 3440). In some examples, the advertisement is generated by the example media selector 1750 as an integrated advertisement. The media selector 1750 then directs the media presenter 165 to present the media and/or advertisement to the user according to the sequence of media. (block 3450).

Figure 35:
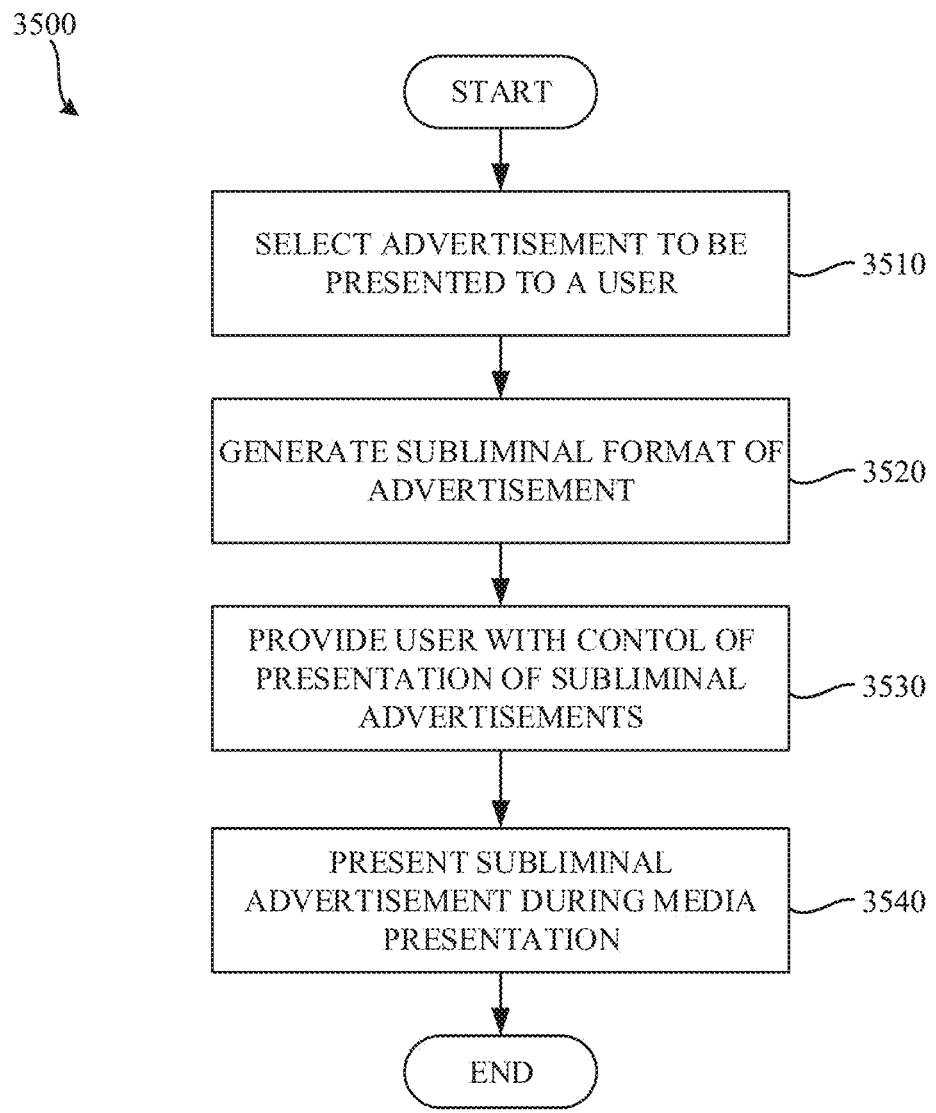
FIG. 35 is a flowchart representative of example machine readable instructions which may be executed to implement the example recommendation engine of FIGS. 1 and/or 17 to present a subliminal advertisement during a media presentation.

FIG. 35 is a flowchart representative of example machine readable instructions 3500 which may be executed to implement the example recommendation engine 155 of FIGS. 1 and/or 17 to present a subliminal advertisement during a media presentation. In some examples, advertisements are selected and then presented to the user in a subliminal fashion. In some examples, the user has the option to play the advertisement in a non-subliminal fashion. For example, the user may request that the volume of the advertisement be raised above an audible volume threshold. In some examples, subliminal advertisements can be presented intermittently during a media presentation, or in advertising blocks. In some other examples, subliminal advertisements can be presented continually. By using subliminal advertising, broadcasters can provide a less disruptive advertising presentation. In particular, a person can be continuously exposed to media without a noticeable break. At the same time, by allowing the user to selectively raise the volume of the subliminal advertisements, the subject matter of the subliminal advertisement remains transparent to the user unless the user affirmatively acts to bring the advertising to the forefront.

The example program 3500 of the illustrated example of FIG. 35 begins at block 3510 when an advertisement is selected for presentation to a user by the media selector 1750. (block 3510). The example media customizer 1760 then formats the selected advertisement into a subliminal format. (block 3520). In the illustrated example, the media selector 1750 directs the media presenter 165 to present the user with control of the presentation of subliminal advertisements. (block 3530). In the illustrated example, control is provided by enabling the user to modify a volume level of the subliminal advertisement. However, control may be provided in any other fashion such as, for example, an on/off selector to enable and/or disable presentation of subliminal advertisements, etc. The example media selector 1750 directs the media presenter 165 to present the subliminal advertisement. (block 3540). In the illustrated example, the subliminal advertisement is to be presented during presentation of another piece of media. For example, a subliminal advertisement for COCA COLA® may be presented while the song "Happy" by Pharrell Williams is presented to the user.

Figure 36:
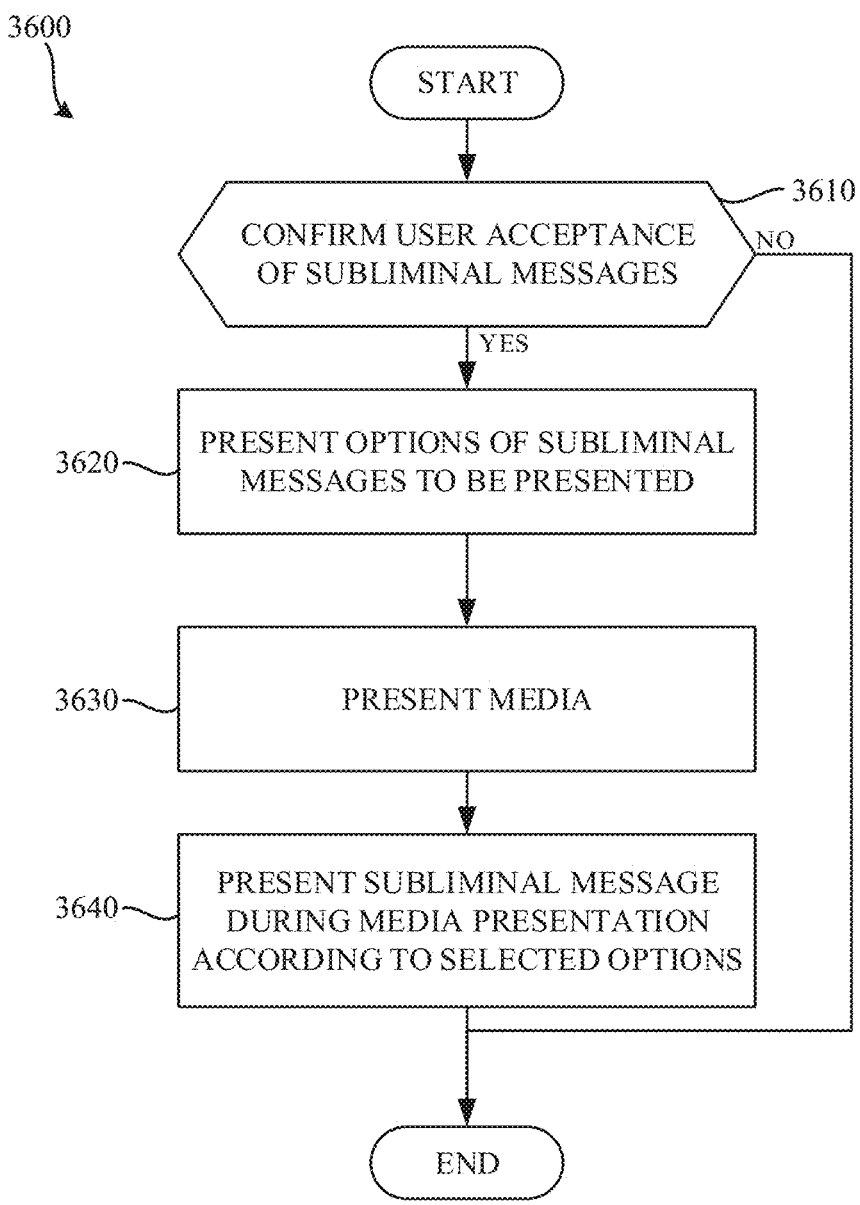
FIG. 36 is a flowchart representative of example machine readable instructions which may be executed to implement the example recommendation engine of FIGS. 1 and/or 17 to generate and present a sequence of subliminal messages to be presented during a media presentation.

FIG. 36 is a flowchart representative of example machine readable instructions 3600 which may be executed to implement the example recommendation engine 155 of FIGS. 1 and/or 17 to generate and present a sequence of subliminal messages to be presented during a media presentation. In some examples, the user may be presented with the ability to enable and/or disable the presentation of subliminal messages. In some examples, users are presented with options for subliminal messages to be presented. For example, parents may select messages such as "do not use drugs" for playback to their children's music players. In some examples, the user can select from specific prerecorded messages. In some examples, the user selects the type or subject matter of the subliminal messages. In some other examples, the user customizes and/or creates a subliminal message to be played.

The example program 3600 of the illustrated example of FIG. 36 begins at block 3610 when the example media selector 1750 confirms user acceptance of subliminal messages. (block 3610). In the illustrated example of FIG. 36, the example media selector 1750 confirms user acceptance of the subliminal messages by prompting the user via the media presenter 165. However, in some examples, the media selector 1750 accesses a user profile that indicates whether the user has accepted the presentation of subliminal messages. In some examples, subliminal messages are presented as part of a subscription service. That is, users may subscribe to a service to enable presentation of subliminal messages. The example media selector 1750 directs the example media presenter 165 to present options of subliminal messages to the user. (block 3620). In response, the example media selector 1750 receives user preferences associated with subliminal message presentation. In the illustrated example, options for presenting subliminal messages include, for example, whether subliminal advertisements may be presented, whether a particular subliminal message should be presented, etc. While in the illustrated example the user preferences for subliminal message presentation are received by prompting the user, in some examples, the user preferences are retrieved from memory (e.g., from a database, from a local memory, etc.). The example media selector 1750 instructs the example media presenter 165 to present media to the user. (block 3630). The example media selector 1750 instructs the example media presenter to present a subliminal message during the media presentation. (block 3640). In the illustrated example, the subliminal message is selected by the media selector 1750 based on the user preferences. However, in some examples, the subliminal message selection is additionally or alternatively based on an emotion and/or mood evoked by the presented media.

Figure 37:
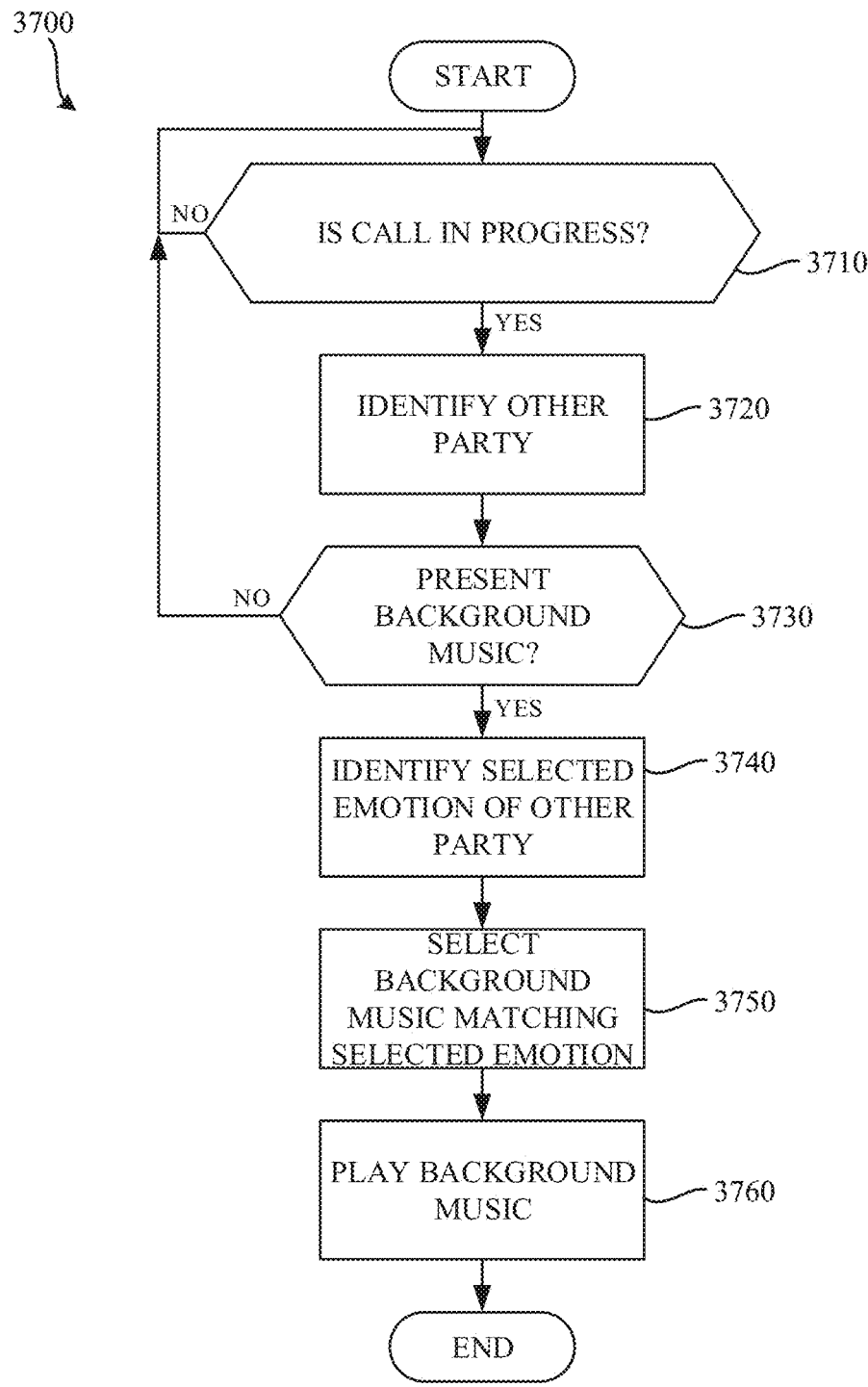
FIG. 37 is a flowchart representative of example machine readable instructions which may be executed to implement the example recommendation engine of FIGS. 1 and/or 17 to present background music during a telephone call based on a selected mood of a called party.

FIG. 37 is a flowchart representative of example machine readable instructions 3700 which may be executed to implement the example recommendation engine 155 of FIGS. 1 and/or 17 to present background music during a telephone call based on a selected mood of a called party. In some examples, listening to music can improve and/or alter a person's mood. Music is often used to set a mood for an event or calm the nerves of listeners. For example, music played at sporting events is chosen to evoke enthusiasm and excitement. In retail locations, music is chosen to attract and keep customers in a store. In a medical setting, soothing music is often played to create a calm environment for patients.

Music can provide comfort and/or can serve as a backdrop for many settings. However, the use of music during communications such as telephone calls has been limited. Although providing music while a call is placed on hold is common, providing music during a telephone conversation can affect a mood and/or tone of the conversation. In examples disclosed herein, mood-based background music is presented during communications, including telephone calls, text messages, etc. An example advantage of including background music in this manner is that the music can be selected based on a desired mood. In some examples, a user selects the mood to be set and/or promoted during a conversation. In examples disclosed herein, music can be played from a remote server, from a called party's media device, from a dialed party's media device, etc.

The example program 3700 of the illustrated example of FIG. 37 begins at block 3710 when the example context detector 1710 detects that a call is in progress by interacting and/or interfacing with the telephone functionality 166 of the media device 160. (block 3710). If a call is not in progress, the context detector 1710 waits until a call is in progress. (block 3710). If a call is in progress, the example context detector 1710 identifies the other party to the telephone conversation. (block 3720). In the illustrated example, the example context detector 1710 identifies the other party by accessing a telephone number associated with the call in progress. The telephone number is used to perform a lookup of a name of the other party and/or settings/preferences associated with the other party As used herein, the other party refers to any party participating in a telephone call other than the user of the media device 160. For example, the other party might have been dialed by entering a telephone number, the call may have been placed using a contact name, the other party may have placed the call, etc. In some examples, the call may be an incoming call in that the other party contacted the user of the media device 160. In some examples, multiple other parties may exist (e.g., a three way call).

As disclosed in connection with FIG. 19, the user may enter various settings and/or preferences for different parties. Based on the settings and/or preferences of the other party, the example media selector 1750 determines whether background music should be presented. (block 3730). If background music is not to be presented, control returns to block 3710. In some examples, the user preference for whether background music is presented may change during a call. As such, the media selector 1750 may repeat the determination of whether background music is to be presented throughout the duration of the call.

If background music is to be presented (block 3730), the example desired mood detector 1740 accesses the settings and/or preferences associated with the other party to identify a selected emotion and/or mood of the other party. (block 3740). For example, in the context of FIG. 19, when a call is identified with Anne Wong, the example desired mood detector 1740 identifies that friendly background music is selected. Based on the identified emotion and/or mood, the example media selector 1750 selects background music to be presented. (block 3750). The media selector 1750 then directs the media presenter 165 of the media device 160 to present the selected background music via the telephone call (block 3760). In some examples, the background music may be modified to sound as though the background music is coming from an environment of the user of the media device 160, such as, for example, from a music player playing in the same room as the user of the media device 160.

In some examples, mood-based music can be played along with a text message, media message, and/or other message (e.g., email, social media notification, etc.). In some examples, the mood-based music selection can be played as a notification sound for the incoming message. In other examples, the mood-based music selection can be played once the message is opened and/or viewed. In some examples, a mood-based music selection can be played during both notification and viewing of a text message.

Figure 38:
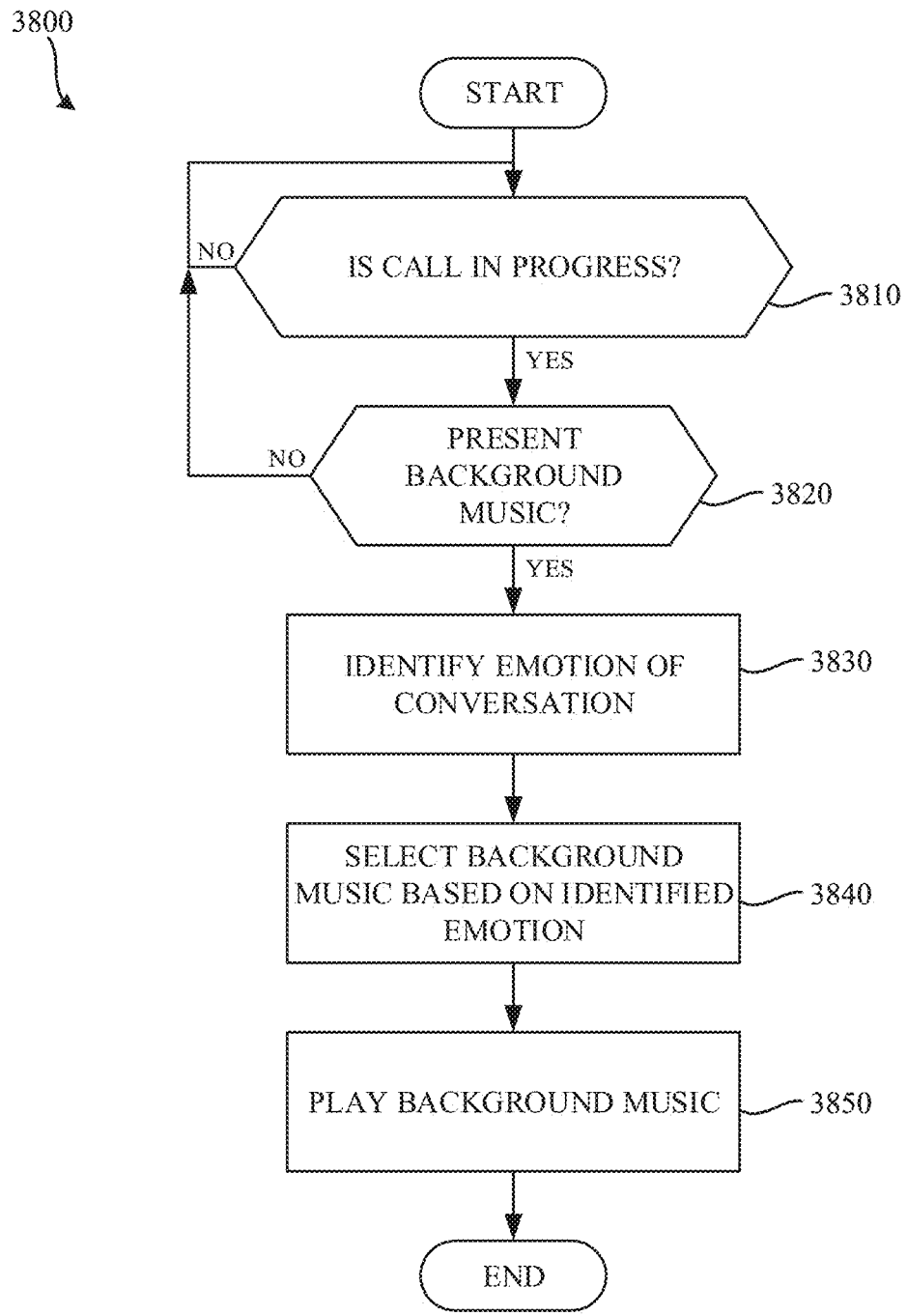
FIG. 38 is a flowchart representative of example machine readable instructions which may be executed to implement the example recommendation engine of FIGS. 1 and/or 17 to present background music during a telephone call based on an identified mood of a conversation.

FIG. 38 is a flowchart representative of example machine readable instructions 3800 which may be executed to implement the example recommendation engine of FIGS. 1 and/or 17 to present background music during a telephone call based on an identified mood of a conversation. In some examples, the selection of mood-based background music is based on conversational dynamics. For example, if a discussion becomes overly heated, more calming music can be played to change the mood of the discussion. In response, an entirely different piece of music can be played, existing music may be played in a different manner to elicit a different mood, etc. In some examples, the mood of the conversation is detected using a sensor of the media device 160 such as, for example, a camera, a microphone, a body heat sensor, etc.

The example program 3800 of the illustrated example of FIG. 38 begins at block 3810 when the example context detector 1710 detects that a call is in progress by interacting and/or interfacing with the telephone functionality 166 of the media device 160. (block 3710). If a call is not in progress, the context detector 1710 waits until a call is in progress. (block 3710). If a call is in progress, the example media selector 1750 determines whether background music should be presented. (block 3820). In the illustrated example, the example media selector 1750 determines that background music should be presented when a user of the media device 160 has indicated a preference that background music be presented. However, in some other examples, background music may be presented when, for example, an emotion, a mood, and/or tone of a conversation strays from a desired emotion, a mood, and/or tone of the conversation.

If background music is to be presented, the example user mood detector 1730 identifies a current emotion and/or mood of the conversation. (block 3830). In the illustrated example, the current emotion and/or mood of the conversation is identified by interfacing with the telephone functionality 166 of the media device 160 to receive an audio sample of the conversation, and requesting that the feature extractor 125 and/or the classification engine 130 identify an emotion and/or mood evoked by the conversation. Because, in some examples, pre-verbal training data based on human speech is used as part of the training data 135, the mood model implemented by the classification engine 130 is adept at identifying an emotion and/or mood evoked by human speech during, for example, a telephone conversation. In some examples, speech recognition and semantic analysis are employed to identify an emotion and/or mood of the conversation.

Using the identified emotion and/or mood of the conversation, the example media selector 1750 selects media for presentation as background music. (block 3840). In some examples, the media selector 1750 selects media based on a desired emotion and/or mood of the telephone call. The media selector 1750 then directs the media presenter 165 of the media device 160 to present the selected background music via the telephone call (block 3850).

Figure 39:
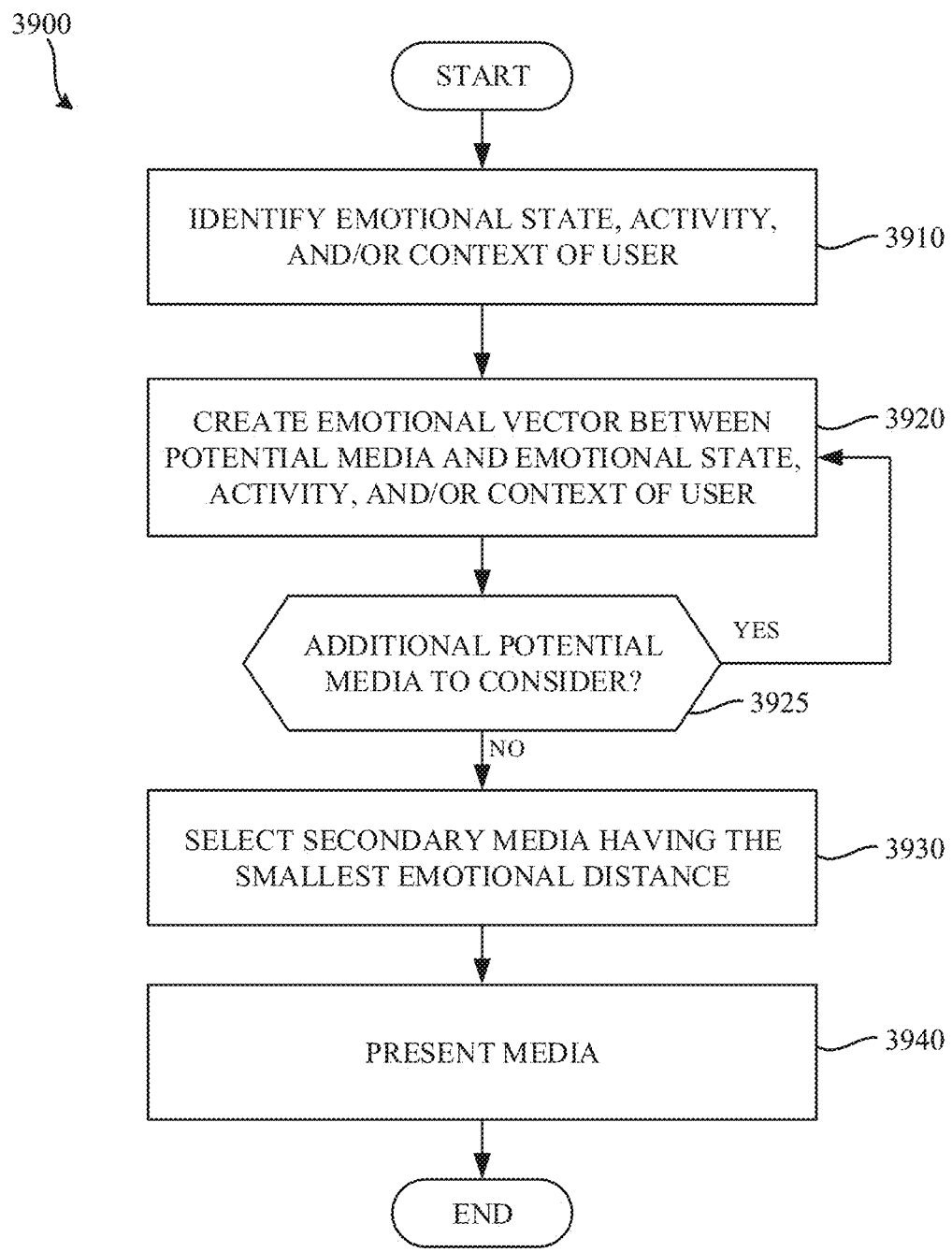
FIG. 39 is a flowchart representative of example machine readable instructions which may be executed to implement the recommendation engine of FIGS. 1 and/or 17 to select media based on an emotional distance between media and an emotional state, an activity, and/or a context of a user.

FIG. 39 is a flowchart representative of example machine readable instructions 3900 which may be executed to implement the recommendation engine 155 of FIGS. 1 and/or 17 to select media based on an emotional distance between media and an emotional state, an activity, and/or a context (e.g., an environment) of a user. In some examples, a strong indicator of the best media for selection for presentation at a particular moment is a context and/or activity of a listener. Although a listener may generally enjoy soft rock or rhythm and blues, the tastes of the listener may change during particular activities and/or in particular environments. For example, a listener who is jogging may prefer a different type of music than the standard jazz that the listener normally enjoys. In other examples, the listener may prefer different music while riding a subway to work versus riding the subway home, and/or may prefer different genres when working at a computer than when eating. In some examples, a context and/or activity of a user influences the type, tone, and quality of music that is selected for presentation.

The example program 3900 of the illustrated example of FIG. 39 begins at block 3910 when the example context detector 1710 identifies an emotional state, activity, and/or context of a user. (block 3910). In the illustrated example, the example context detector 1710 interfaces with the sensor 167 of the media device 160 to identify the emotional state, the activity, and/or the context of the user. For example, the sensor(s) 167 may be used to provide data for analysis to determine whether the user in front of a television, shopping in the supermarket, hiking, etc. For example, if a GPS sensor identifies that the user is at a gym, the context of the user may be identified as a workout. In some examples, location information can assist in identifying whether the user is at work, at home, at the gym, etc. Location information and accelerometer data can distinguish between sitting, walking, running, etc. Other sensors, such as microphones and magnetometers, can also contribute data useful for detecting the emotional state, the activity, and/or the context of the user. Example uses of sensors to detect an emotional state of a user are described in U.S. patent application Ser. No. 13/730,212, which is hereby incorporated by reference in its entirety.

Once the emotional state, the activity, and/or the context of the user is established by the context detector 1710, an emotional distance representing a difference between potential media for presentation and the emotional state, the activity, and/or the context of the user. (block 3920). An example data table 3970 is shown in the illustrated example of FIG. 39A. In the illustrated example of FIG. 39A, in contrast to FIG. 18, the data table 3970 includes columns representing various contexts and/or activities of a user, in addition to the emotional identifications of the example data table of FIG. 18. The example data table 3970 includes a happy column 3982, a sad column 3984, a joyful column 3986, an indoor context column 3988, a workout activity column 3990, and an emotional distance column 3992. For example, media may be identified as being highly correlated with a particular activity (e.g., a workout). As such, when the emotional distance is calculated for media exhibiting a high correlation with an activity of a user, the resultant emotional distance is small, thereby increasing the likelihood that the media will be selected for presentation.

As described in connection with FIG. 18, differences between the values of the media columns and the desired emotion, context, and/or activity columns are calculated. While the media rows (e.g., media A 3972, media B 3974, and media C 3976) include the same values as the media rows for the emotion columns (e.g., the happy column 3982, the sad column 3984, the joyful column 3986) shown in FIG. 18, the context and/or activity columns result in different values for the emotional distances associated with the media. As a result, the example media selector 1750 selects media B in the example of FIG. 39A, whereas media A was selected in the example of FIG. 18. In some examples, the emotional distance is combined with user preferences to allow selection of media that is relevant to the user's preferences as well as the emotional state, the activity, and/or the context of the user.

The example media selector 1750 determines if there is other potential media to consider. (block 3925). In some examples, media is omitted from consideration if it was recently presented to the user (e.g., presented within the last hour, presented within the last week, etc.) If additional media is to be considered (block 3925), control proceeds to block 3920, where an emotional distance for the additional media is created. (block 3920). If no additional media is to be considered (block 3925), the example media selector 1750 selects the media having the smallest emotional distance. (block 3930). The media selector 1750 then directs the media presenter 165 to present the selected media to the user. (block 3940).

Figure 40:
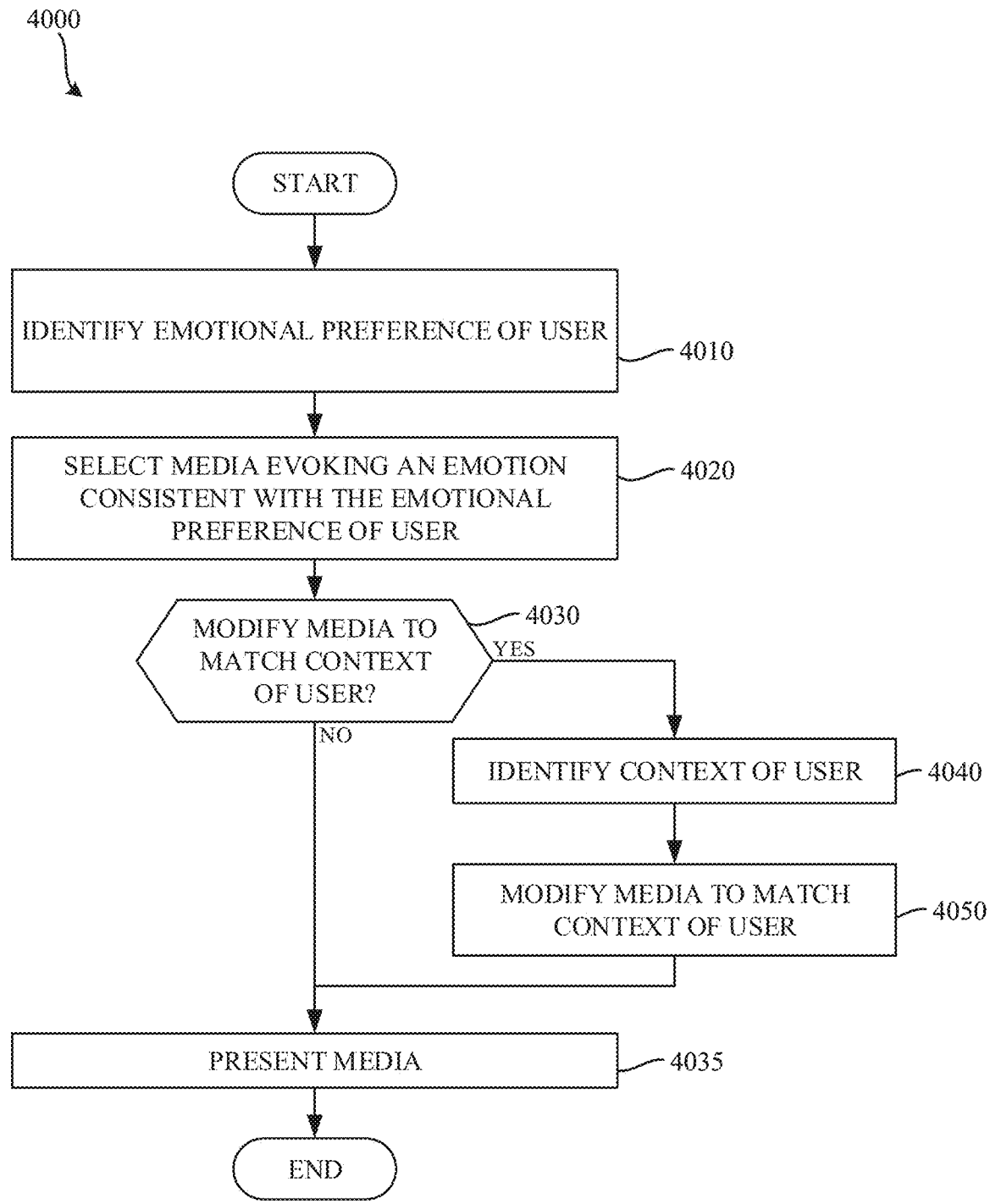
FIG. 40 is a flowchart representative of example machine readable instructions which may be executed to implement the example recommendation engine of FIGS. 1 and/or 17 to modify a media presentation to match a context of a user.

FIG. 40 is a flowchart representative of example machine readable instructions 4000 which may be executed to implement the example recommendation engine 155 of FIGS. 1 and/or 17 to modify a media presentation to match a context of a user. In some examples, the example media customizer 1760 of the example recommendation engine 155 modifies, and/or the example media selector 1750 of the example recommendation engine 155 selects, media presented to a user so that the media presentation is appropriate for the context of the user. For example, media appropriate for jogging may be identified, and/or particular emotional states associated with jogging may be identified when a user is participating in jogging. Activities and/or contexts may be mapped to emotion(s) and/or mood(s) which are, in some examples, used to select and/or modify media for presentation. The example media customizer 1760 selectively modifies media using information associated with an activity, context, etc. of a user. For example, a pace, a rhythm, a cadence, etc. of the media may be modified to match the jogger's pace or heart rate. In some examples, the tone and volume of music may be adjusted to match a relaxation level of the user. In some examples, bass and treble components of the media may be emphasized or deemphasized by, for example, applying an audio filter. The media is then presented to the user via, for example, a media stream presented by the media device 160. In some examples, media may be adapted at and/or played locally from the media device 160 (e.g., from a memory of the media device). Media may be adapted at the media device 160 by, for example, presenting the media at a different pace, presenting the media at a different volume, etc.

The example program 4000 of the illustrated example of FIG. 40 begins at block 4010 when the desired mood detector 1740 identifies an emotional preference of the user. (block 4010). In the illustrated example, the desired mood detector 1740 identifies the emotional preference by prompting the user to select an emotional preference. However, in some examples, the desired mood detector 1740 may retrieve the emotional preference from a memory (e.g., a memory of the media device 160, the mood model database 140, a memory of the recommendation engine 155, etc.) In some examples, the user's past preferences (e.g., based on historical data) are used to identify the emotional preference of the user. In some examples, the user mood detector 1730 detects a present emotion and/or mood of the user. For example, the example user mood detector 1730 may identify that the user is excited, forlorn, and/or happy using, for example, emotional facial action coding systems (FACs), facial analysis, neurological analysis, voice analysis with the classification engine 130, etc.

The example media selector 1750 selects media evoking an emotion and/or mood consistent with the emotional preferences of the user. (block 4020). In some examples, the example media selector 1750 maps an activity and/or context of the user to a particular emotion, moo, and/or particular characteristics of media that would be appropriate for a particular activity, mood, and/or context. For example, media appropriate for jogging may be identified when the user is jogging, and/or particular emotional states associated with jogging may be identified when a user is jogging.

The example media customizer 1760 then determines if the media is to be modified to match a context, mood, and/or activity of the user. (block 4030). If media is not to be customized, the example media selector 1750 instructs the example media presenter 165 to present the media. (block 4035). If media is to be customized, the example context detector identifies an emotional state, activity, and/or context of a user. (block 4040). In the illustrated example, the example context detector 1710 interfaces with the sensor 167 of the media device 160 to identify the emotional state, the activity, and/or the context of the user. In some examples, the sensor 167 is implemented using a headset to monitor the emotional state, the activity, and/or the context of the user.

The example media customizer 1760 then modifies the media to match the emotional state, activity, and/or context of the user. (block 4050). In the illustrated example, a tempo of the media is modified to, for example, match a jogging pace of a user while the user is exercising. In the illustrated example, the tempo of the media is modified by presenting the media at a speed other than its intended presentation speed. For example, media may be presented using a faster tempo by presenting the media at one hundred and ten percent (110%) of the intended presentation rate. In contrast, media may be presented using a slower tempo by presenting the media at ninety percent (90%) of the intended presentation rate. However, any other type of modification and/or customization may additionally or alternatively be made. For example, a pace, a rhythm, a cadence, a pitch, etc. may be modified to match the emotional state, activity, and/or context of the user. The example media selector 1750 instructs the example media presenter 165 to present the customized media. (block 4035).

Figure 41:
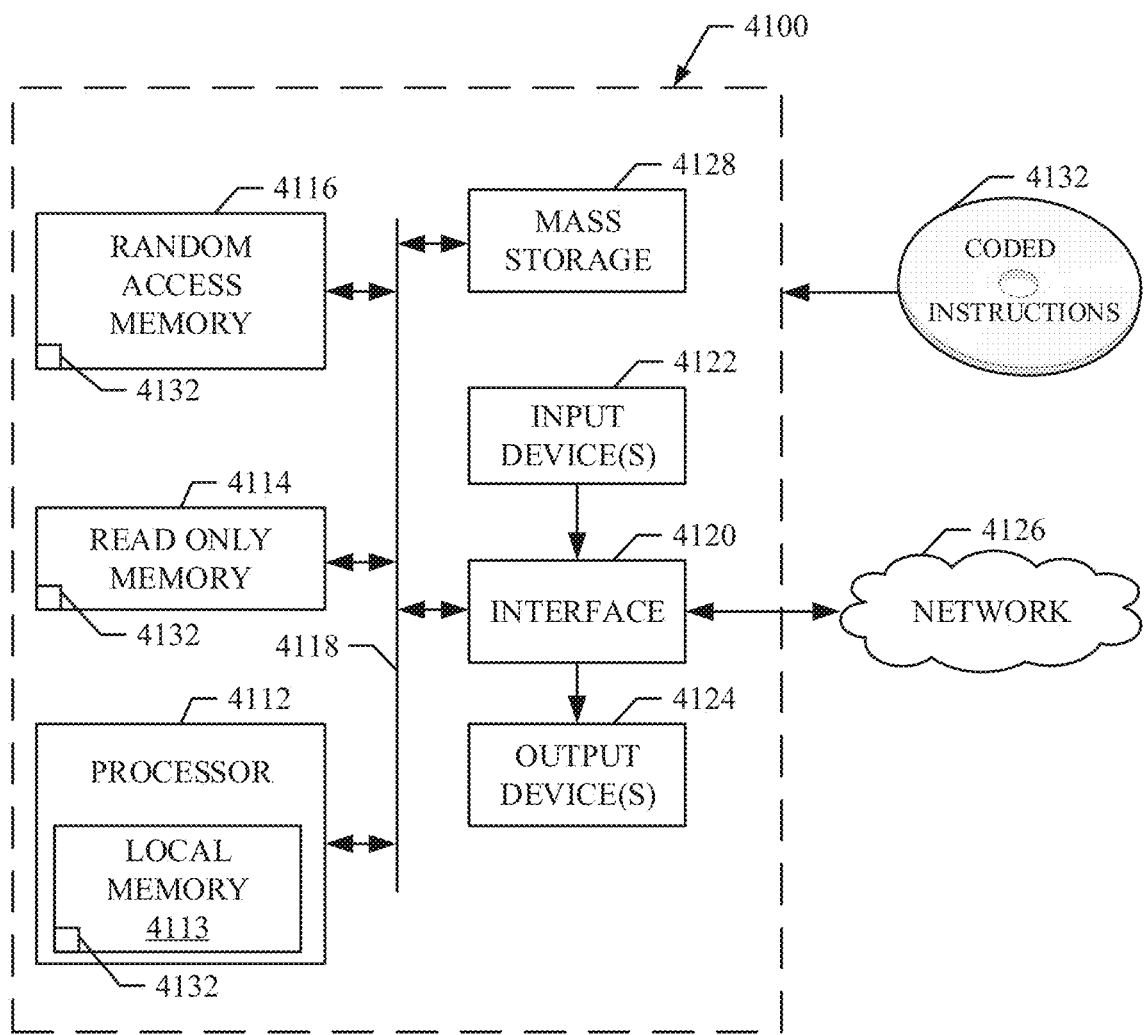
FIG. 41 is a block diagram of an example processor platform capable of executing the example machine-readable instructions of FIGS. 20, 21, 22, 23, 24, 25, 26, 27, 28, 29, 30, 31, 32, 33, 34, 35, 36, 37, 38, 39, and/or 40 to implement the example sample generator of FIGS. 1 and/or 2, the example feature extractor of FIGS. 1 and/or 3, the example classification engine of FIGS. 1 and/or 13, the example mood model validator of FIGS. 1 and/or 16, and/or the example recommendation engine of FIGS. 1 and/or 17.

FIG. 41 is a block diagram of an example processor platform 4100 capable of executing the instructions of FIGS. 21, 22, 23, 24, 25, 26, 27, 28, 29, 30, 31, 32, 33, 34, 35, 36, 37, 38, 39, and/or 40 to implement the example audio receiver 115, the example sample generator 120, the example, feature extractor 125, the example classification engine 130, the example mood model validator 145, the example recommendation engine 155, and/or, more generally, the example mood-based media recommendation system 105 of FIG. 1. The processor platform 4100 can be, for example, a server, a personal computer, a mobile device (e.g., a cell phone, a smart phone, a tablet such as an iPad™), a personal digital assistant (PDA), an Internet appliance, a digital video recorder, a Blu-ray player, a gaming console, a personal video recorder, a set top box, or any other type of computing device.

The processor platform 4100 of the illustrated example includes a processor 4112. The processor 4112 of the illustrated example is hardware. For example, the processor 4112 can be implemented by one or more integrated circuits, logic circuits, microprocessors, or controllers from any desired family or manufacturer.

The processor 4112 of the illustrated example includes a local memory 4113 (e.g., a cache). The processor 4112 of the illustrated example is in communication with a main memory including a volatile memory 4114 and a non-volatile memory 4116 via a bus 4118. The volatile memory 4114 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 4116 may be implemented by flash memory and/or any other desired type of memory device. Access to the main memory 4114, 4116 is controlled by a memory controller.

The processor platform 4100 of the illustrated example also includes an interface circuit 4120. The interface circuit 4120 may be implemented by any type of interface standard, such as an Ethernet interface, a universal serial bus (USB), and/or a PCI express interface.

In the illustrated example, one or more input devices 4122 are connected to the interface circuit 4120. The input device(s) 4122 permit(s) a user to enter data and commands into the processor 4112. The input device(s) can be implemented by, for example, an audio sensor, a microphone, a camera (still or video), a keyboard, a button, a mouse, a touchscreen, a track-pad, a trackball, isopoint, and/or a voice recognition system.

One or more output devices 4124 are also connected to the interface circuit 4120 of the illustrated example. The output devices 4124 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), and/or speakers). The interface circuit 4120 of the illustrated example, thus, typically includes a graphics driver card, a graphics driver chip or a graphics driver processor.

The interface circuit 4120 of the illustrated example also includes a communication device such as a transmitter, a receiver, a transceiver, a modem and/or network interface card to facilitate exchange of data with external machines (e.g., computing devices of any kind) via a network 4126 (e.g., an Ethernet connection, a digital subscriber line (DSL), a telephone line, coaxial cable, a cellular telephone system, etc.).

The processor platform 4100 of the illustrated example also includes one or more mass storage devices 4128 for storing software and/or data. Examples of such mass storage devices 4128 include floppy disk drives, hard drive disks, compact disk drives, Blu-ray disk drives, RAID systems, and digital versatile disk (DVD) drives.

The coded instructions 4132 of FIGS. 21, 22, 23, 24, 25, 26, 27, 28, 29, 30, 31, 32, 33, 34, 35, 36, 37, 38, 39, and/or 40 may be stored in the mass storage device 4128, in the volatile memory 4114, in the non-volatile memory 4116, and/or on a removable tangible computer readable storage medium such as a CD or DVD.

From the foregoing, it will be appreciated that example methods, apparatus, and articles of manufacture disclosed herein enable identification and/or classification of emotion(s) and/or moods evoked by media. Some disclosed methods, apparatus, and articles of manufacture enable recommendation of media based on, for example, a desired mood, a brand association, a tone of a telephone conversation, a current mood of a user, etc.

Example methods, apparatus, and articles of manufacture disclosed herein offer advantages with respect to computing resources. Because the mood model incorporates pre-verbal utterances, a mood of media can be identified more quickly and accurately. As a result, processing and memory requirements of media recommendation systems are reduced. In some examples, when using actual songs in training, by using short time segments (e.g., one second segments, ten second segments, etc.) such assessment enables more accurate emotion and/or mood identification which leads to less computations during training of the mood model.

Moreover, the use of pre-verbal utterances as part of the training model enables accurate and quick identification of an emotion and/or mood of a user. As such, a shorter durations of a user's speech must be analyzed to identify an emotion of a user. Using shorter durations of a user's speech reduces bandwidth requirements (e.g., shorter durations of speech require less data to be transferred than longer durations of speech) and memory requirements (e.g., shorter durations of speech require less data to be stored than longer durations of speech).

Example methods, apparatus, and articles of manufacture disclosed herein offer therapeutic benefits as a result of media selection based on a mood of a user. For example, if a user is in a negative state (e.g., a depressed state, a sad state, etc.) media may be selected to bring the user to a positive state (e.g., relaxed, calm, etc.). This is a benefit that can reduce risks of hypertension in a user, reduce risk of a heart attack, reduce risk of stroke, reduce risk of suicide, etc.

Example methods, apparatus, and articles of manufacture disclosed herein offer more accurate mood classification of media. As a result, in a streaming context, users are less likely to "skip" media presented via a media streaming application. This reduced "skip" rate, in turn, results in a decreased bandwidth usage and/or requirements for the media streaming application.

In an advertising context, mood-based advertisement selection results in more effective advertisements being selected for particular users exhibiting particular emotion(s). As a result, brands and/or advertising entities may increase advertisement effectiveness by selecting mood-appropriate advertisements. Using mood-appropriate advertisements reduces the need for multiple advertisement placements, reduces instances of advertisement skipping, etc. Reduced advertisement skipping saves bandwidth resources, and saves times by increasing the value of advertisement presentations. When advertisement effectiveness is increased, brands and/or advertising entities are enabled to spend advertising budgets more effectively.

Although certain example methods, apparatus, and articles of manufacture have been disclosed herein, the scope of coverage of this patent is not limited thereto. On the contrary, this patent covers all methods, apparatus, and articles of manufacture fairly falling within the scope of the claims of this patent.

We claim:

1. An apparatus to identify an emotion evoked by media, the apparatus comprising:
    notator circuitry to create a musical representation of a pre-verbal utterance known to evoke a first emotion;
    display controller circuitry to cause a display to present an interface to instruct a musician to perform the musical representation of the pre-verbal utterance;
    a feature extractor to identify a first value of a first feature of a recording of the performance of the musical representation of the pre-verbal utterance, the feature extractor to identify a second value of the first feature of first media evoking an unknown emotion;
    a classification engine to create a model based on the first feature, the model to establish a relationship between the first value of the first feature and the first emotion, the classification engine to identify the unknown emotion as the first emotion when the model indicates that the second value corresponds to the first value; and
    a recommendation engine to calculate emotional distances between respective ones of potential media for recommendation and the first emotion, the recommendation engine to select one of the potential media based on the respective emotional distances.

2. The apparatus as described in claim 1, wherein the feature extractor is to identify a third value of the first feature of second media as evoking the first emotion, and further including a model validator to validate the model by confirming that the model indicates that the first value of the first feature is within a threshold percentage of the third value of the first feature.

3. The apparatus as described in claim 2, wherein the validator includes a semantic mapper to map a second emotion identified as being evoked by the first media to the first emotion.

4. The apparatus as described in claim 1, wherein the recommendation engine is to recommend the first media in response to a request for media evoking the first emotion.

5. The apparatus as described in claim 1, wherein the feature extractor includes at least one of a zero crossing identifier, a rolloff power identifier, a brightness identifier, a roughness identifier, a minor third interval identifier, a major third interval identifier, an irregularity identifier, a chroma identifier, a main pitch identifier, or a key identifier.

6. The apparatus as described in claim 1, wherein the feature extractor includes at least three of zero crossing identifier, a rolloff power identifier, a brightness identifier, a roughness identifier, a minor third interval identifier, a major third interval identifier, an irregularity identifier, a chroma identifier, a main pitch identifier, or a key identifier.

7. A non-transitory machine readable storage medium comprising instructions which, when executed, cause a machine to at least:
create a musical representation of a pre-verbal utterance known to evoke a first emotion;
cause display of an interface to instruct a musician to perform the musical representation of the pre-verbal utterance;
calculate a first value of a first feature of a recording of the performance of the musical representation of the pre-verbal utterance;
create a model based on the first value of the first feature, the model to establish a relationship between the first value of the first feature and the first emotion;
identify a second value of the first feature of first media evoking an unknown emotion;
identify the unknown emotion as the first emotion when the model indicates that the second value corresponds to the first value;
calculate emotional distances between respective ones of potential media for recommendation and the first emotion; and
recommend one of the potential media based on the respective emotional distances.

8. The non-transitory machine readable storage medium as described in claim 7, wherein the instructions, when executed, cause the machine to use a synthesized musical instrument to synthesize a first synthesized sample.

9. The non-transitory machine readable storage medium as described in claim 8, wherein the musical representation of the pre-verbal utterance is a Musical Instrument Digital Interface representation of the pre-verbal utterance.

10. The non-transitory machine readable storage medium as described in claim 9, wherein the instructions, when executed, cause the machine to:
generate a vocoder representation of the Musical Instrument Digital Interface representation; and
use the vocoder representation to synthesize the first synthesized sample.

11. The non-transitory machine readable storage medium as described in claim 7, wherein the instructions, when executed, cause the machine to generate a vocoder representation of the recording.

12. The non-transitory machine readable storage medium as described in claim 7, wherein the instructions, when executed, cause the machine to instruct the musician to emulate the pre-verbal utterance.

13. The non-transitory machine readable storage medium as described in claim 7, wherein the instructions, when executed, cause the machine to at least:
identify a second value of the first feature of second media evoking the first emotion; and
confirm that the emotion model indicates that the second media corresponds to the first emotion.

14. The non-transitory machine readable storage medium as described in claim 13, wherein the instructions, when executed, cause the machine to update the model when the second value of the first feature does not correspond to the first value of the first feature.

15. The non-transitory machine readable storage medium as described in claim 7, wherein the first feature is at least one of a number of zero crossings, a rolloff power, a brightness, a roughness, a presence of a minor third interval, a presence of a major third interval, an irregularity, a chroma, a main pitch, or a key.

16. The non-transitory machine readable storage medium as described in claim 7, wherein the instructions, when executed, cause the machine to at least:
identify a request for media evoking the first emotion; and
recommend second media as evoking the first emotion.

17. The non-transitory machine readable storage medium as described in claim 7, wherein the instructions, when executed, cause the machine to identify the first emotion based on an emotion evoked by primary media.

18. A method to identify an emotion evoked by media, the method comprising:
creating, by executing an instruction with a processor, a musical representation of a pre-verbal utterance known to evoke a first emotion;
causing, by executing an instruction with a processor, a display device to present an interface to instruct a musician to perform the musical representation of the pre-verbal utterance;
accessing, by executing an instruction with the processor, a first sample of the musician performing the musical representation of the pre-verbal utterance;
calculating, by executing an instruction with the processor, a first value of a first feature of the first synthesized sample;
creating, by executing an instruction with the processor, a model based on the first value of the first feature, the model to establish a relationship between the first value of the first feature and the first emotion;
identifying, by executing an instruction with the processor, a second value of the first feature of first media evoking an unknown emotion;
identifying, by executing an instruction with the processor, the unknown emotion as the first emotion when the model indicates that the second value corresponds to the first value;
calculating, by executing an instruction with the processor, emotional distances between respective ones of potential media for recommendation and the first emotion; and
recommending, by executing an instruction with the processor, one of the potential media based on the respective emotional distances.

* * * * *